(12) United States Patent
Waters

(10) Patent No.: US 10,400,005 B2
(45) Date of Patent: Sep. 3, 2019

(54) SUBSTITUTED PURINE COMPOUNDS

(71) Applicant: Epizyme, Inc., Cambridge, MA (US)

(72) Inventor: Nigel J. Waters, Belmont, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 15/632,173

(22) Filed: Jun. 23, 2017

(65) Prior Publication Data
US 2018/0127451 A1 May 10, 2018

Related U.S. Application Data

(63) Continuation of application No. 14/902,150, filed as application No. PCT/US2014/045406 on Jul. 3, 2014, now Pat. No. 9,688,714.

(60) Provisional application No. 61/842,701, filed on Jul. 3, 2013.

(51) Int. Cl.
| | | |
|---|---|---|
| *A01N 43/04* | (2006.01) | |
| *A61K 31/70* | (2006.01) | |
| *C07H 19/16* | (2006.01) | |
| *C12Q 1/6886* | (2018.01) | |
| *G01N 33/574* | (2006.01) | |
| *A61K 31/7076* | (2006.01) | |
| *A61K 31/7064* | (2006.01) | |
| *A61K 31/706* | (2006.01) | |

(52) U.S. Cl.
CPC .......... *C07H 19/16* (2013.01); *C12Q 1/6886* (2013.01); *G01N 33/57426* (2013.01); *G01N 33/57484* (2013.01); *A61K 31/706* (2013.01); *A61K 31/7064* (2013.01); *A61K 31/7076* (2013.01); *C12Q 2600/158* (2013.01); *G01N 2333/47* (2013.01); *G01N 2333/715* (2013.01); *G01N 2333/91017* (2013.01); *Y02A 50/401* (2018.01); *Y02A 50/409* (2018.01); *Y02A 50/411* (2018.01)

(58) Field of Classification Search
None
See application file for complete search history.

(56) References Cited

U.S. PATENT DOCUMENTS

| | | |
|---|---|---|
| 8,580,762 B2 | 11/2013 | Olhava et al. |
| 9,096,634 B2 | 8/2015 | Olhava et al. |
| 9,688,714 B2 | 6/2017 | Waters |
| 2012/0142625 A1* | 6/2012 | Olhava ............... C07D 487/04 514/46 |
| 2015/0366893 A1 | 12/2015 | Olhava et al. |

OTHER PUBLICATIONS

Daigle et al., "Selective Killing of Mixed Lineage Leukemia Cells by a Potent Small-Molecule DOT1L Inhibitor," *Cancer Cell*, Jul. 12, 2011, pp. 53-65, vol. 20.

* cited by examiner

*Primary Examiner* — Patrick T Lewis
(74) *Attorney, Agent, or Firm* — Cooley LLP; Heidi A. Erlacher; Xixi Sun

(57) ABSTRACT

The present invention relates to substituted purine compounds. The present invention also relates to pharmaceutical compositions containing these compounds and methods of treating disorders in which DOT1-mediated protein methylation plays a part, such as cancer, by administering these compounds and pharmaceutical compositions to subjects in need thereof.

29 Claims, 15 Drawing Sheets

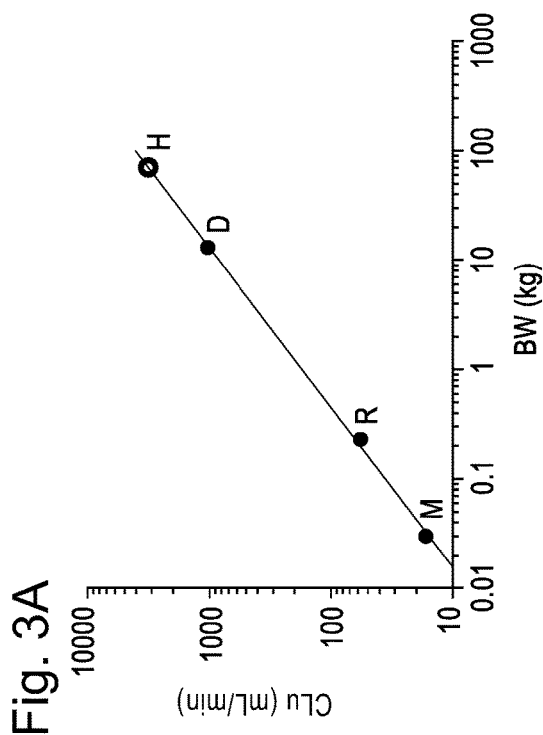
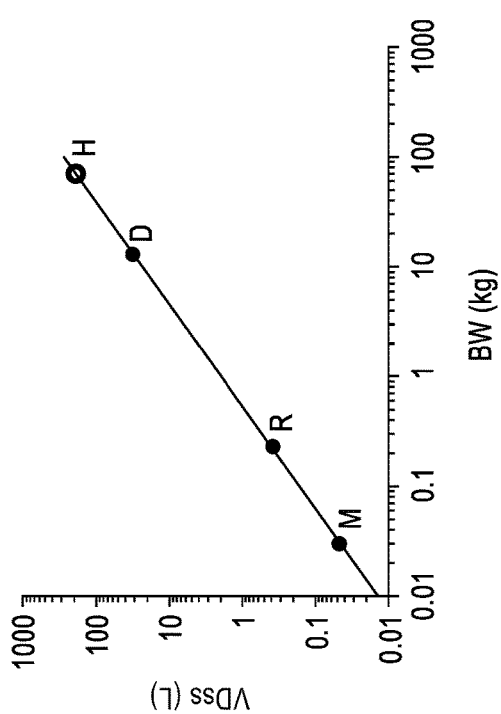
Fig. 3A, Fig. 3B, Fig. 3C

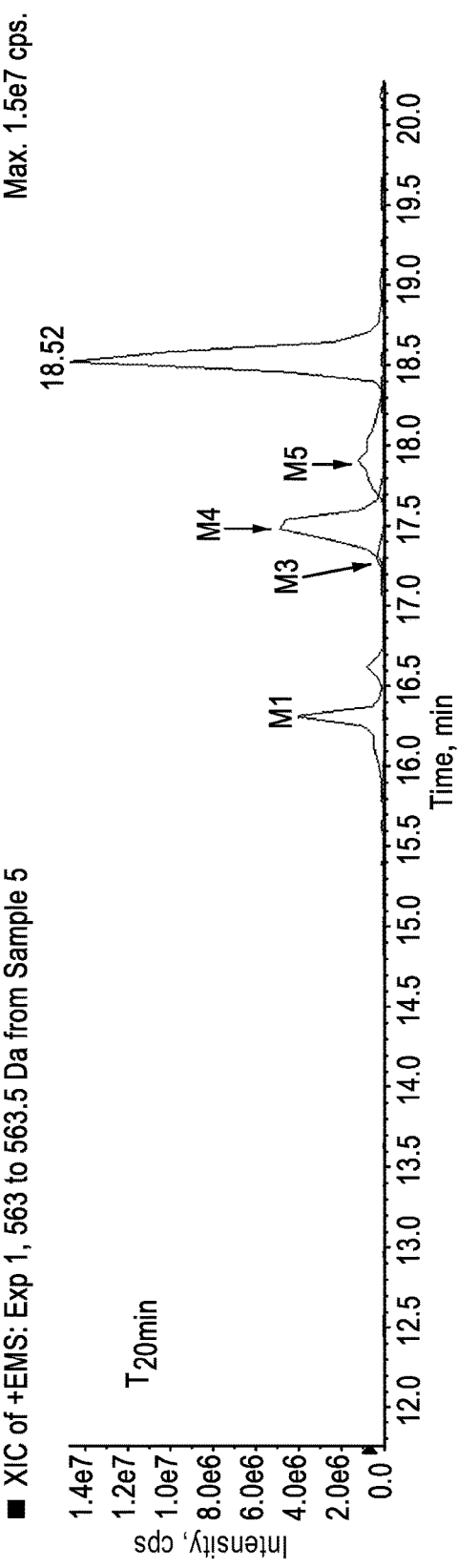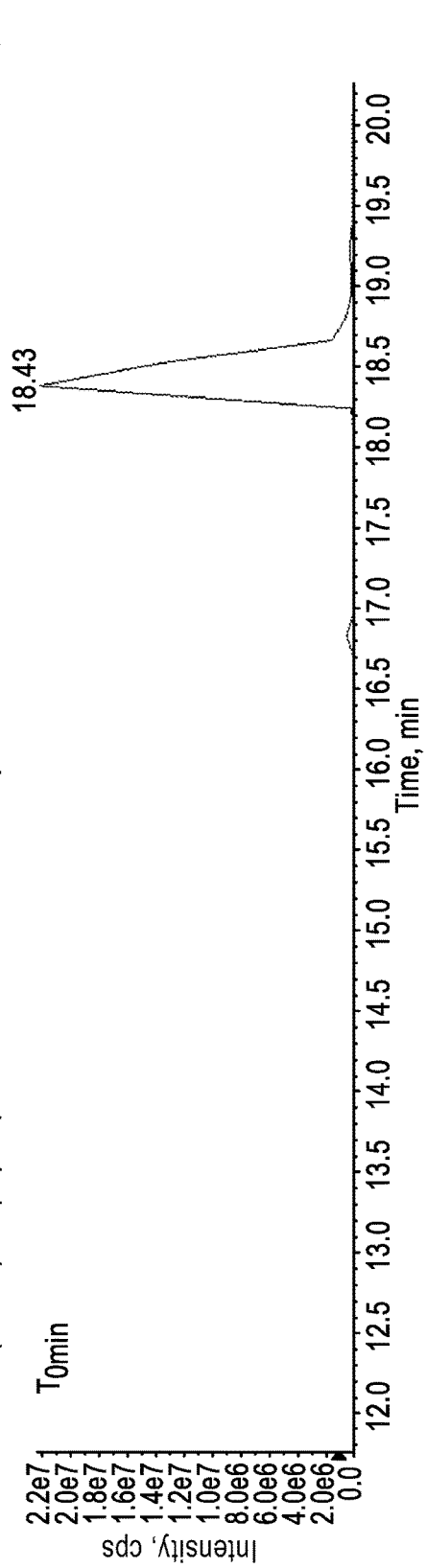

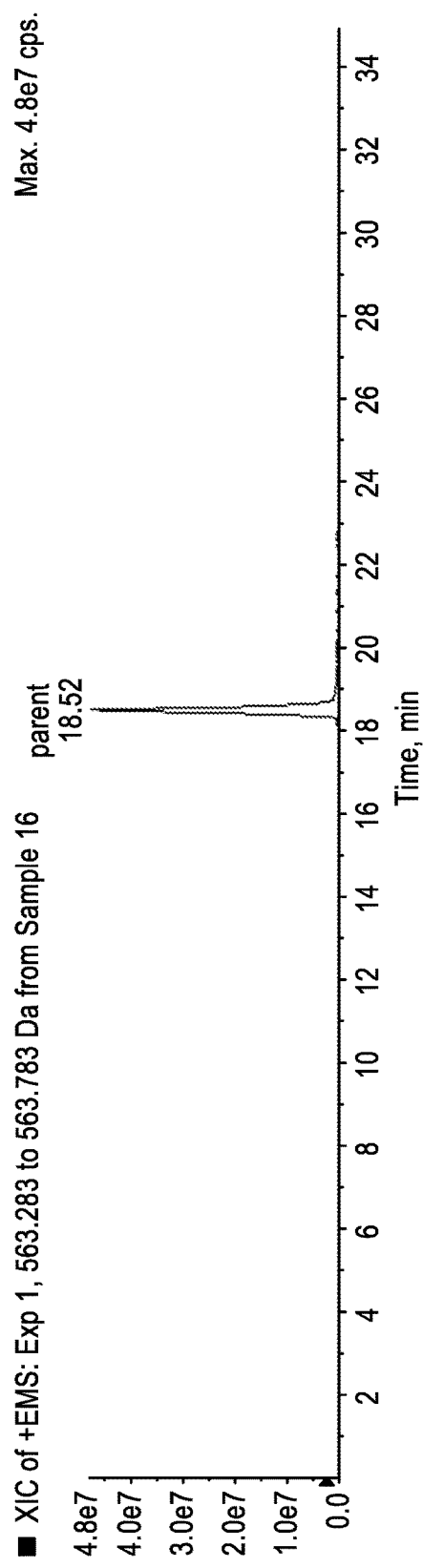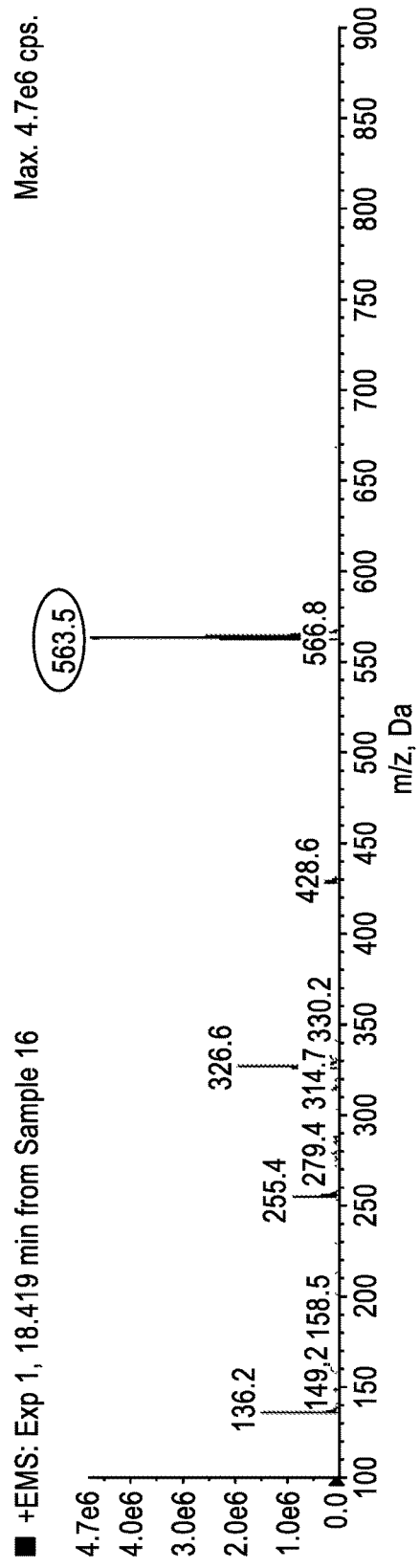
Fig. 6A
Fig. 6B

SUBSTITUTED PURINE COMPOUNDS

RELATED APPLICATIONS

This application is a continuation application of U.S. application Ser. No. 14/902,150, filed on Dec. 30, 2015, now allowed and to be issued as U.S. Pat. No. 9,688,714 on Jun. 27, 2017, which is a U.S. National Phase application, filed under 35 U.S.C. § 371, of International Application No. PCT/US2014/045406, filed Jul. 3, 2014, which claims priority to, and the benefit of, U.S. provisional application No. 61/842,701, filed Jul. 3, 2013, the entire contents of each of which are incorporated herein by reference in their entireties.

BACKGROUND OF THE INVENTION

Disease-associated chromatin-modifying enzymes (e.g., DOT1L) play a role in diseases and disorders such as proliferative disorders, metabolic disorders and blood disorders. Thus, there is a need for the development of small molecules that are capable of modulating the activity of DOT1L.

SUMMARY OF THE INVENTION

The invention provides substituted purine compounds, including metabolites of ((2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol) (Compound A)

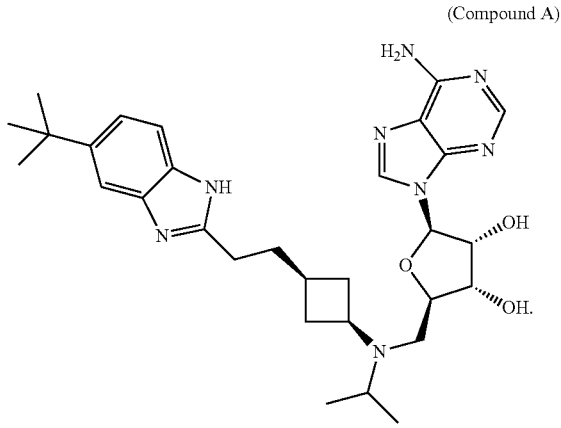 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3[nH]2)C1]

(Compound A)

The compounds disclosed herein are useful for modulating the aberrant action of epigenetic enzymes and are useful for treating a disease or disorder in which an epigenetic enzyme plays a role. The present invention also provides pharmaceutically acceptable salts, and/or esters of these compounds.

In one aspect, the present invention features a compound of Formula (I) below.

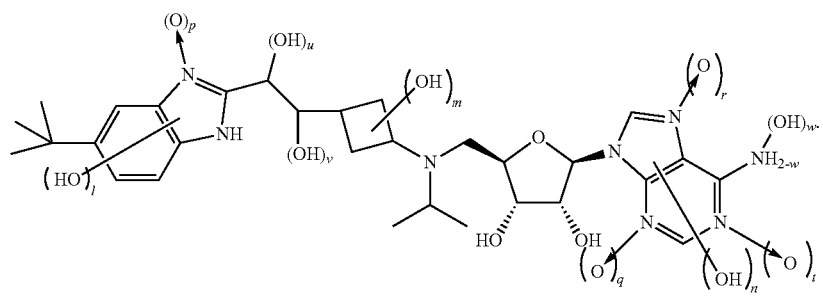

(I)

In this formula, each of l, m, and n, independently is 0, 1, or 2, each of p, q, r, t, u, v, and w, independently is 0 or 1, and the sum of l, m, n, p, q, r, t, u, v, and w is 1, 2, or 3.

One subset of the compounds of Formula (I) includes those of Formula (IA):

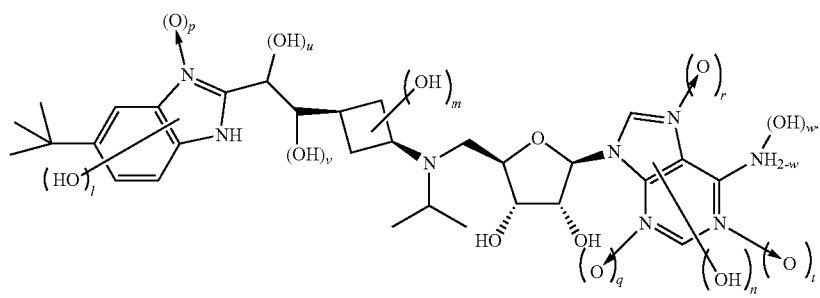

(IA)

Another subset of the compounds of Formula (I) includes those of Formula (IB):

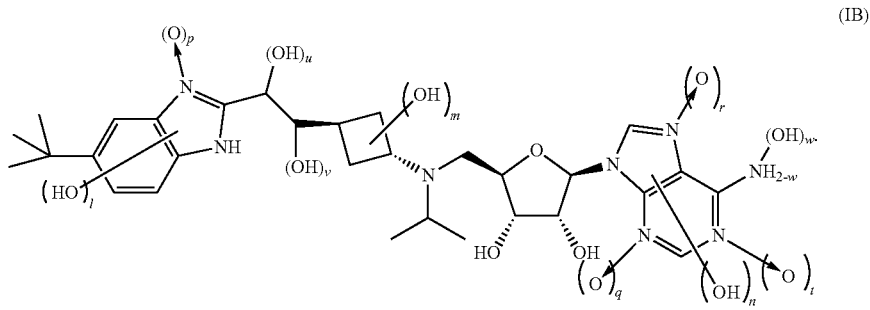

(IB)

In another aspect, the present invention features a pharmaceutically acceptable salt or ester of a compound of Formula (I), (IA), or (IB) above.

In yet another aspect, the present invention features a compound of Formula (II) below or a pharmaceutically acceptable salt or ester thereof.

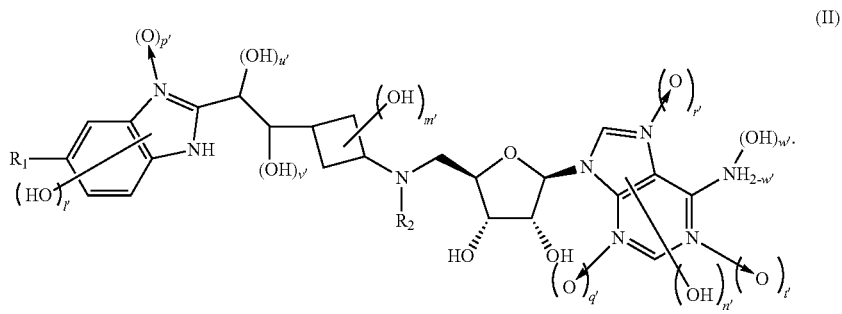

(II)

In Formula (II), $R_1$ is unsubstituted t-butyl or t-butyl substituted with one or more substituents selected from hydroxyl and oxo (i.e., =O), $R_2$ is H, hydroxyl, unsubstituted i-propyl, or i-propyl substituted with one or more hydroxyl, l' is 0, 1, 2, or 3, each of m' and n', independently is 0, 1, or 2, each of p', q', r', t', u', v', and w', independently is 0 or 1, and when $R_1$ is t-butyl substituted with only one hydroxyl, $R_2$ is H, hydroxyl, or i-propyl substituted with one or more hydroxyl, and when $R_1$ is unsubstituted t-butyl, then (i) $R_2$ is hydroxyl, or i-propyl substituted with one or more hydroxyl, or (ii) the sum of l', m', n', p', q', r', t', u', v', and w' is 1 or greater.

One subset of the compounds of Formula (II) includes those of Formula (IIA):

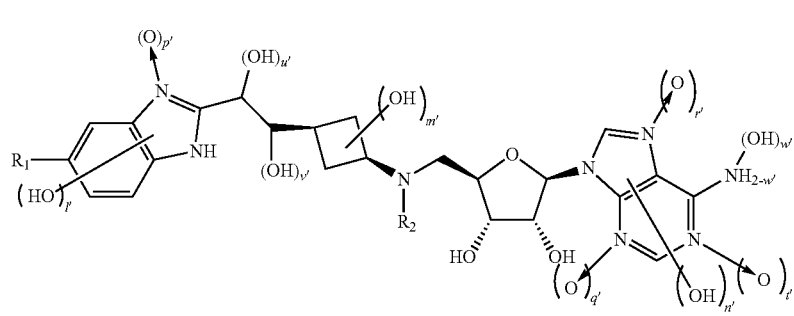

(IIA)

Another subset of the compounds of Formula (I) includes those of Formula (IIB):

(IIB)

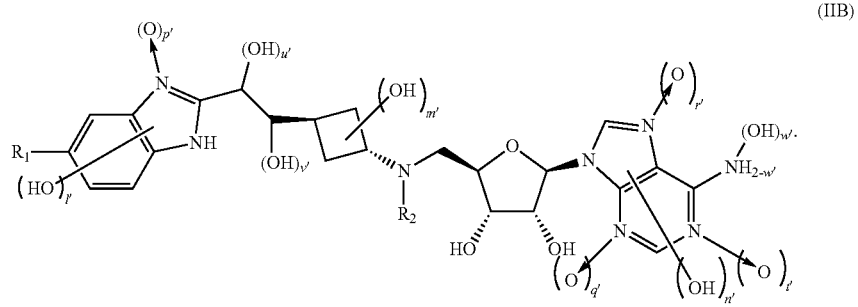

In yet another aspect, the present invention features a compound is selected from compounds 1-89, 101-104, and 107-114 and pharmaceutically acceptable salts thereof.

The invention also relates to a pharmaceutical composition of a compound of any of the Formulae described herein and a pharmaceutically acceptable carrier.

The invention also relates to a pharmaceutical composition of a salt of a compound of any of the Formulae described herein and a pharmaceutically acceptable carrier.

The invention also relates to a pharmaceutical composition of a hydrate of a compound of any of the Formulae described herein and a pharmaceutically acceptable carrier.

The present invention provides methods of treating or preventing a disease or disorder in which DOT1L plays a role such as cancer. The present invention provides methods of treating cancer. The present invention also provides methods of preventing cancer. The method includes administering to a subject in need thereof a therapeutically effective amount of the compound of any of the Formulae described herein. The cancer can be a hematological cancer. For example, the cancer is leukemia. Particularly, the cancer is acute myeloid leukemia, acute lymphocytic leukemia or mixed lineage leukemia.

The present invention provides methods of treating a disease or disorder mediated by translocation of a gene on chromosome 11q23. The present invention also provides methods of preventing a disease or disorder mediated by translocation of a gene on chromosome 11q23. The method includes administering to a subject in need thereof a therapeutically effective amount of the compound of any of the Formulae described herein.

The present invention provides methods of treating a disease or disorder in which DOT1-mediated protein methylation plays a part or a disease or disorder mediated by DOT1-mediated protein methylation. The present invention also provides methods of preventing a disease or disorder in which DOT1-mediated protein methylation plays a part or a disease or disorder mediated by DOT1-mediated protein methylation. The method includes administering to a subject in need thereof a therapeutically effective amount of the compound of any of the Formulae described herein.

The present invention provides methods of inhibiting DOT1L activity in a cell. The method includes contacting the cell with an effective amount of one or more of the compound of any of the Formulae described herein.

Still another aspect of the invention relates to a method of reducing the level of Histone H3 Lysine residue 79 (H3-K79) methylation in a cell. The method includes contacting a cell with a compound of the present invention. Such method can be used to ameliorate any condition which is caused by or potentiated by the activity of DOT1 through H3-K79 methylation.

The present invention relates to use of the compounds disclosed herein in preparation of a medicament for treating or preventing cancer. The use includes a compound of any of the Formulae described herein for administration to a subject in need thereof in a therapeutically effective amount. The cancer can be a hematological cancer. For example, the cancer is leukemia. Particularly, the cancer is acute myeloid leukemia, acute lymphocytic leukemia or mixed lineage leukemia.

The present invention provides use of the compounds disclosed herein in preparation of a medicament for treating or preventing a disease or disorder mediated by translocation of a gene on chromosome 11q23. The use includes a compound of any of the Formulae described herein for administration to a subject in need thereof in a therapeutically effective amount.

The present invention provides use of the compounds disclosed herein in preparation of a medicament for treating or preventing a disease or disorder in which DOT1-mediated protein methylation plays a part or a disease or disorder mediated by DOT1-mediated protein methylation. The use includes a compound of any of the Formulae described herein for administration to a subject in need thereof in a therapeutically effective amount.

The present invention provides use of the compounds disclosed herein for inhibiting DOT1L activity in a cell. The use includes contacting the cell with an effective amount of one or more of the compound of any of the Formulae described herein.

Still another aspect of the invention relates to a use of the compounds disclosed herein for reducing the level of Histone H3 Lysine residue 79 (H3-K79) methylation in a cell. The use includes contacting a cell with a compound of the present invention. Such use can ameliorate any condition which is caused by or potentiated by the activity of DOT1 through H3-K79 methylation.

Also, the present invention provides a method for treating or alleviating a symptom of leukemia comprising administering to a subject in need thereof a therapeutically effective amount of a compound described herein. In one aspect, the leukemia is characterized by a chromosomal rearrangement. In one aspect, the chromosomal rearrangement is chimeric fusion of mixed lineage leukemia gene (MLL) or partial tandem duplication of the MLL gene (MLL-PTD). In another aspect, the subject has an increased level of HOXA9, Fms-like tyrosine kinase 3 (FLT3), MEIS1, and/or DOT1L.

The present invention provides a method for treating or alleviating a symptom of leukemia comprising administering to a subject in need thereof a therapeutically effective amount of a compound described herein, wherein the subject has an increased level of HOXA9, FLT3, MEIS1, and/or DOT1L.

The present invention provides a method for treating or alleviating a symptom of leukemia in a subject comprising: obtaining a sample from the subject; detecting the level of HOXA9, FLT3, MEIS1, and/or DOT1L, wherein an increased level of HOXA9, FLT3, MEIS1, and/or DOT1L indicates the subject is responsive to a compound described herein; and administering to the subject a therapeutically effective amount of said compound when said subject is responsive to said compound.

The present invention provides a method for treating or alleviating a symptom of leukemia in a subject comprising: obtaining a sample from the subject; detecting the presence of a genetic lesion of MLL in the sample; and administering to the subject a therapeutically effective amount of a compound described herein when said genetic lesion is present in the sample. In one aspect, the genetic lesion is chimeric fusion of MLL or MLL-PTD.

In any of the foregoing methods, the sample is selected from bone marrow, peripheral blood cells, blood, plasma, serum, urine, saliva, a cell, or a tumor tissue.

The present invention provides a method for treating a disorder mediated by translocation, deletion and/or duplication of a gene on chromosome 11q23, comprising administering to a subject in need thereof a therapeutically effective amount of a compound described herein.

In another aspect, the invention features a method of selecting a therapy for a subject having leukemia. The method includes the steps of: detecting the presence of a partial tandem duplication of the MLL gene (MLL-PTD) in a sample from the subject; and selecting, based on the presence of the MLL-PTD, a therapy for treating leukemia. In one embodiment, the therapy includes administering to the subject a therapeutically effective amount of a compound described herein. In one embodiment, the method further includes administrating to the subject a therapeutically effective amount of a compound described herein. In one embodiment, the leukemia is characterized by partial tandem duplication of the MLL gene.

In another aspect, a method of treatment is provided for a subject in need thereof, the method comprising the steps of: detecting presence of a partial tandem duplication of the MLL gene (MLL-PTD) in a sample from the subject; and treating the subject based on the presence of MLL-PTD with a therapy that includes administering to the subject a therapeutically effective amount of a compound described herein. In one embodiment, the subject in need thereof has leukemia that is characterized by partial tandem duplication of the MLL gene.

In another aspect, the invention features a method of selecting a therapy for a subject having leukemia. The method includes the steps of: detecting the level of HOXA9, FLT3, MEIS1, and/or DOT1L in a sample from the subject; and selecting, based on the presence of the increased level of HOXA9, FLT3, MEIS1, and/or DOT1L a therapy for treating leukemia. In one embodiment, the therapy includes administering to the subject a therapeutically effective amount of a compound described herein. In one embodiment, the method further includes administrating to the subject a therapeutically effective amount of a compound described herein. In one embodiment, the leukemia is characterized by partial tandem duplication of the MLL gene. In another embodiment, the leukemia is characterized by overexpression of HOXA9, FLT3, MEIS1 and/or DOT1L.

In yet another aspect, a method of treatment is provided for a subject in need thereof, the method comprising the steps of: detecting the level of HOXA9, FLT3, MEIS1, and/or DOT1L in a sample from the subject; and treating the subject based on the presence of the increased level of HOXA9, FLT3, MEIS1, and/or DOT1L with a therapy that includes administering to the subject a therapeutically effective amount of a compound described herein. In one embodiment, the subject in need thereof has leukemia that is characterized by partial tandem duplication of the MLL gene. In another embodiment, the subject in need thereof has leukemia that is characterized by overexpression of HOXA9, FLT3, MEIS1 and/or DOT1L.

In addition, the invention provides methods of synthesizing the foregoing compounds. Following synthesis, a therapeutically effective amount of one or more of the compounds can be formulated with a pharmaceutically acceptable carrier for administration to a mammal, particularly humans, for use in modulating an epigenetic enzyme. In certain embodiments, the compounds of the present invention are useful for treating, preventing, or reducing the risk of cancer or for the manufacture of a medicament for treating, preventing, or reducing the risk of cancer. Accordingly, the compounds or the formulations can be administered, for example, via oral, parenteral, otic, ophthalmic, nasal, or topical routes, to provide an effective amount of the compound to the mammal.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE FIGURES

FIG. 1A is a concentration vs. time profile of plasma concentrations (mean±SD (n=3)) following IV bolus (5 mg/kg) administration to CD-1 mice (all formulated in 10% ethanol:90% saline). FIG. 1B is a concentration vs. time profile of plasma concentrations (mean±SD (n=3)) following IV bolus (1 mg/kg formulated in 0.4% HPBCD in saline) administration to SD rats. FIG. 1C is a concentration vs. time profile of plasma concentrations (mean±SD (n=3)) following IV bolus (1 mg/kg formulated in 10% ethanol: 90% saline) administration to male Beagle dogs.

FIGS. 3A-3C are representative allometric plots for Compound A using mouse, rat and dog PK data plotted with line of best fit: (A) unbound clearance ("CL") vs. bodyweight ($R^2$=0.9992); (B) product term of CL and maximum life potential ("MLP") vs. bodyweight ($R^2$=0.9993); (C) steady-state volume of distribution ("VDss") vs. bodyweight ($R^2$=0.9999).

FIGS. 5A and 5B are representative HPLC-MS chromatograms for t=20 min and t=0 min incubations, respectively, of Compound A in mouse liver microsomes supplemented with NADPH and UDPGA.

FIGS. 6A-6D are respectively LC-MS chromatogram, MS1 and MS2 spectra, and a scheme of proposed fragmentation pathways of Compound A.

DETAILED DESCRIPTION OF THE INVENTION

Figure 1A:
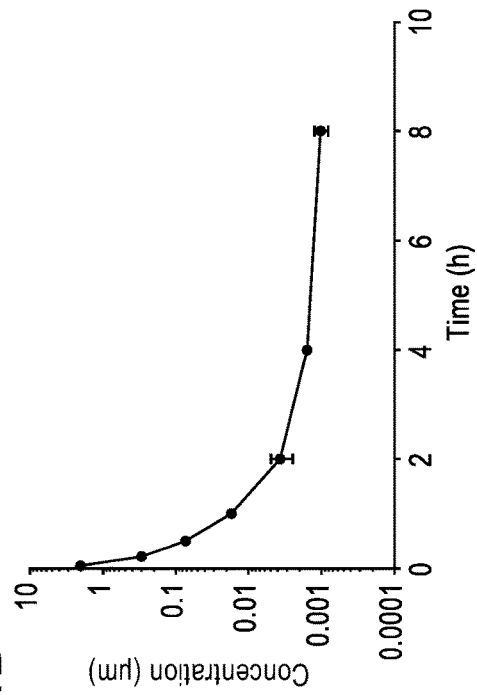
FIGS. 1A-1C are plots depicting the preclinical pharmacokinetics of Compound A as determined in mouse, rat and dog, respectively.

In one aspect, the present invention provides compounds that can be used to selectively modulate the aberrant action of an epigenetic enzyme. Further, the compounds can be used to treat or prevent a disease state in a mammal caused or mediated by aberrant action of an epigenetic enzyme. The present invention includes pharmaceutically acceptable salts, esters, and tautomers of these compounds.

The present invention provides novel substituted purine compounds, synthetic methods for making the compounds, pharmaceutical compositions containing them and various uses of the compounds.

The present invention provides the compounds of Formula (I) below or a pharmaceutically acceptable salt or ester thereof:

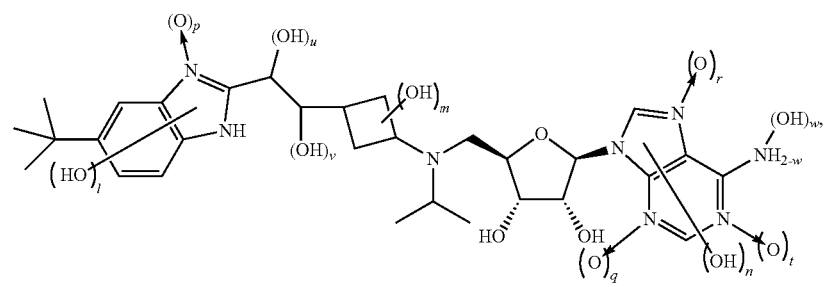

(I)

wherein each of l, m, and n, independently is 0, 1, or 2, each of p, q, r, t, u, v, and w, independently is 0 or 1, and the sum of l, m, n, p, q, r, t, u, v, and w is 1, 2, or 3.

One subset of the compounds of Formula (I) includes those of Formula (IA):

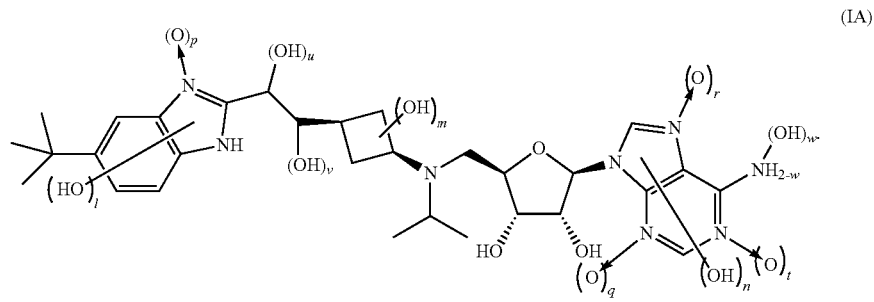

(IA)

Another subset of the compounds of Formula (I) includes those of Formula (IB):

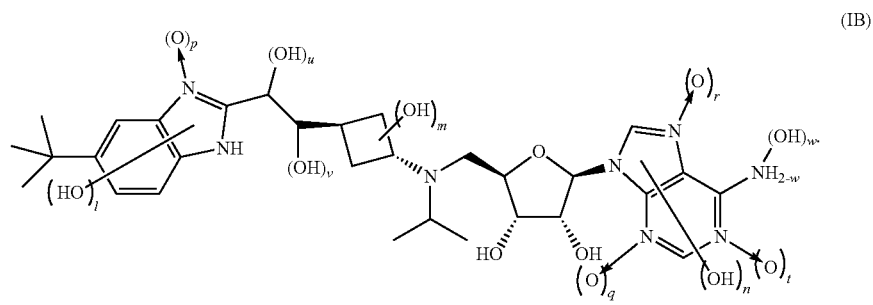

(IB)

The compounds of Formulae (I), (IA), and (IB) or pharmaceutically acceptable salts or esters thereof can include one or more of the following features:

For example, the compounds or pharmaceutically acceptable salts or esters thereof each independently are in an isolated form, e.g., a purified form.

For example, the sum of l, m, n, p, q, r, t, u, v, and w is 1, namely, the compound of Formula (I) is a monohydroxylated compound (not counting the two hydroxyls on the tetrahydrofuran ring) or a mono-N-oxide compound. For example, l is 1, and each of m, n, p, q, r, t, u, v, and w, independently is 0. For example, m is 1, and each of l, n, p, q, r, t, u, v, and w, independently is 0. For example, n is 1, and each of l, m, p, q, r, t, u, v, and w, independently is 0. For example, u is 1, and each of l, m, n, p, q, r, t, v, and w, independently is 0. For example, v is 1, and each of l, m, n, p, q, r, t, u, and w, independently is 0. For example, w is 1, and each of l, m, n, p, q, r, t, u, and v, independently is 0. For example, one of q, r, and t is 1.

For example, the sum of l, m, n, p, q, r, t, u, v, and w is 2, namely, the compound of Formula (I) is a di-hydroxylated compound (not counting the two hydroxyls on the tetrahydrofuran ring), a di-N-oxide compound, or a mono-hydroxyl-mono-N-oxide compound (not counting the two hydroxyls on the tetrahydrofuran ring).

For example, the sum of l, m, n, p, q, r, t, u, v, and w is 3, namely, the compound of Formula (I) is a tri-hydroxylated compound (not counting the two hydroxyls on the tetrahydrofuran ring), a tri-N-oxide compound, a mono-hydroxyl-di-N-oxide compound (not counting the two hydroxyls on the tetrahydrofuran ring), or a di-hydroxyl-mono-N-oxide compound (not counting the two hydroxyls on the tetrahydrofuran ring).

In yet another aspect, the present invention features a compound of Formula (II) below or a pharmaceutically acceptable salt or ester thereof:

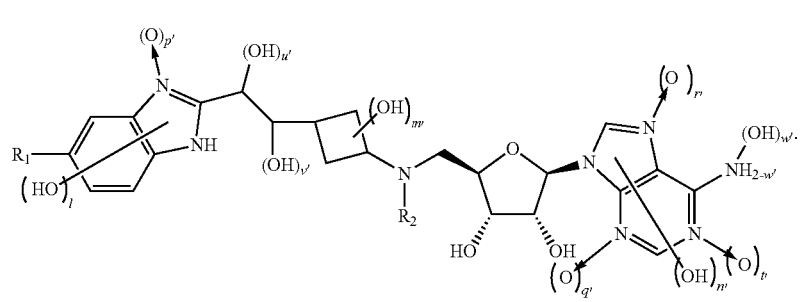

(II)

wherein $R_1$ is unsubstituted t-butyl or t-butyl substituted with one or more substituents selected from hydroxyl and oxo (i.e., =O), $R_2$ is H, hydroxyl, unsubstituted i-propyl, or i-propyl substituted with one or more hydroxyl, l' is 0, 1, 2, or 3, each of m' and n', independently is 0, 1, or 2, each of p', q', r', t', u', v', and w', independently is 0 or 1, and when $R_1$ is t-butyl substituted with only one hydroxyl, $R_2$ is H, hydroxyl, or i-propyl substituted with one or more hydroxyl, and when $R_1$ is unsubstituted t-butyl, then (i) $R_2$ is hydroxyl, or i-propyl substituted with one or more hydroxyl, or (ii) the sum of l', m', n', p', q', r', t', u', v', and w' is 1 or greater.

One subset of the compounds of Formula (II) includes those of Formula (IIA):

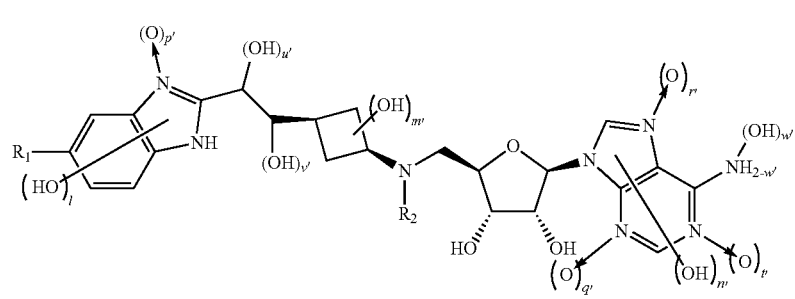

(IIA)

Another subset of the compounds of Formula (I) includes those of Formula (IIB):

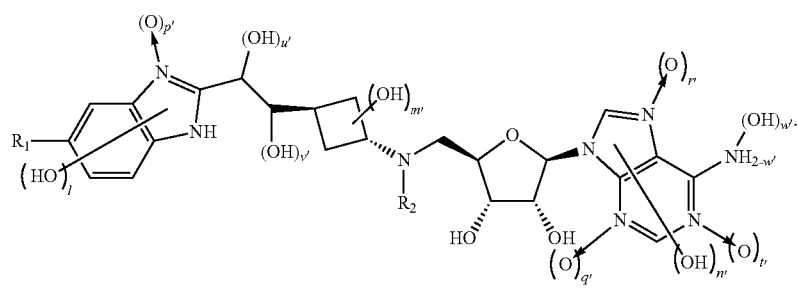

(IIB)

The compounds of Formulae (II), (IIA), and (IIB) or pharmaceutically acceptable salts or esters thereof can include one or more of the following features:

For example, the compounds or pharmaceutically acceptable salts or esters thereof each independently are in an isolated form, e.g., a purified form.

For example, the compound of Formula (II) is a mono-hydroxylated compound (not counting the two hydroxyls on the tetrahydrofuran ring). For example, $R_1$ is unsubstituted t-butyl, and (i) $R_2$ is hydroxyl or i-propyl substituted with one hydroxyl, and each of l', m', n', u', v', and w' is 0, or (ii) $R_2$ is H or unsubstituted i-propyl, one of l', m', n', u', v', and w' is 1 and the other five are each 0. For example, $R_1$ is t-butyl substituted with only one hydroxyl, and $R_2$ is H, and each of l', m', n', u', v', and w' is 0. For example, each of p', q', r', and t', independently is 0 or 1.

For example, the compound of Formula (II) is a carboxylic acid. For example, $R_1$ is t-butyl substituted with only one hydroxyl and one oxo, for example, the hydroxyl and oxo together with the carbon to which they are attached form —COOH). For example, $R_1$ is —C(CH$_3$)$_2$COOH) and $R_2$ is H or unsubstituted i-propyl, and each of l', m', n', u', v', and w' is 0. For example, each of p', q', r', and t', independently is 0 or 1.

For example, the compound of Formula (II) is a di-hydroxylated or tri-hydroxylated compound (not counting the two hydroxyls on the tetrahydrofuran ring). For example, $R_1$ is t-butyl substituted with only one hydroxyl, and (i) $R_2$ is hydroxyl or i-propyl substituted with one or two hydroxyl, and each of l', m', n', u', v', and w' is 0, or (ii) $R_2$ is H, hydroxyl, or i-propyl optionally substituted with one hydroxyl, one of l', m', n', u', v', and w' is 1 and the other five are each 0. For example, $R_1$ is t-butyl substituted with two hydroxyl, and (i) $R_2$ is H, hydroxyl or i-propyl optionally substituted with one hydroxyl, and each of l', m', n', u', v', and w' is 0, or (ii) $R_2$ is H, hydroxyl or i-propyl optionally substituted with one hydroxyl, one of l', m', n', u', v', and w' is 1 and the other five are each 0. For example, $R_1$ is t-butyl substituted with three hydroxyl, $R_2$ is H or unsubstituted i-propyl, each of l', m', n', u', v', and w' is 0. For example, each of p', q', r', and t', independently is 0 or 1.

For example, the compound of Formula (II) is a tetra-hydroxylated compound (not counting the two hydroxyls on the tetrahydrofuran ring).

For example, the compound of Formula (II) is a compound having five or more hydroxyls (not including the two hydroxyls on the tetrahydrofuran ring).

Unless otherwise specified, the term "Formula (I) or (II)" used herewith refers to any of Formulae (I), (IA), (IB), (II), (IIA) and (IIB).

In one aspect, the present invention features a compound that is selected from those listed in Table 1, i.e., compounds 1-89, and pharmaceutically acceptable salts thereof.

In one aspect, the present invention features a compound that is selected from compounds 101-104, and 107-114 listed in Table 2, and pharmaceutically acceptable salts thereof.

This invention also provides a pharmaceutical composition comprising a compound of any of the Formulae described herein and a pharmaceutically acceptable carrier.

One aspect of the present invention is based in part upon the surprising discovery that DOT1L inhibitors can effectively treat leukemia that is characterized by partial tandem duplication of the MLL gene. Another aspect of the present invention is based in part upon the surprising discovery that DOT1L inhibitors can effectively treat leukemia that is characterized by overexpression of HOXA9, FLT3, MEIS1 and/or DOT1L. Specifically, tumors or tumor cells having increased mRNA or protein level of at least one protein selected from the group consisting of HOXA9, FLT3, MEIS1 and DOT1L are sensitive to the DOT1L inhibitors of the present invention. Accordingly, the present invention provides methods of treating or alleviating a symptom of leukemia in a subject by administering a therapeutically effective amount of a DOT1L inhibitor described herein to the subject, particular leukemia associated with overexpression of at least one protein selected from the group consisting of HOXA9, FLT3, MEIS1 and DOT1L.

The compounds of the present invention inhibit the histone methyltransferase activity of DOT1L or a mutant thereof. Based upon the surprising discovery that methylation regulation by DOT1L involves in tumor formation, particular tumors bearing an increased mRNA, protein and/or activity (function) level of at least one protein selected from the group consisting of HOXA9, FLT3, MEIS1 and DOT1L, the compounds described herein are suitable candidates for treating cancers, i.e., to decrease methylation or restore methylation to roughly its level in counterpart normal cells.

The present invention features a method for treating or alleviating a symptom of cancer. The method includes administering to a subject in need thereof, a therapeutically effective amount of a compound of the present invention, or a pharmaceutically acceptable salt, prodrug, metabolite, polymorph, solvate, or stereoisomeror thereof.

The present invention provides methods for the treatment of a cancer mediated by DOT1 (e.g., DOT1L)-mediated protein methylation in a subject in need thereof by administering to a subject in need of such treatment, a therapeutically effective amount of a compound of the present invention, or a pharmaceutically acceptable salt, prodrug, metabolite, polymorph or solvate thereof. The present invention further provides the use of a compound of the present invention, or a pharmaceutically acceptable salt, prodrug, metabolite, polymorph or solvate thereof, for the preparation of a medicament useful for the treatment of a cancer mediated by DOT1L-mediated protein methylation.

The present invention provides methods for the treatment of a cancer the course of which is influenced by modulating the methylation status of histones or other proteins, wherein said methylation status is mediated at least in part by the activity of DOT1L. Modulation of the methylation status of histones can in turn influence the level of expression of target genes activated by methylation, and/or target genes suppressed by methylation. The method includes administering to a subject in need of such treatment, a therapeutically effective amount of a compound of the present invention, or a pharmaceutically acceptable salt, prodrug, metabolite, polymorph, solvate, or stereoisomeror thereof.

The present invention also provides methods of protecting against or preventing a cancer in which DOT1L-mediated protein methylation plays a part in a subject in need thereof by administering a therapeutically effective amount of compound of the present invention, or a pharmaceutically acceptable salt, prodrug, metabolite, polymorph or solvate thereof, to a subject in need of such treatment. The present invention also provides the use of compound of the present invention, or a pharmaceutically acceptable salt, prodrug, metabolite, polymorph, solvate, or stereoisomeror thereof, for the preparation of a medicament useful for the prevention of a cell proliferative disorder.

In one aspect, the cancer is a cancer selected from the group consisting of brain and CNS cancer, kidney cancer, ovarian cancer, pancreatic cancer, lung cancer, breast cancer, colon cancer, prostate cancer, or a hematological cancer. For example, the hematological cancer is leukemia or lymphoma. Preferably the cancer is leukemia.

The present invention further provides the use of a compound of the present invention, or a pharmaceutically acceptable salt, ester, prodrug, metabolite, polymorph or solvate thereof in the treatment of leukemia, or, for the preparation of a medicament useful for the treatment of such leukemia. The leukemia can be acute or chronic leukemia. Preferably, the leukemia is acute myeloid leukemia, acute lymphocytic leukemia or mixed lineage leukemia. Exemplary leukemia that may be treated is mixed linage leukemia (MLL). Preferably, the MLL that can be treated by the compound of the present invention is chimeric fusion of MLL, partial tandem duplication of the MLL gene (MLL-PTD) or non-rearranged MLL.

Mixed lineage leukemia (MLL) is a genetically distinct form of acute leukemia that constitutes over 70% of infant leukemias and approximately 10% of adult acute myeloid leukemias (AML) (Hess, J. L. (2004), Trends Mol Med 10, 500-507; Krivtsov, A. V., and Armstrong, S. A. (2007), Nat Rev Cancer 7, 823-833). MLL represents a particularly aggressive form of leukemia and patients with this disease generally have poor prognoses; these patients often suffer from early relapse after treatment with current chemotherapies. There is thus a great and present need for new treatment modalities for patients suffering with MLL.

A universal hallmark of MLL disease is a chromosomal translocation affecting the MLL gene on chromosome 11q23 (Hess, 2004; Krivtsov and Armstrong, 2007). Normally, the MLL gene encodes for a SET-domain histone methyltransferase that catalyzes the methylation of lysine 4 of histone H3 (H3K4) at specific gene loci (Milne et al. (2002) Mol Cell 10, 1107-1117; Nakamura et al. (2002), Mol Cell 10, 1119-1128). Gene localization is conferred by specific interactions with recognition elements within MLL, external to the SET-domain (Ayton et al. (2004) Mol Cell Biol 24, 10470-10478; Slany et al., (1998) Mol Cell Biol 18, 122-129; Zeleznik-Le et al. (1994) Proc Natl Acad Sci USA 91, 10610-10614). In the disease-linked translocations, the catalytic SET-domain is lost and the remaining MLL protein is fused to a variety of partners, including members of the AF and ENL family of proteins such as AF4, AF9, AF10 and ENL (Hess, 2004; Krivtsov and Armstrong, 2007; Slany (2009) Haematologica 94, 984-993). These fusion partners are capable of interacting directly, or indirectly, with another histone methyltransferase, DOT1L (Bitoun et al. (2007) Hum Mol Genet 16, 92-106; Mohan et al. (2010) Genes Dev. 24, 574-589; Mueller et al. (2007) Blood 110, 4445-4454; Mueller et al. (2009) PLoS Biol 7, e1000249; Okada et al. (2005) Cell 121, 167-178; Park et al. (2010) Protein J 29, 213-223; Yokoyama et al. (2010) Cancer Cell 17, 198-212; Zhang et al. (2006) J Biol Chem 281, 18059-18068). As a result, translocation products retain gene-specific recognition elements within the remainder of the MLL protein, but also gain the ability to recruit DOT1L, to these locations (Monroe et al. (2010) Exp Hematol. 2010 Sep. 18. [Epub ahead of print] Pubmed PMID: 20854876; Mueller et al., 2007; Mueller et al., 2009; Okada et al., 2005). DOT1L catalyzes the methylation of H3K79, a chromatin modification associated with actively transcribed genes (Feng et al. (2002) Curr Biol 12, 1052-1058; Steger et al. (2008) Mol Cell Biol 28, 2825-2839). The ectopic H3K79 methylation that results from MLL fusion protein recruitment of DOT1L leads to enhanced expression of leukemogenic genes, including HOXA9 and MEIS1 (Guenther et al. (2008) Genes & Development 22, 3403-3408; Krivtsov et al. (2008) Nat Rev Cancer 7, 823-833; Milne et al. (2005) Cancer Res 65, 11367-11374; Monroe et al., 2010; Mueller et al., 2009; Okada et al., 2005; Thiel et al. (2010) Cancer Cell 17, 148-159). Hence, while DOT1L is not genetically altered in the disease per se, its mislocated enzymatic activity is a direct consequence of the chromosomal translocation affecting MLL patients; thus, DOT1L has been proposed to be a catalytic driver of leukemogenesis in this disease (Krivtsov et al., 2008; Monroe et al., 2010; Okada et al., 2005; Yokoyama et al. (2010) Cancer Cell 17, 198-212). Further support for a pathogenic role of DOT1L in MLL comes from studies in model systems that demonstrate a requirement for DOT1L in propagating the transforming activity of MLL fusion proteins (Mueller et al., 2007; Okada et al., 2005).

Evidence indicates that the enzymatic activity of DOT1L is critical to pathogenesis in MLL and inhibition of DOT1L may provide a pharmacologic basis for therapeutic intervention in this disease. Compound treatment results in selective, concentration-dependent killing of leukemia cells bearing the MLL-translocation without effect on non-MLL transformed cells. Gene expression analysis of inhibitor treated cells shows downregulation of genes aberrantly over expressed in MLL-rearranged leukemias and similarities with gene expression changes caused by genetic knockout of the DOT1L gene in a mouse model of MLL-AF9 leukemia.

MLL can be characterized by the genetic lesions of the MLL gene. Such genetic lesions include chromosomal rearrangements, such as translocations, deletions, and/or duplications of the MLL gene. MLL has been categorized or characterized as having a chimeric fusion of MLL, partial tandem duplication of the MLL gene (MLL-PTD), or non-rearranged MLL. Chromosomal rearrangements or translocations can be identified by methods known in the art. For example, chromosomal rearrangements resulting in chimeric fusions can be detected by probe-based assays, such as FISH (fluorescence in situ hybridization) or sequence amplification by PCR. Those chromosomal rearrangements that result in partial tandem duplications are often difficult to detect by probe-based assays, and therefore, other DNA sequencing methods known in the art may be used, such as Sanger sequencing, de novo sequencing, shotgun sequencing, or next generation sequencing methods. MLL-PTD can be identified by DNA sequencing. MLL chimeric fusions can be identified by FISH. Diagnosis of MLL can be performed by detection of rearrangements of the MLL gene, or increased mRNA, protein, and/or activity level of at least one protein selected from the group consisting of HOXA9, FLT3, MEIS1 and DOT1L, as further described herein.

Compounds of the present invention can selectively inhibit proliferation of tumor or tumor cells characterized with an increased mRNA, protein and/or activity (function) level of at least one protein selected from the group consisting of HOXA9, FLT3, MEIS1 and DOT1L.

Accordingly, the present invention provides methods for treating or alleviating a symptom of leukemia characterized with an increased mRNA, protein and/or activity (function) level of at least one protein selected from the group consisting of HOXA9, FLT3, MEIS1 and DOT1L by a compound of the present invention, or a pharmaceutically acceptable salt, ester, prodrug, metabolite, polymorph or solvate thereof. Exemplary leukemia that may be treated is mixed linage leukemia (MLL). Preferably, MLL that can be treated by the compound of the present invention is chimeric fusion of MLL, partial tandem duplication of MLL (MLL-PTD) or nonrearranged MLL.

The present invention also provides methods for treating or alleviating a symptom of leukemia characterized by the presence of a genetic lesion of MLL. For example, this method comprises obtaining sample from the subject; detecting the presence of a genetic lesion of MLL in the sample; and when the genetic lesion is present in the sample, administering to the subject a therapeutically effective amount of a DOT1L inhibitor (i.e., a compound selected from compounds 1-89, 101-104, and 107-114 and pharmaceutically acceptable salts thereof). The genetic lesion is chimeric fusion of MLL or MLL-PTD.

The present invention also provides methods for treating a disorder medicated by translocation, deletion and/or duplication of a gene on chromosome 11q23, comprising administering to a subject in need thereof a therapeutically effective amount of a compound selected from compounds 1-89, 101-104, and 107-114 and pharmaceutically acceptable salts thereof.

In other aspects, the present invention provides personalized medicine, treatment and/or cancer management for a subject by genetic screening of increased gene expression (mRNA or protein), and/or increased function or activity level of at least one protein selected from the group consisting of HOXA9, FLT3, MEIS1 and DOT1L in the subject. For example, the present invention provides methods for treating, preventing or alleviating a symptom of cancer or a precancerous condition by determining responsiveness of the subject to a DOT1L inhibitor and when the subject is responsive to the DOT1L inhibitor, administering to the subject a therapeutically effective amount of the DOT1L inhibitor, or a pharmaceutically acceptable salt, prodrug, metabolite, polymorph, solvate, or stereoisomeror thereof. The responsiveness is determined by obtaining a sample from the subject and detecting increased mRNA or protein, and/or increased activity level of at least one protein selected from the group consisting of HOXA9, FLT3, MEIS1 and DOT1L, and the presence of such gain of expression and/or function indicates that the subject is responsive to the DOT1L inhibitor. Once the responsiveness of a subject is determined, a therapeutically effective amount of a DOT1L inhibitor, for example, any compound selected from compounds 1-89, 101-104, and 107-114 and pharmaceutically acceptable salts thereof, can be administered. The therapeutically effective amount of a DOT1L inhibitor can be determined by one of ordinary skill in the art.

As used herein, the term "responsiveness" is interchangeable with terms "responsive", "sensitive", and "sensitivity", and it is meant that a subject is showing therapeutic responses when administered an DOT1L inhibitor, e.g., tumor cells or tumor tissues of the subject undergo apoptosis and/or necrosis, and/or display reduced growing, dividing, or proliferation. This term is also meant that a subject will or has a higher probability, relative to the population at large, of showing therapeutic responses when administered an DOT1L inhibitor, e.g., tumor cells or tumor tissues of the subject undergo apoptosis and/or necrosis, and/or display reduced growing, dividing, or proliferation.

As used herein, a "subject" is interchangeable with a "subject in need thereof", both of which refers to a subject having a disorder in which DOT1L-mediated protein methylation plays a part, or a subject having an increased risk of developing such disorder relative to the population at large. A subject in need thereof may be a subject having a disorder associated DOT1L. A subject in need thereof can have a precancerous condition. Preferably, a subject in need thereof has cancer. A subject in need thereof can have cancer associated with DOT1L. A subject in need thereof can have cancer associated with increased expression (mRNA or protein) and/or activity level of at least one protein selected from the group consisting of HOXA9, FLT3, MEIS1 and DOT1L. In a preferred aspect, a subject in need thereof has one or more cancers selected from the group consisting of brain and central nervous system (CNS) cancer, head and neck cancer, kidney cancer, ovarian cancer, pancreatic cancer, leukemia, lung cancer, lymphoma, myeloma, sarcoma, breast cancer, prostate cancer and a hematological cancer. Preferably, a subject in need thereof has a hematologic cancer, wherein the hematologic cancer is leukemia or lymphoma. Exemplary leukemia is MLL. Other hematologic cancers of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

As used herein, a "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject can be male or female.

A subject in need thereof can be one who has been previously diagnosed or identified as having cancer or a precancerous condition. A subject in need thereof can also be one who is having (suffering from) cancer or a precancerous condition. Alternatively, a subject in need thereof can be one who is having an increased risk of developing such disorder relative to the population at large (i.e., a subject who is predisposed to developing such disorder relative to the population at large).

Optionally a subject in need thereof has already undergone, is undergoing or will undergo, at least one therapeutic intervention for the cancer or precancerous condition.

A subject in need thereof may have refractory cancer on most recent therapy. "Refractory cancer" means cancer that does not respond to treatment. The cancer may be resistant at the beginning of treatment or it may become resistant during treatment. Refractory cancer is also called resistant cancer. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy.

In some embodiments, a subject in need thereof may have a secondary cancer as a result of a previous therapy. "Secondary cancer" means cancer that arises due to or as a result from previous carcinogenic therapies, such as chemotherapy. In some embodiments, the secondary cancer is a hematologic cancer, such as leukemia.

In any method of the present invention, a subject in need thereof may have increased mRNA, protein, and/or activity level of at least of at least one signaling component downstream of at least one protein selected from the group consisting of HOXA9, FLT3, MEIS1 and DOT1L. Such downstream components are readily known in the art, and can include other transcription factors, or signaling proteins.

As used herein, the term "increase in activity" refers to increased or a gain of function of a gene product/protein compared to the wild type. In one aspect of the present invention, increased activity can be caused by increased mRNA and/or increased protein levels.

Increased mRNA levels can be caused by gene amplification and increased transcription, for example. Increased protein levels can be caused by increased stability, inhibition of degradation pathways, or increased transcription. Alternatively, increased activity levels can be caused by a gain of function mutation resulting from a point mutation (e.g., a substitution, a missense mutation, or a nonsense mutation), an insertion, and/or a deletion, or a rearrangement in a polypeptide selected from the group consisting of HOXA9, FLT3, MEIS1 and DOT1L, or a nucleic acid sequence encoding a polypeptide selected from the group consisting of HOXA9, FLT3, MEIS1 and DOT1L. The mutations referred herein are somatic mutations. The term "somatic mutation" refers to a deleterious alteration in at least one gene allele that is not found in every cell of the body, but is found only in isolated cells. A characteristic of the somatic mutations as used herein is, that they are restricted to particular tissues or even parts of tissues or cells within a tissue and are not present in the whole organism harboring the tissues or cells. The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene.

Accordingly, an increase in mRNA or protein expression and/or activity levels can be detected using any suitable method available in the art. For example, an increase in activity level can be detected by measuring the biological function of a gene product, such as the histone methyltransferase activity of DOT1L (i.e., methylation of histone substrates such as H3K79 by immunoblot); transcriptional activity of HOXA9 or MEIS1 (i.e., expression levels of HOXA9 or MEIS1 target genes by RT-PCR); or phosphorylation activity of FLT3 (i.e., phosphorylation status of FLT3 targets by immunoblot or radioimmunoassay). Alternatively, a gain of function mutation can be determined by detecting any alternation in a nucleic acid sequence encoding a protein selected from the group consisting of HOXA9, FLT3, MEIS1 and DOT1L. For example, a nucleic acid sequence encoding HOXA9, FLT3, MEIS1 and DOT1L having a gain of function mutation can be detected by whole-genome resequencing or target region resequencing (the latter also known as targeted resequencing) using suitably selected sources of DNA and polymerase chain reaction (PCR) primers in accordance with methods well known in the art. The method typically and generally entails the steps of genomic DNA purification, PCR amplification to amplify the region of interest, cycle sequencing, sequencing reaction cleanup, capillary electrophoresis, and/or data analysis. Alternatively or in addition, the method may include the use of microarray-based targeted region genomic DNA capture and/or sequencing. Kits, reagents, and methods for selecting appropriate PCR primers and performing resequencing are commercially available, for example, from Applied Biosystems, Agilent, and NimbleGen (Roche Diagnostics GmbH). Detection of mRNA expression can be detected by methods known in the art, such as Northern blot, nucleic acid PCR, and quantitative RT-PCR. Detection of polypeptide expression (i.e., wild-type or mutant) can be carried out with any suitable immunoassay in the art, such as Western blot analysis.

By "sample" it means any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

The present invention also provides methods for diagnosing leukemia in a subject by obtaining a sample from the subject and detecting an increased mRNA, protein and/or activity level of at least one protein selected from the group consisting of HOXA9, FLT3, MEIS1 and DOT1L, and the presence of such increased mRNA, protein and/or activity level indicates that the subject has or is at risk for developing leukemia compared to a subject without such increased mRNA, protein and/or activity level, or a subject that does not have leukemia.

The present invention also provides methods for determining predisposition of a subject to leukemia by obtaining a sample from the subject and detecting an increased mRNA, protein and/or activity level of at least one protein selected from the group consisting of HOXA9, FLT3, MEIS1 and DOT1L, and the presence of such increased mRNA, protein and/or activity level indicates that the subject is predisposed to (i.e., having higher risk of) developing leukemia compared to a subject without such increased mRNA, protein and/or activity level.

The term "predisposed" as used herein in relation to cancer or a precancerous condition is to be understood to mean the increased probability (e.g., at least 1%, 5%, 10%, 20%, 30%, 40%, 50%, 60%, 70%, 80%, 90%, 100%, 150%, 200%, or more increase in probability) that a subject with an increased mRNA, protein and/or activity level of at least one protein selected from the group consisting of HOXA9, FLT3, MEIS1 and DOT1L, will suffer leukemia, as compared to the probability that another subject not having an increased mRNA, protein and/or activity level of at least one protein selected from the group consisting of HOXA9, FLT3, MEIS1 and DOT1L, will suffer leukemia, under circumstances where other risk factors (e.g., chemical/environment, food, and smoking history, etc.) for having leukemia between the subjects are the same.

"Risk" in the context of the present invention, relates to the probability that an event will occur over a specific time period and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion.

In other example, the present invention provides methods of cancer management in a subject by determining predisposition of the subject to a cancer or a precancerous condition periodically. The methods comprise steps of obtaining a sample from the subject and detecting increased mRNA or protein, and/or increased activity level of at least one protein selected from the group consisting of HOXA9, FLT3, MEIS1 and DOT1L, and the presence of such gain of expression and/or function indicates that the subject is predisposed to developing the cancer or the precancerous condition compared to a subject without such gain of mRNA or protein expression and/or function of the at least one protein selected from the group consisting of HOXA9, FLT3, MEIS1 and DOT1L.

Any compounds (e.g., DOT1L inhibitor) of the present invention can be used for the methods described above.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue.

A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute lymphocytic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. Preferably, compositions of the present invention may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

Preferably, compound of the present invention, or a pharmaceutically acceptable salt, prodrug, metabolite, polymorph, or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, prodrug, metabolite, polymorph or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, prodrug, metabolite, polymorph or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

For example, an in vitro biological assay that can be used includes the steps of (1) mixing a histone substrate (e.g., an isolated histone sample for a histone or modified histone of interest, or an isolated oligonucleosome substrate) with recombinant DOT1L enzyme (e.g., recombinant protein containing amino acids 1-416); (2) adding a candidate compound of the invention to this mixture; (3) adding non-radioactive and $^3$H-labeled S-Adenosyl methionine (SAM) to start the reaction; (4) adding excessive amount of non-radioactive SAM to stop the reaction; (4) washing off the free non-incorporated $^3$H-SAM; and (5) detecting the quantity of $^3$H-labeled histone substrate by any methods known in the art (e.g., by a PerkinElmer TopCount platereader).

For example, an in vitro cell viability assay that can be used includes the steps of (1) culturing cells (e.g., EOL-1 cells) in the presence of increasing concentration of a candidate compound; (2) determining viable cell number every 3-4 days by methods known in the art (e.g., using the Millipore Guava Viacount assay); (3) plotting concentration-dependence growth curves; and optionally (4) calculating $IC_{50}$ values from the concentration-dependence growth curves using methods known in the art (e.g., using GraphPad Prism Software).

For example, a histone methylation assay that can be used includes the steps of (1) culturing cells (e.g., EOL-1 cells) in the presence of a candidate compound; (2) harvesting the cells; (3) extracting histone proteins, using methods known in the art (e.g., sulfuric acid precipitation); (4) fractionating histone extracts by SDS-PAGE electrophoresis and transferring to a filter; (5) probing the filter with antibodies specific to a protein or methylated-protein of interest (e.g., H3K79me2-specific antibody and total histone H3-specific antibody); and (6) detecting the signal of the antibodies using methods known in the art (e.g., Li-cor Odyssey infrared imager).

For example, a gene expression assay that can be used includes the steps of (1) culturing cells (e.g., EOL-1, Molm13, MV411, LOUCY, SemK2, Reh, HL60, BV173, or Jurkat cells) in the presence or absence of a candidate compound; (2) harvesting the cells; (3) extracting the RNA using methods known in the art (e.g., Qiagen RNeasy Kit); (4) synthesizing cDNA from the extracted RNA (e.g., Applied Biosystems reverse transcriptase kit); (5) preparing qPCR reactions using, for example, primers and probes (e.g., predesigned labeled primer and probe sets for HOXA9, MEIS1, FLT3, DOT1L, and β2-microglobulin from Applied Biosystems), synthesized sample cDNA, and qPCR master mix reagent (e.g., Applied Biosystems Taqman universal PCR master mix); (6) running samples on PCR machine (e.g., Applied Biosystems); (7) analysis of the data and calculation of relative gene expression.

As used herein, "monotherapy" refers to the administration of a single active or therapeutic compound to a subject in need thereof. Preferably, monotherapy will involve administration of a therapeutically effective amount of a single active compound. For example, cancer monotherapy with one of the compound of the present invention, or a pharmaceutically acceptable salt, prodrug, metabolite, analog or derivative thereof, to a subject in need of treatment of cancer. In one aspect, the single active compound is a compound of the present invention, or a pharmaceutically acceptable salt, prodrug, metabolite, polymorph or solvate thereof.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer.

Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, prodrug, metabolite, polymorph or solvate thereof, acts selectively on a cancer or precancerous cell but not on a normal cell. Preferably, a compound of the present invention, or a pharmaceutically acceptable salt, prodrug, metabolite, polymorph or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention, or a pharmaceutically acceptable salt, prodrug, metabolite, polymorph or solvate thereof, can modulate the activity of a molecular target (e.g., a target protein methyltransferase). Modulating refers to stimulating or inhibiting an activity of a molecular target. Preferably, a compound of the present invention, or a pharmaceutically acceptable salt, prodrug, metabolite, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, prodrug, metabolite, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, prodrug, metabolite, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention, or a pharmaceutically acceptable salt, prodrug, metabolite, polymorph or solvate thereof, demonstrates a minimum of a fourfold differential, preferably a tenfold differential, more preferably a fifty fold differential, in the dosage required to achieve a biological effect. Preferably, a compound of the present invention, or a pharmaceutically acceptable salt, prodrug, metabolite, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of a protein methyltransferase of interest.

The present invention provides methods to assess biological activity of a compound of the present invention, or a pharmaceutically acceptable salt, prodrug, metabolite, polymorph or solvate thereof or methods of identifying a test compound as a modulator (e.g., an inhibitor) of DOT1L. DOT1L polypeptides and nucleic acids can be used to screen for compounds that bind to and/or modulate (e.g., increase or decrease) one or more biological activities of DOT1L, including but not limited to H3K79 HMTase activity, SAM binding activity, histone and/or nucleosome binding activity, AF10 binding activity, AF10-MLL or other MLL fusion protein binding activity, and/or any other biological activity of interest. A DOT1L polypeptide can be a functional fragment of a full-length DOT1L polypeptide or functional equivalent thereof, and may comprise any DOT1 domain of interest, including but not limited to the catalytic domain, the SAM binding domain and/or the positively charged domain, the AF10 interaction domain and/or a nuclear export signal.

Methods of assessing DOT1L binding to histones, nucleosomes, nucleic acids or polypeptides can be carried out using standard techniques that will be apparent to those skilled in the art (see the Exemplification for exemplary methods). Such methods include yeast and mammalian two-hybrid assays and co-immunoprecipitation techniques.

For example, a compound that modulates DOT1L H3K79 HMTase activity can be verified by: contacting a DOT1L polypeptide with a histone or peptide substrate comprising H3 in the presence of a test compound; detecting the level of H3K79 methylation of the histone or peptide substrate under conditions sufficient to provide H3K79 methylation, wherein an elevation or reduction in H3K79 methylation in the presence of the test compound as compared with the level of histone H3K79 methylation in the absence of the test compound indicates that the test compound modulates DOT1L H3K79 HMTase activity.

The screening methods of the invention can be carried out in a cell-based or cell-free system. As a further alternative, the assay can be performed in a whole animal (including transgenic non-human animals). Further, with respect to cell-based systems, the DOT1L polypeptide (or any other polypeptide used in the assay) can be added directly to the cell or can be produced from a nucleic acid in the cell. The nucleic acid can be endogenous to the cell or can be foreign (e.g., a genetically modified cell).

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

Administering a compound of the present invention, or a pharmaceutically acceptable salt, prodrug, metabolite, polymorph or solvate thereof, to a cell or a subject in need thereof results in modulation (i.e., stimulation or inhibition) of an activity of an intracellular target (e.g., substrate). Several intracellular targets can be modulated with the compounds of the present invention, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy.

Methods of measuring cell death are as shown in Li et al., *Proc Natl Acad Sci USA*. 100(5): 2674-8, 2003. In an aspect, cell death occurs by apoptosis.

Preferably, an effective amount of a compound of the present invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a compound of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, induces cell death selectively in one or more cells affected by a cell proliferative disorder.

The present invention relates to a method of treating or preventing cancer by administering a compound of the present invention, or a pharmaceutically acceptable salt, prodrug, metabolite, polymorph or solvate thereof, to a subject in need thereof, where administration of the compound of the present invention, or a pharmaceutically acceptable salt, prodrug, metabolite, polymorph or solvate thereof, results in one or more of the following: accumulation of cells in Gi and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the invention The compounds of the instant invention can also be utilized to treat or prevent cancer either in monotherapy or combination therapy. Accordingly, in one aspect, the present disclosure also provides a composition comprising a compound described herein, or a pharmaceutically acceptable salt thereof, and one or more therapeutic agents. The present invention provides for the administration of a compound described herein, or a pharmaceutically acceptable salt thereof, and one or more therapeutic agents as a co-formulation or separate formulations, wherein the administration of formulations is simultaneous, sequential, or in alternation. In one embodiment, the one or more therapeutic agents can be an agent that is recognized in the art as being useful to treat the disease or condition being treated by the composition of the present invention. In another embodiment, the one or more therapeutic agents can be an agent that is not recognized in the art as being useful to treat the disease or condition being treated by the composition of the present invention. In one aspect, the other therapeutic agents can be an agent that imparts a beneficial attribute to the composition of the present invention (e.g., an agent that affects the viscosity of the composition). The beneficial attribute to the composition of the present invention includes, but is not limited to, pharmacokinetic or pharmacodynamic co-action resulting from the combination of a compound of Formula (I) or (II) and one or more therapeutic agents. For example, the one or more therapeutic agents can be anticancer agents or chemotherapeutic agents.

For example, the one or more therapeutic agents can be selected from Ara-C, Daunorubicin, Decitabine, Vidaza, Mitoxantrone, JQ1, IBET151, Panobinostat, Vorinostat, Quizartinib, Midostaurin, Tranylcypromine, LSD1 inhibitor II, Navitoclax, or functional analogs, derivatives, prodrugs, and metabolites thereof. Preferably, the therapeutic agent is Ara-C or Daunorubicin or functional analogs, derivatives, prodrugs, and metabolites thereof. For example, a composition of the invention comprises Ara-C and a compound of Formula (I) or (II), or a pharmaceutically acceptable salt thereof. For example, Ara-C and a compound of Formula (I) or (II), or a pharmaceutically acceptable salt thereof are administered together or separately, simultaneously or sequentially, or in alternation.

In some embodiments, the therapeutic agents are topoisomerase inhibitors (e.g., Mitoxantrone), hypomethylating agents (e.g., Decitabine or Vidaza), Bromodomain inhibitors (e.g., IBET-151), HDAC inhibitors (e.g., Panobinostat), Bcl-2 inhibitors (e.g., Navitoclax) or FLT inhibitors (e.g., Quizartinib).

In one embodiment, the other therapeutic agent is an anticancer agent. In one embodiment, the anticancer agent is a compound that affects histone modifications, such as an HDAC inhibitor. In certain embodiments, an anticancer agent is selected from the group consisting of chemotherapeutics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®); biologics (such as Alpha Interferon, *Bacillus* Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™ Thalomid®, Tykerb®, Velcade® and Zevalin™); corticosteroids, (such as dexamethasone sodium phosphate, DeltaSone® and Delta-Cortef®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153).

In another embodiment, the other therapeutic agent is a chemotherapeutic agent (also referred to as an anti-neoplastic agent or anti-proliferative agent), selected from the group including an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodinel 31 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristine, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem;

Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate), or lovastatin.

In another aspect, the other therapeutic agent is a chemotherapeutic agent or a cytokine such as G-CSF (granulocyte colony stimulating factor).

In yet another aspect, the other therapeutic agents can be standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™), CHOP (cyclophosphamide, hydroxydaunorubicin, oncovin, and prednisone or prednisolone), R-CHOP (rituximab, cyclophosphamide, hydroxydaunorubicin, oncovin, prednisone or prednisolone), or CMFP (cyclophosphamide, methotrexate, 5-fluorouracil and prednisone).

In another aspect, the other therapeutic agents can be an inhibitor of an enzyme, such as a receptor or non-receptor kinase. Receptor and non-receptor kinases are, for example, tyrosine kinases or serine/threonine kinases. Kinase inhibitors described herein are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-B, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK). Other examples of the other therapeutic agents and combination therapy can be found in, e.g., co-owned US Provisional Application No. 61/61/785,446 with the title "Combination Therapy For Treating Cancer" filed Mar. 14, 2013, the contents of which are hereby incorporated by reference in its entirety.

As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. Therapeutic agents may also be administered in alternation.

The combination therapies featured in the present invention can result in a synergistic effect in the treatment of a disease or cancer. A "synergistic effect" is defined as where the efficacy of a combination of therapeutic agents is greater than the sum of the effects of any of the agents given alone. A synergistic effect may also be an effect that cannot be achieved by administration of any of the compounds or other therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In another aspect, the compounds described herein, pharmaceutically acceptable salts thereof, and/or the compositions described herein may be administered in combination with radiation therapy. Radiation therapy can also be administered in combination with a composition of the present invention and another chemotherapeutic agent described herein as part of a multiple agent therapy.

The compounds of the instant invention can also be utilized to treat or prevent neurologic diseases or disorders in monotherapy or combination therapy. Neurologic diseases or disorders that may be treated with the compounds of this invention include epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCA7), and Spinocerebellar Ataxia 12 (SCA12).

Any other disease in which epigenetic methylation, which is mediated by DOT1, plays a role may be treatable or preventable using compounds and methods described herein.

In one aspect, the compound suitable for the method of the invention, e.g., a DOT1L inhibitor, is a compound of Formula (I) or (II) described herein, or a pharmaceutically acceptable salt or ester thereof:

The invention also relates to a pharmaceutical composition of a therapeutically effective amount of a compound of any of the Formulae disclosed herein and a pharmaceutically acceptable carrier.

The invention also relates to a pharmaceutical composition of a therapeutically effective amount of a salt of a compound of any of the Formulae disclosed herein and a pharmaceutically acceptable carrier.

The invention also relates to a pharmaceutical composition of a therapeutically effective amount of a hydrate of a compound of any of the Formulae disclosed herein and a pharmaceutically acceptable carrier.

The invention also relates to a pharmaceutical composition of a therapeutically effective amount of a compound selected from compounds 1-89, 101-104, and 107-114 and pharmaceutically acceptable salts thereof and a pharmaceutically acceptable carrier. The invention also relates to a pharmaceutical composition of a therapeutically effective amount of a salt of a compound selected from compounds 1-89, 101-104, and 107-114 and pharmaceutically acceptable salts thereof and a pharmaceutically acceptable carrier. The invention also relates to a pharmaceutical composition of a therapeutically effective amount of a hydrate of a compound selected from compounds 1-89, 101-104, and 107-114 and pharmaceutically acceptable salts thereof and a pharmaceutically acceptable carrier.

The present invention provides methods of treating or preventing cancer. The present invention provides methods of treating cancer. The present invention also provides methods of preventing cancer. The method includes administering to a subject in need thereof a therapeutically effective amount of the compound of any of the Formulae disclosed herein. The cancer can be a hematological cancer. Preferably, the cancer is leukemia. More preferably, the cancer is acute myeloid leukemia, acute lymphocytic leukemia or mixed lineage leukemia.

The present invention provides methods of treating or preventing a disease or disorder mediated by translocation of a gene on chromosome 11 q23. The present invention provides methods of treating a disease or disorder mediated by translocation of a gene on chromosome 11q23. The present invention also provides methods of preventing a disease or disorder mediated by translocation of a gene on chromosome 11 q23. The method includes administering to a subject in need thereof a therapeutically effective amount of the compound of any of the Formulae disclosed herein.

The present invention provides methods of treating or preventing a disease or disorder in which DOT1L-mediated protein methylation plays a part or a disease or disorder mediated by DOT1L-mediated protein methylation. The present invention provides methods of treating a disease or disorder in which DOT1L-mediated protein methylation plays a part or a disease or disorder mediated by DOT1L-mediated protein methylation. The present invention also provides methods of preventing a disease or disorder in which DOT1L-mediated protein methylation plays a part or a disease or disorder mediated by DOT1L-mediated protein methylation. The method includes administering to a subject in need thereof a therapeutically effective amount of the compound of any of the Formulae disclosed herein.

The present invention provides methods of inhibiting DOT1L activity in a cell. The method includes contacting the cell with an effective amount of one or more of the compound of any of the Formulae disclosed herein.

Still another aspect of the invention relates to a method of reducing the level of Histone H3 Lysine residue 79 (H3-K79) methylation in a cell. The method includes contacting a cell with a compound of the present invention. Such method can be used to ameliorate any condition which is caused by or potentiated by the activity of DOT1L through H3-K79 methylation.

The present invention relates to use of the compounds disclosed herein in preparation of a medicament for treating or preventing cancer. The use includes a compound of any of the Formulae disclosed herein for administration to a subject in need thereof in a therapeutically effective amount. The cancer can be a hematological cancer. Preferably, the cancer is leukemia. More preferably, the cancer is acute myeloid leukemia, acute lymphocytic leukemia or mixed lineage leukemia.

The present invention provides use of the compounds disclosed herein in preparation of a medicament for treating or preventing a disease or disorder mediated by translocation of a gene on chromosome 11q23. The use includes a compound of any of the Formulae disclosed herein for administration to a subject in need thereof in a therapeutically effective amount.

The present invention provides use of the compounds disclosed herein in preparation of a medicament for treating or preventing a disease or disorder in which DOT1L-mediated protein methylation plays a part or a disease or disorder mediated by DOT1L-mediated protein methylation. The use includes a compound of any of the Formulae disclosed herein for administration to a subject in need thereof in a therapeutically effective amount.

The present invention provides use of the compounds disclosed herein for inhibiting DOT1L activity in a cell. The use includes contacting the cell with an effective amount of one or more of the compound of any of the Formulae disclosed herein.

Still another aspect of the invention relates to a use of the compounds disclosed herein for reducing the level of Histone H3 Lysine residue 79 (H3-K79) methylation in a cell. The use includes contacting a cell with a compound of the present invention. Such use can ameliorate any condition which is caused by or potentiated by the activity of DOT1L through H3-K79 methylation.

In the formulae presented herein, the variables can be selected from the respective groups of chemical moieties later defined in the detailed description.

In addition, the invention provides methods of synthesizing the foregoing compounds. Following synthesis, a therapeutically effective amount of one or more of the compounds can be formulated with a pharmaceutically acceptable carrier for administration to a mammal, particularly humans, for use in modulating an epigenetic enzyme. In certain embodiments, the compounds of the present invention are useful for treating, preventing, or reducing the risk of cancer or for the manufacture of a medicament for treating, preventing, or reducing the risk of cancer. Accordingly, the compounds or the formulations can be administered, for example, via oral, parenteral, otic, ophthalmic, nasal, or topical routes, to provide an effective amount of the compound to the mammal.

Representative compounds of the present invention include compounds listed in Tables 1 and 2.

TABLE 1

| Compound no. | Structure |
|---|---|
| 1 | 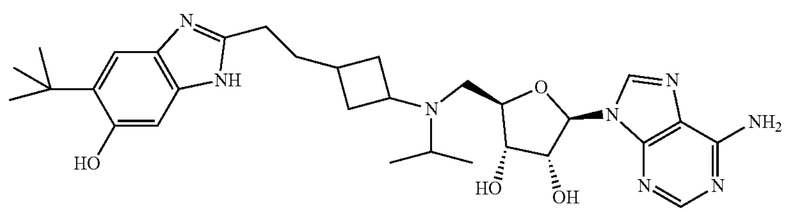 [SMILES: CC(C)N(C[C@H]1O[C@@H](n2cnc3c(N)ncnc32)[C@H](O)[C@@H]1O)C1CC(CCc2nc3cc(C(C)(C)C)c(O)cc3[nH]2)C1] |
| 2 | 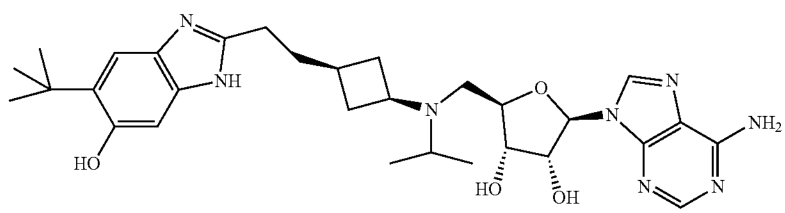 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)c(O)cc3[nH]2)C1] |
| 3 | 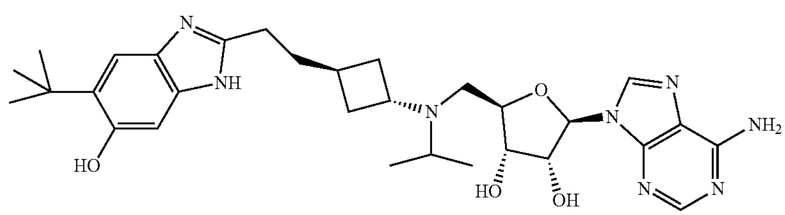 [SMILES: CC(C)N(C[C@H]1O[C@@H](n2cnc3c(N)ncnc32)[C@H](O)[C@@H]1O)[C@H]1C[C@H](CCc2nc3cc(C(C)(C)C)c(O)cc3[nH]2)C1] |
| 4 | 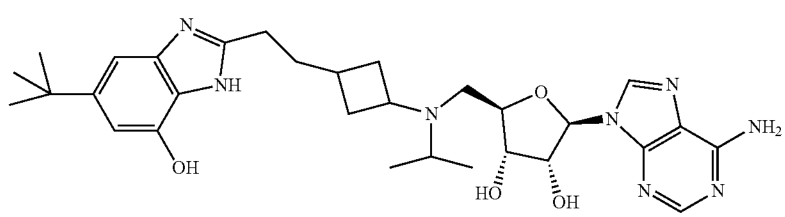 [SMILES: CC(C)N(C[C@H]1O[C@@H](n2cnc3c(N)ncnc32)[C@H](O)[C@@H]1O)C1CC(CCc2nc3cc(C(C)(C)C)cc(O)c3[nH]2)C1] |

US 10,400,005 B2
TABLE 1-continued
| Compound no. | Structure |
|---|---|
| 5 | 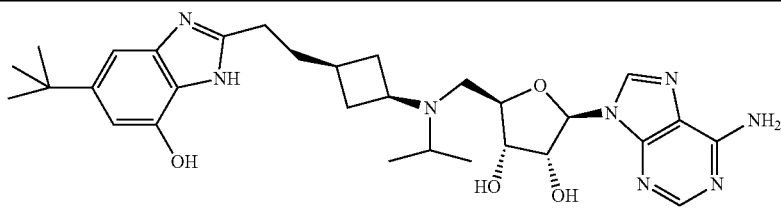 |
| 6 | 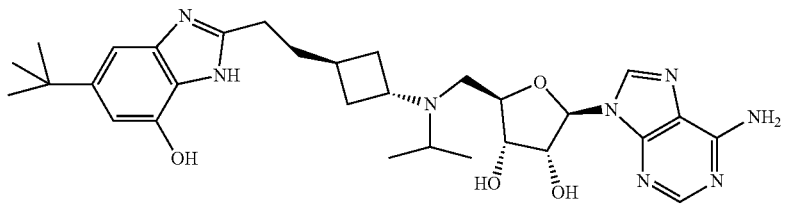 [SMILES: CC(C)N(C[C@H]1O[C@@H](n2cnc3c(N)ncnc32)[C@H](O)[C@@H]1O)[C@H]1C[C@H](CCc2nc3cc(C(C)(C)C)cc(O)c3[nH]2)C1] |
| 7 | 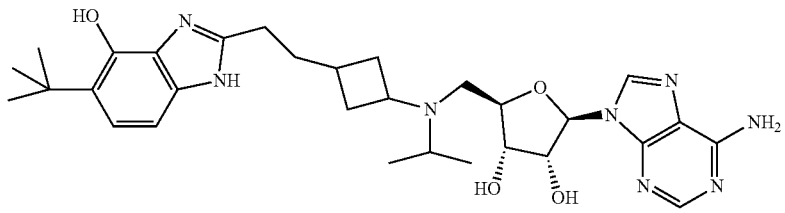 [SMILES: CC(C)N(C[C@H]1O[C@@H](n2cnc3c(N)ncnc32)[C@H](O)[C@@H]1O)C1CC(CCc2nc3c(O)c(C(C)(C)C)ccc3[nH]2)C1] |
| 8 | 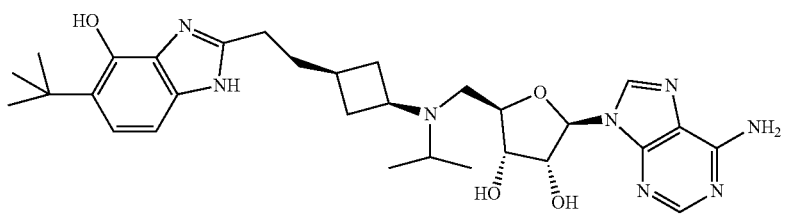 [SMILES: CC(C)N(C[C@H]1O[C@@H](n2cnc3c(N)ncnc32)[C@H](O)[C@@H]1O)[C@H]1C[C@@H](CCc2nc3c(O)c(C(C)(C)C)ccc3[nH]2)C1] |
| 9 | 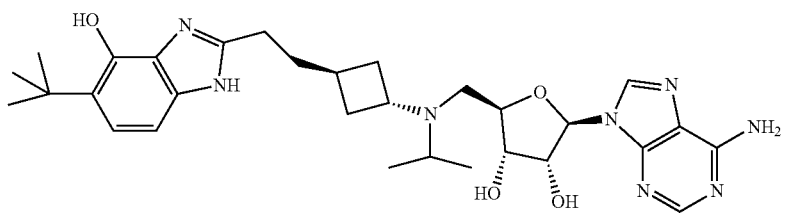 [SMILES: CC(C)N(C[C@H]1O[C@@H](n2cnc3c(N)ncnc32)[C@H](O)[C@@H]1O)[C@H]1C[C@H](CCc2nc3c(O)c(C(C)(C)C)ccc3[nH]2)C1] |
| 10 | 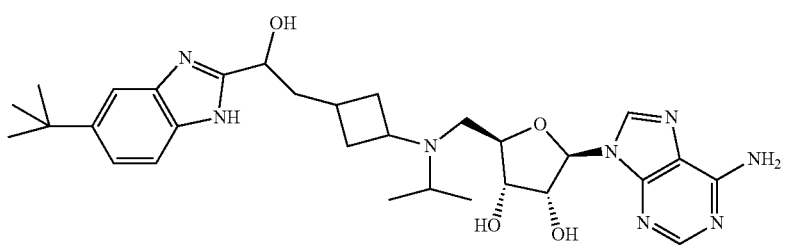 [SMILES: CC(C)N(C[C@H]1O[C@@H](n2cnc3c(N)ncnc32)[C@H](O)[C@@H]1O)C1CC(CC(O)c2nc3cc(C(C)(C)C)ccc3[nH]2)C1] |
| 11 | 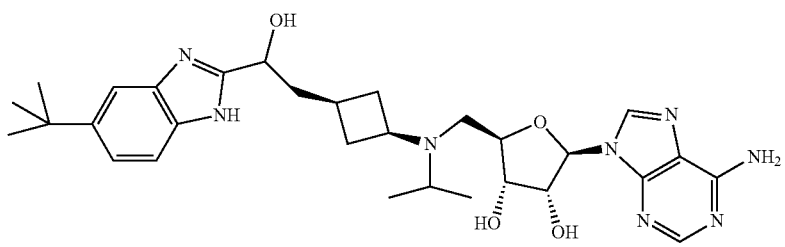 [SMILES: CC(C)N(C[C@H]1O[C@@H](n2cnc3c(N)ncnc32)[C@H](O)[C@@H]1O)[C@H]1C[C@@H](CC(O)c2nc3cc(C(C)(C)C)ccc3[nH]2)C1] |

TABLE 1-continued
| Compound no. | Structure |
|---|---|
| 12 | 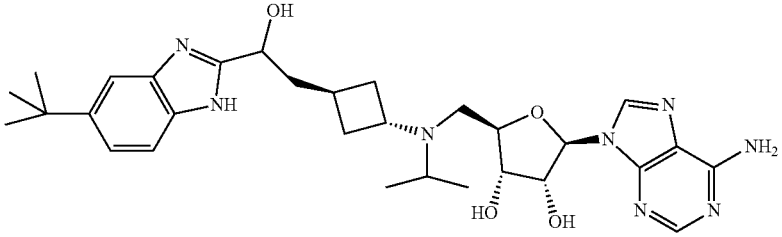 [SMILES: CC(C)N(C[C@H]1O[C@@H](n2cnc3c(N)ncnc32)[C@H](O)[C@@H]1O)[C@H]1C[C@H](CC(O)c2nc3cc(C(C)(C)C)ccc3[nH]2)C1] |
| 13 | 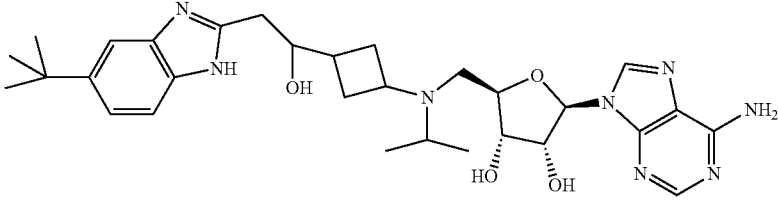 [SMILES: CC(C)N(C[C@H]1O[C@@H](n2cnc3c(N)ncnc32)[C@H](O)[C@@H]1O)C1CC(C(O)Cc2nc3cc(C(C)(C)C)ccc3[nH]2)C1] |
| 14 | 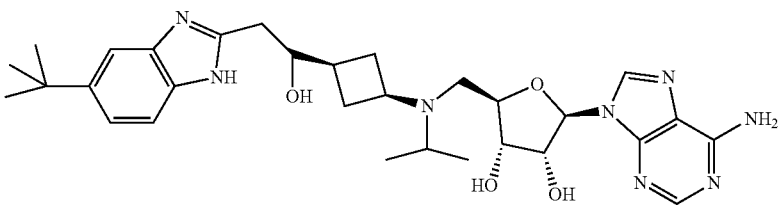 [SMILES: CC(C)N(C[C@H]1O[C@@H](n2cnc3c(N)ncnc32)[C@H](O)[C@@H]1O)[C@H]1C[C@@H](C(O)Cc2nc3cc(C(C)(C)C)ccc3[nH]2)C1] |
| 15 | 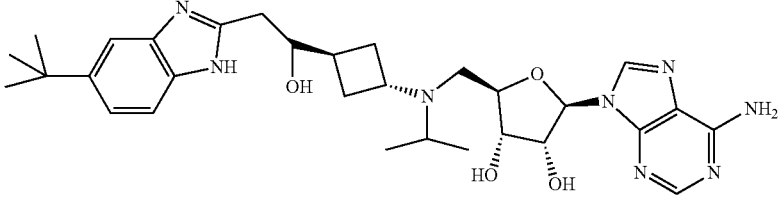 [SMILES: CC(C)N(C[C@H]1O[C@@H](n2cnc3c(N)ncnc32)[C@H](O)[C@@H]1O)[C@H]1C[C@H](C(O)Cc2nc3cc(C(C)(C)C)ccc3[nH]2)C1] |
| 16 | 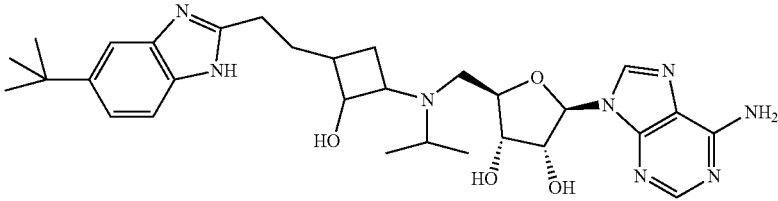 [SMILES: CC(C)N(C[C@H]1O[C@@H](n2cnc3c(N)ncnc32)[C@H](O)[C@@H]1O)C1CC(CCc2nc3cc(C(C)(C)C)ccc3[nH]2)C1O] |
| 17 | 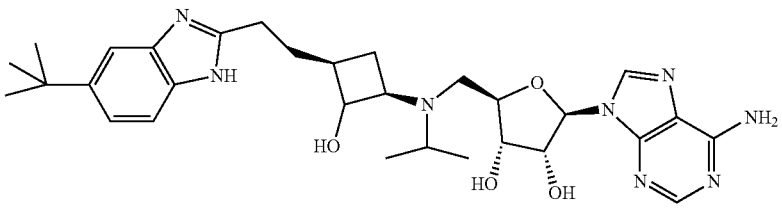 [SMILES: CC(C)N(C[C@H]1O[C@@H](n2cnc3c(N)ncnc32)[C@H](O)[C@@H]1O)[C@@H]1C[C@H](CCc2nc3cc(C(C)(C)C)ccc3[nH]2)C1O] |
| 18 | 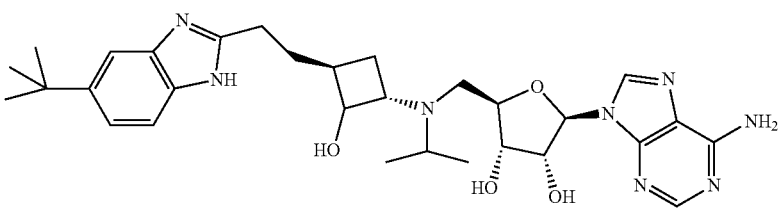 [SMILES: CC(C)N(C[C@H]1O[C@@H](n2cnc3c(N)ncnc32)[C@H](O)[C@@H]1O)[C@H]1C[C@H](CCc2nc3cc(C(C)(C)C)ccc3[nH]2)C1O] |

TABLE 1-continued

| Compound no. | Structure |
|---|---|
| 19 | 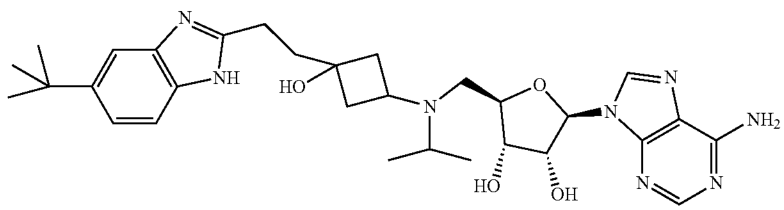 [SMILES: CC(C)N(C[C@H]1O[C@@H](n2cnc3c(N)ncnc32)[C@H](O)[C@@H]1O)C1CC(O)(CCc2nc3cc(C(C)(C)C)ccc3[nH]2)C1] |
| 20 | 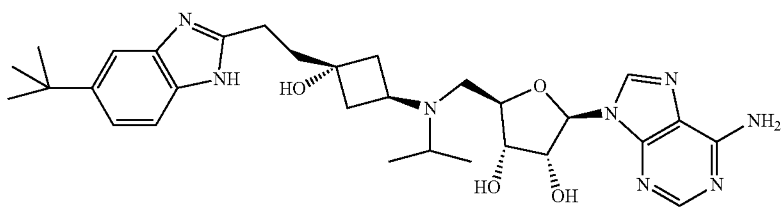 [SMILES: CC(C)N(C[C@H]1O[C@@H](n2cnc3c(N)ncnc32)[C@H](O)[C@@H]1O)[C@H]1C[C@@](O)(CCc2nc3cc(C(C)(C)C)ccc3[nH]2)C1] |
| 21 | 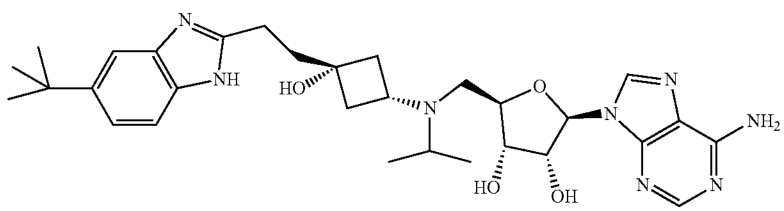 [SMILES: CC(C)N(C[C@H]1O[C@@H](n2cnc3c(N)ncnc32)[C@H](O)[C@@H]1O)[C@H]1C[C@](O)(CCc2nc3cc(C(C)(C)C)ccc3[nH]2)C1] |
| 22 | 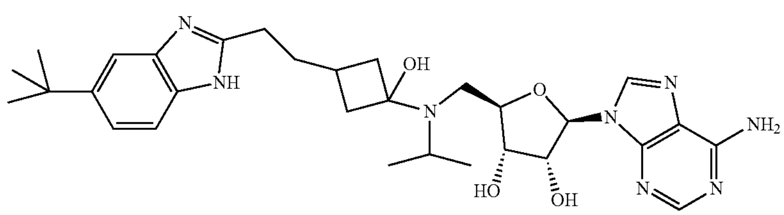 [SMILES: CC(C)N(C[C@H]1O[C@@H](n2cnc3c(N)ncnc32)[C@H](O)[C@@H]1O)C1(O)CC(CCc2nc3cc(C(C)(C)C)ccc3[nH]2)C1] |
| 23 | 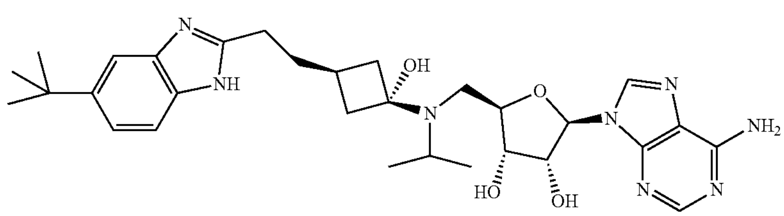 [SMILES: CC(C)N(C[C@H]1O[C@@H](n2cnc3c(N)ncnc32)[C@H](O)[C@@H]1O)[C@]1(O)C[C@H](CCc2nc3cc(C(C)(C)C)ccc3[nH]2)C1] |
| 24 | 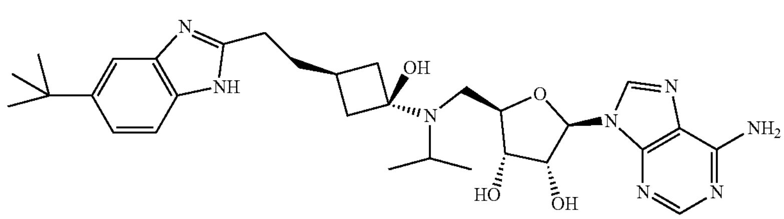 [SMILES: CC(C)N(C[C@H]1O[C@@H](n2cnc3c(N)ncnc32)[C@H](O)[C@@H]1O)[C@]1(O)C[C@@H](CCc2nc3cc(C(C)(C)C)ccc3[nH]2)C1] |
| 25 | 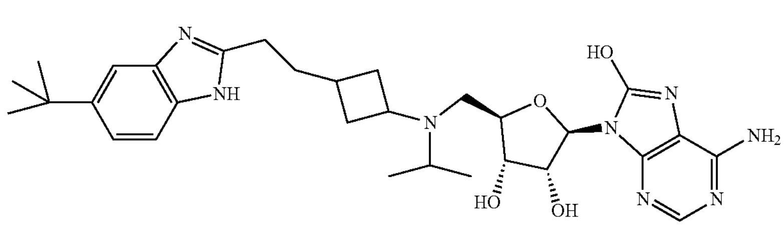 [SMILES: CC(C)N(C[C@H]1O[C@@H](n2c(O)nc3c(N)ncnc32)[C@H](O)[C@@H]1O)C1CC(CCc2nc3cc(C(C)(C)C)ccc3[nH]2)C1] |

TABLE 1-continued

| Compound no. | Structure |
|---|---|
| 26 | 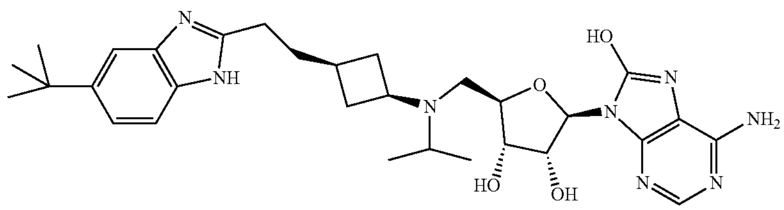 [SMILES: CC(C)N(C[C@H]1O[C@@H](n2c(O)nc3c(N)ncnc32)[C@H](O)[C@@H]1O)[C@H]1C[C@@H](CCc2nc3cc(C(C)(C)C)ccc3[nH]2)C1] |
| 27 | 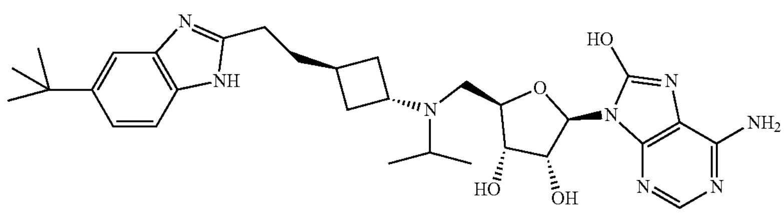 [SMILES: CC(C)N(C[C@H]1O[C@@H](n2c(O)nc3c(N)ncnc32)[C@H](O)[C@@H]1O)[C@H]1C[C@H](CCc2nc3cc(C(C)(C)C)ccc3[nH]2)C1] |
| 28 | 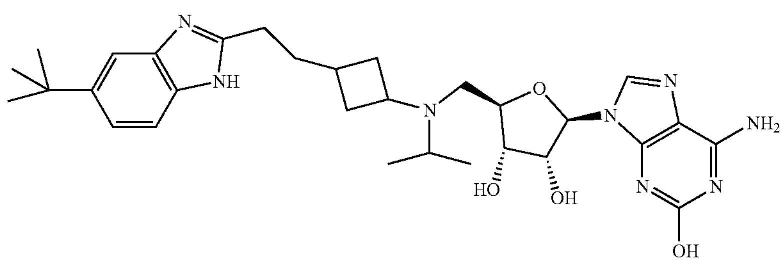 [SMILES: CC(C)N(C[C@H]1O[C@@H](n2cnc3c(N)nc(O)nc32)[C@H](O)[C@@H]1O)C1CC(CCc2nc3cc(C(C)(C)C)ccc3[nH]2)C1] |
| 29 | 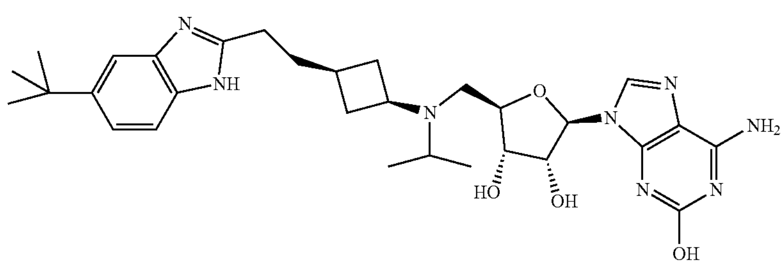 [SMILES: CC(C)N(C[C@H]1O[C@@H](n2cnc3c(N)nc(O)nc32)[C@H](O)[C@@H]1O)[C@H]1C[C@@H](CCc2nc3cc(C(C)(C)C)ccc3[nH]2)C1] |
| 30 | 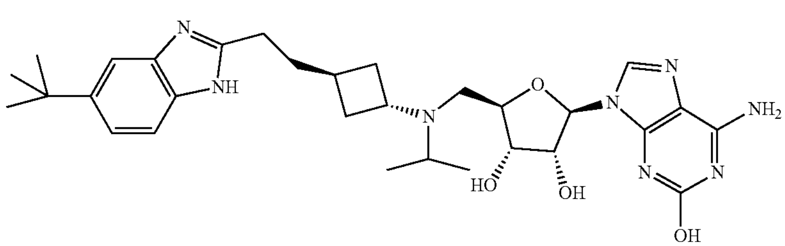 [SMILES: CC(C)N(C[C@H]1O[C@@H](n2cnc3c(N)nc(O)nc32)[C@H](O)[C@@H]1O)[C@H]1C[C@H](CCc2nc3cc(C(C)(C)C)ccc3[nH]2)C1] |
| 31 | 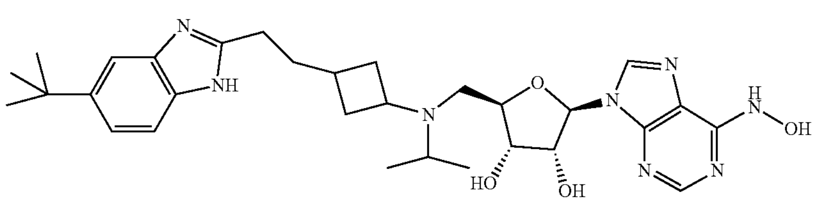 [SMILES: CC(C)N(C[C@H]1O[C@@H](n2cnc3c(NO)ncnc32)[C@H](O)[C@@H]1O)C1CC(CCc2nc3cc(C(C)(C)C)ccc3[nH]2)C1] |

TABLE 1-continued

| Compound no. | Structure |
|---|---|
| 32 | 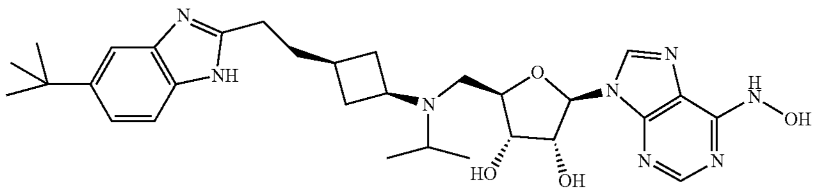 [SMILES: CC(C)N(C[C@H]1O[C@@H](n2cnc3c(NO)ncnc32)[C@H](O)[C@@H]1O)[C@H]1C[C@@H](CCc2nc3cc(C(C)(C)C)ccc3[nH]2)C1] |
| 33 | 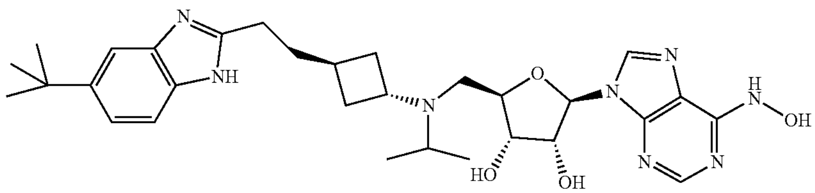 [SMILES: CC(C)N(C[C@H]1O[C@@H](n2cnc3c(NO)ncnc32)[C@H](O)[C@@H]1O)[C@H]1C[C@H](CCc2nc3cc(C(C)(C)C)ccc3[nH]2)C1] |
| 34 | 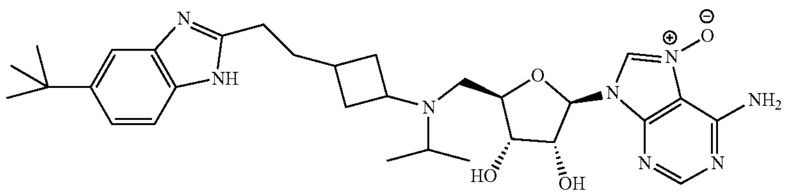 [SMILES: CC(C)N(C[C@H]1O[C@@H](n2c[n+]([O-])c3c(N)ncnc32)[C@H](O)[C@@H]1O)C1CC(CCc2nc3cc(C(C)(C)C)ccc3[nH]2)C1] |
| 35 | 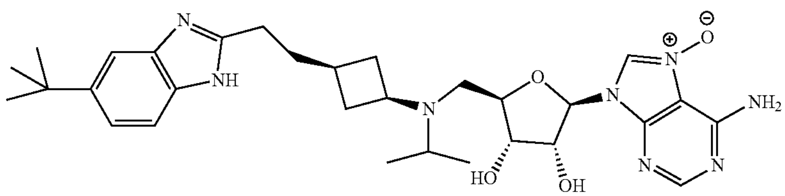 [SMILES: CC(C)N(C[C@H]1O[C@@H](n2c[n+]([O-])c3c(N)ncnc32)[C@H](O)[C@@H]1O)[C@H]1C[C@@H](CCc2nc3cc(C(C)(C)C)ccc3[nH]2)C1] |
| 36 | 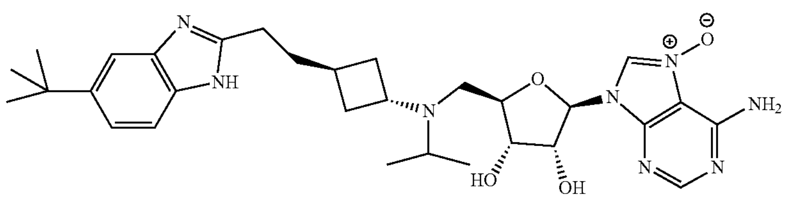 [SMILES: CC(C)N(C[C@H]1O[C@@H](n2c[n+]([O-])c3c(N)ncnc32)[C@H](O)[C@@H]1O)[C@H]1C[C@H](CCc2nc3cc(C(C)(C)C)ccc3[nH]2)C1] |
| 37 | 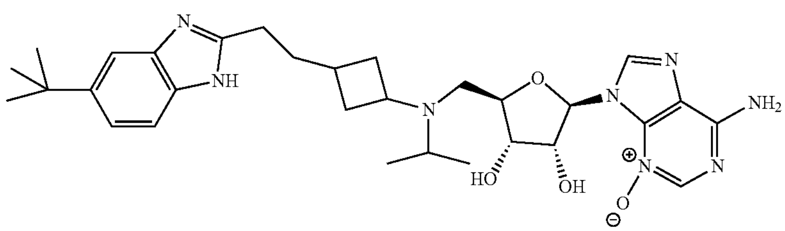 [SMILES: CC(C)N(C[C@H]1O[C@@H](n2cnc3c(N)nc[n+]([O-])c32)[C@H](O)[C@@H]1O)C1CC(CCc2nc3cc(C(C)(C)C)ccc3[nH]2)C1] |
| 38 | 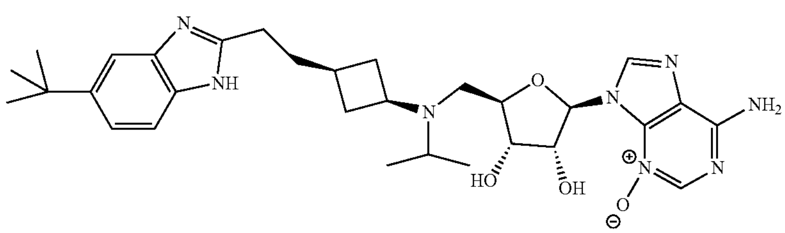 [SMILES: CC(C)N(C[C@H]1O[C@@H](n2cnc3c(N)nc[n+]([O-])c32)[C@H](O)[C@@H]1O)[C@H]1C[C@@H](CCc2nc3cc(C(C)(C)C)ccc3[nH]2)C1] |

TABLE 1-continued
| Compound no. | Structure |
|---|---|
| 39 | 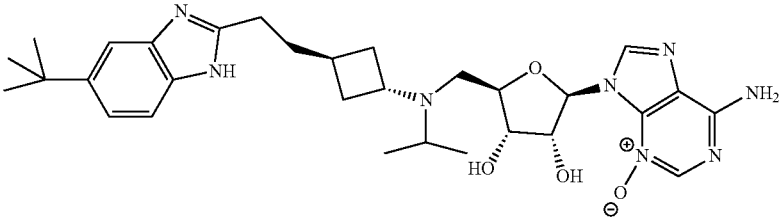 [SMILES: CC(C)N(C[C@H]1O[C@@H](n2cnc3c(N)nc[n+]([O-])c32)[C@H](O)[C@@H]1O)[C@H]1C[C@H](CCc2nc3cc(C(C)(C)C)ccc3[nH]2)C1] |
| 40 | 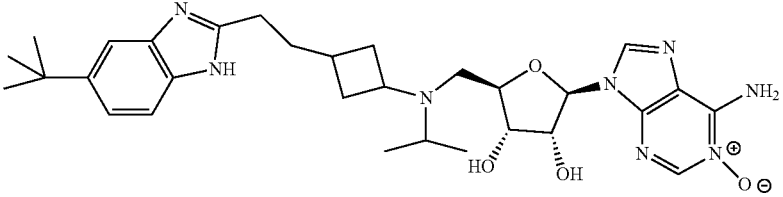 [SMILES: CC(C)N(C[C@H]1O[C@@H](n2cnc3c(N)[n+]([O-])cnc32)[C@H](O)[C@@H]1O)C1CC(CCc2nc3cc(C(C)(C)C)ccc3[nH]2)C1] |
| 41 | 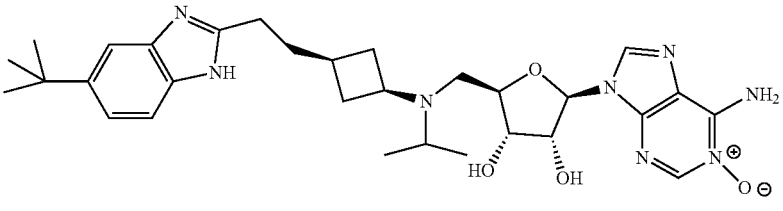 [SMILES: CC(C)N(C[C@H]1O[C@@H](n2cnc3c(N)[n+]([O-])cnc32)[C@H](O)[C@@H]1O)[C@H]1C[C@@H](CCc2nc3cc(C(C)(C)C)ccc3[nH]2)C1] |
| 42 | 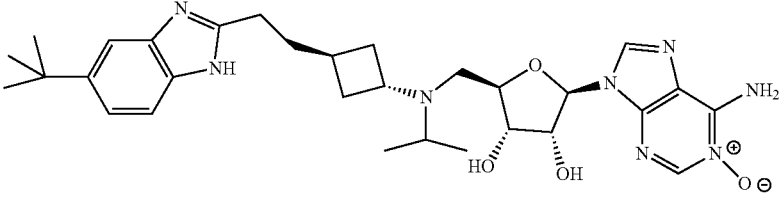 [SMILES: CC(C)N(C[C@H]1O[C@@H](n2cnc3c(N)[n+]([O-])cnc32)[C@H](O)[C@@H]1O)[C@H]1C[C@H](CCc2nc3cc(C(C)(C)C)ccc3[nH]2)C1] |
| 43 | 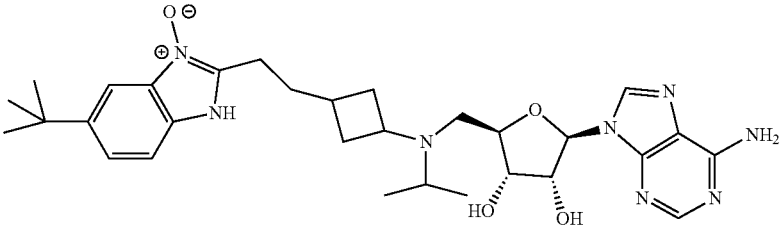 [SMILES: CC(C)N(C[C@H]1O[C@@H](n2cnc3c(N)ncnc32)[C@H](O)[C@@H]1O)C1CC(CCc2[nH]c3ccc(C(C)(C)C)cc3[n+]2[O-])C1] |
| 44 | 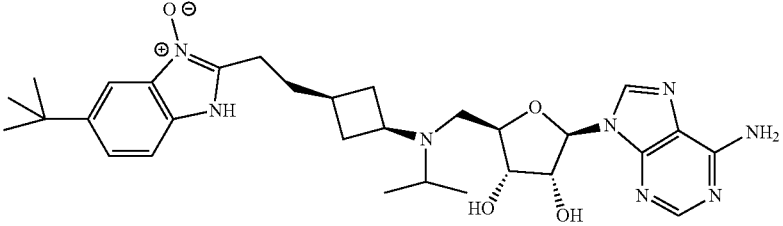 [SMILES: CC(C)N(C[C@H]1O[C@@H](n2cnc3c(N)ncnc32)[C@H](O)[C@@H]1O)[C@H]1C[C@@H](CCc2[nH]c3ccc(C(C)(C)C)cc3[n+]2[O-])C1] |

TABLE 1-continued

| Compound no. | Structure |
|---|---|
| 45 | 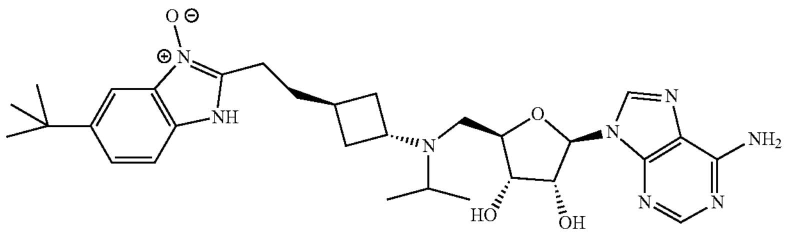 [SMILES: CC(C)N(C[C@H]1O[C@@H](n2cnc3c(N)ncnc32)[C@H](O)[C@@H]1O)[C@H]1C[C@H](CCc2[nH]c3ccc(C(C)(C)C)cc3[n+]2[O-])C1] |
| 46 | 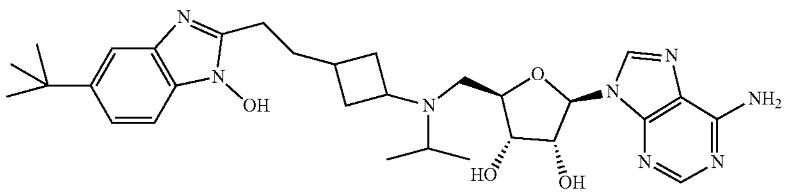 [SMILES: CC(C)N(C[C@H]1O[C@@H](n2cnc3c(N)ncnc32)[C@H](O)[C@@H]1O)C1CC(CCc2nc3cc(C(C)(C)C)ccc3n2O)C1] |
| 47 | 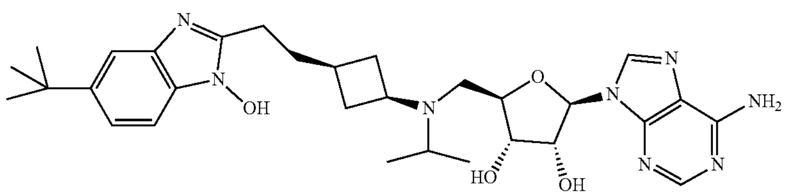 [SMILES: CC(C)N(C[C@H]1O[C@@H](n2cnc3c(N)ncnc32)[C@H](O)[C@@H]1O)[C@H]1C[C@@H](CCc2nc3cc(C(C)(C)C)ccc3n2O)C1] |
| 48 | 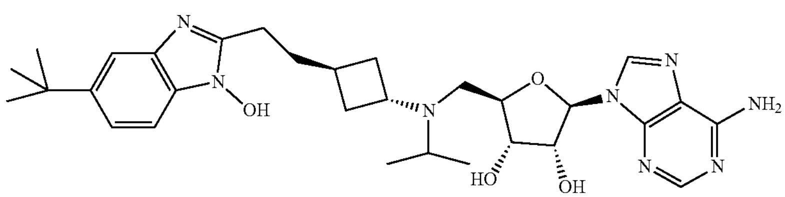 [SMILES: CC(C)N(C[C@H]1O[C@@H](n2cnc3c(N)ncnc32)[C@H](O)[C@@H]1O)[C@H]1C[C@H](CCc2nc3cc(C(C)(C)C)ccc3n2O)C1] |
| 49 | 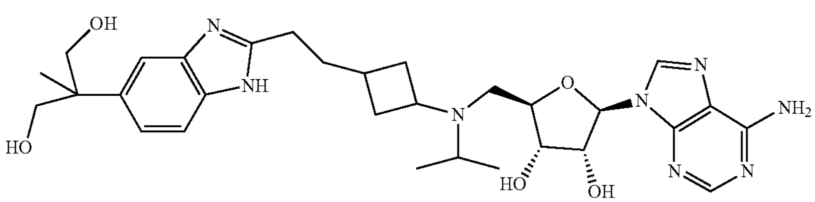 [SMILES: CC(C)N(C[C@H]1O[C@@H](n2cnc3c(N)ncnc32)[C@H](O)[C@@H]1O)C1CC(CCc2nc3cc(C(C)(CO)CO)ccc3[nH]2)C1] |
| 50 | 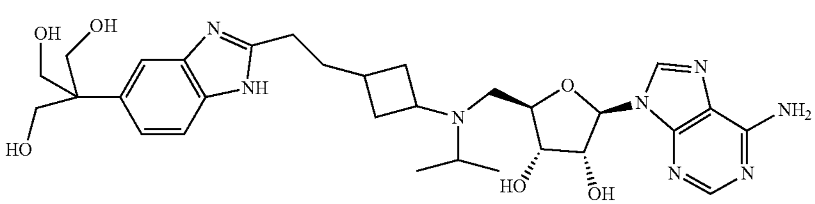 [SMILES: CC(C)N(C[C@H]1O[C@@H](n2cnc3c(N)ncnc32)[C@H](O)[C@@H]1O)C1CC(CCc2nc3cc(C(CO)(CO)CO)ccc3[nH]2)C1] |
| 51 | 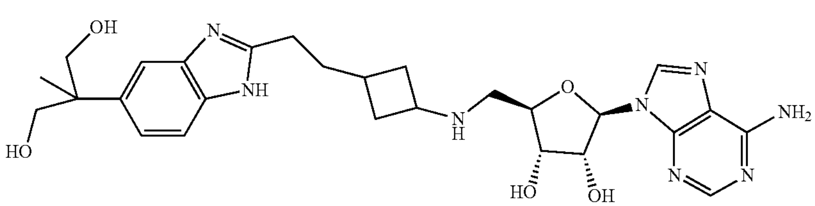 [SMILES: CC(CO)(CO)c1ccc2[nH]c(CCC3CC(NC[C@H]4O[C@@H](n5cnc6c(N)ncnc65)[C@H](O)[C@@H]4O)C3)nc2c1] |

TABLE 1-continued

| Compound no. | Structure |
|---|---|
| 52 | (structure image) |
| 53 | (structure image) |
| 54 | (structure image) |
| 55 | (structure image) |
| 56 | (structure image) |
| 57 | (structure image) |
| 58 | (structure image) |

TABLE 1-continued

| Compound no. | Structure |
|---|---|
| 59 | 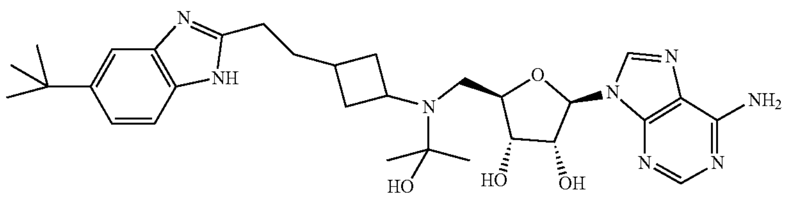 [SMILES: CC(C)(C)c1ccc2[nH]c(CCC3CC(N(C[C@H]4O[C@@H](n5cnc6c(N)ncnc65)[C@H](O)[C@@H]4O)C(C)(C)O)C3)nc2c1] |
| 60 | 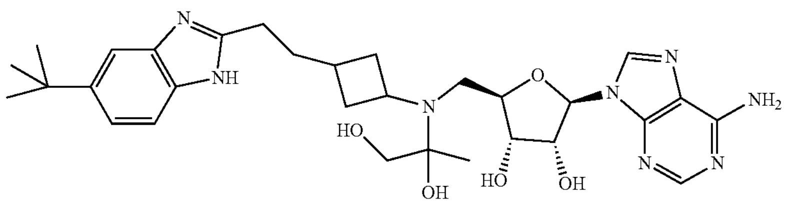 [SMILES: CC(C)(C)c1ccc2[nH]c(CCC3CC(N(C[C@H]4O[C@@H](n5cnc6c(N)ncnc65)[C@H](O)[C@@H]4O)C(C)(O)CO)C3)nc2c1] |
| 61 | 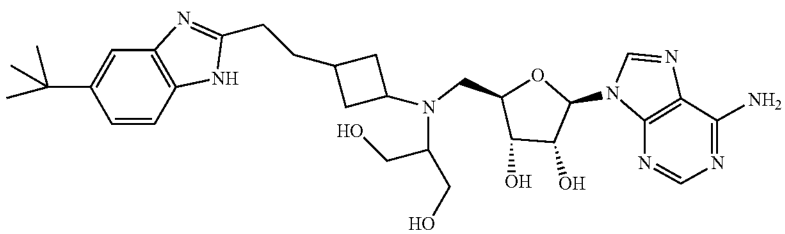 [SMILES: CC(C)(C)c1ccc2[nH]c(CCC3CC(N(C[C@H]4O[C@@H](n5cnc6c(N)ncnc65)[C@H](O)[C@@H]4O)C(CO)CO)C3)nc2c1] |
| 62 | 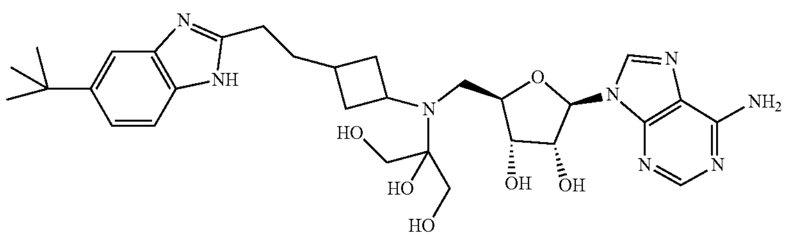 [SMILES: CC(C)(C)c1ccc2[nH]c(CCC3CC(N(C[C@H]4O[C@@H](n5cnc6c(N)ncnc65)[C@H](O)[C@@H]4O)C(O)(CO)CO)C3)nc2c1] |
| 63 | 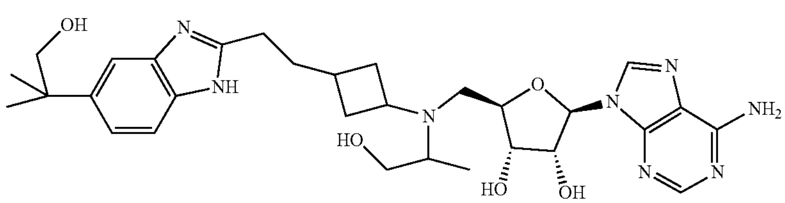 [SMILES: CC(CO)N(C[C@H]1O[C@@H](n2cnc3c(N)ncnc32)[C@H](O)[C@@H]1O)C1CC(CCc2nc3cc(C(C)(C)CO)ccc3[nH]2)C1] |
| 64 | 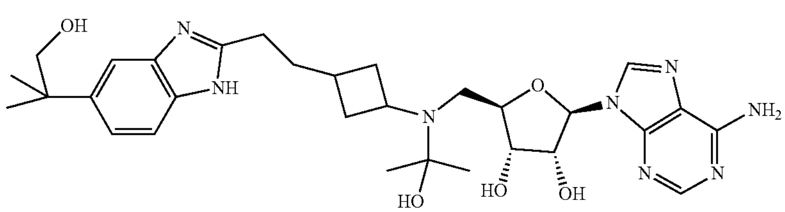 [SMILES: CC(C)(CO)c1ccc2[nH]c(CCC3CC(N(C[C@H]4O[C@@H](n5cnc6c(N)ncnc65)[C@H](O)[C@@H]4O)C(C)(C)O)C3)nc2c1] |
| 65 | 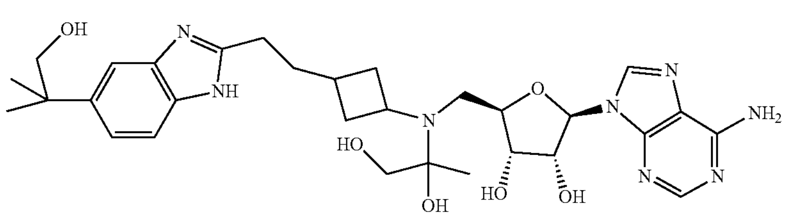 [SMILES: CC(C)(CO)c1ccc2[nH]c(CCC3CC(N(C[C@H]4O[C@@H](n5cnc6c(N)ncnc65)[C@H](O)[C@@H]4O)C(C)(O)CO)C3)nc2c1] |

TABLE 1-continued

| Compound no. | Structure |
|---|---|
| 66 | 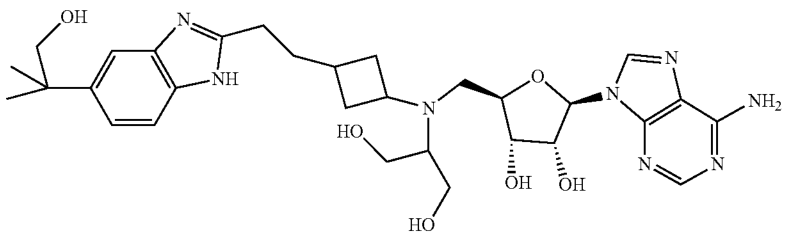 [SMILES: CC(C)(CO)c1ccc2[nH]c(CCC3CC(N(C[C@H]4O[C@@H](n5cnc6c(N)ncnc65)[C@H](O)[C@@H]4O)C(CO)CO)C3)nc2c1] |
| 67 | 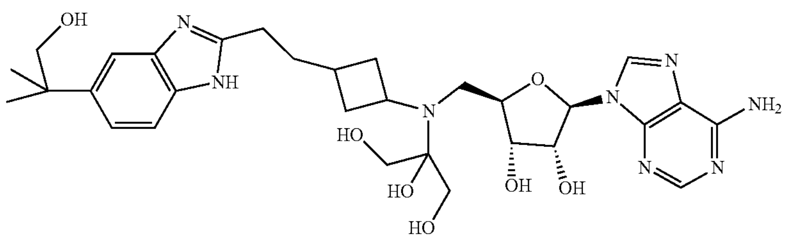 [SMILES: CC(C)(CO)c1ccc2[nH]c(CCC3CC(N(C[C@H]4O[C@@H](n5cnc6c(N)ncnc65)[C@H](O)[C@@H]4O)C(O)(CO)CO)C3)nc2c1] |
| 68 | 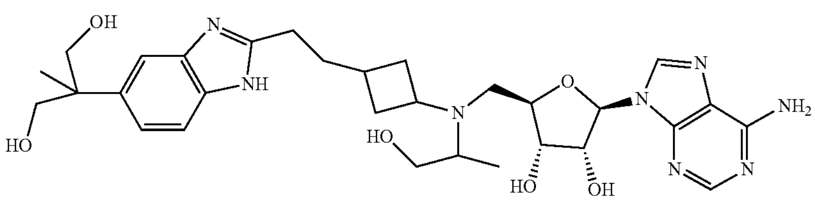 [SMILES: CC(CO)N(C[C@H]1O[C@@H](n2cnc3c(N)ncnc32)[C@H](O)[C@@H]1O)C1CC(CCc2nc3cc(C(C)(CO)CO)ccc3[nH]2)C1] |
| 69 | 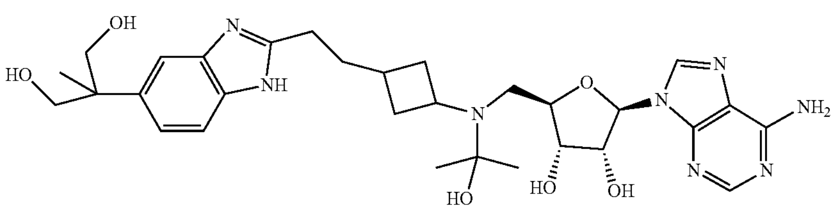 [SMILES: CC(CO)(CO)c1ccc2[nH]c(CCC3CC(N(C[C@H]4O[C@@H](n5cnc6c(N)ncnc65)[C@H](O)[C@@H]4O)C(C)(C)O)C3)nc2c1] |
| 70 | 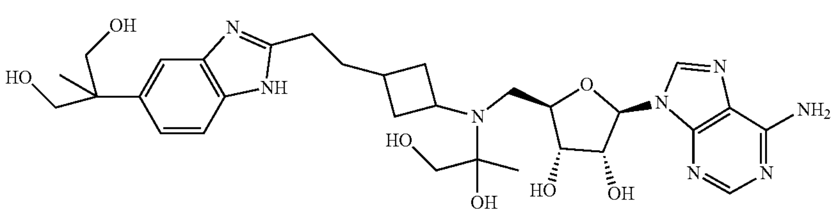 [SMILES: CC(CO)(CO)c1ccc2[nH]c(CCC3CC(N(C[C@H]4O[C@@H](n5cnc6c(N)ncnc65)[C@H](O)[C@@H]4O)C(C)(O)CO)C3)nc2c1] |
| 71 | 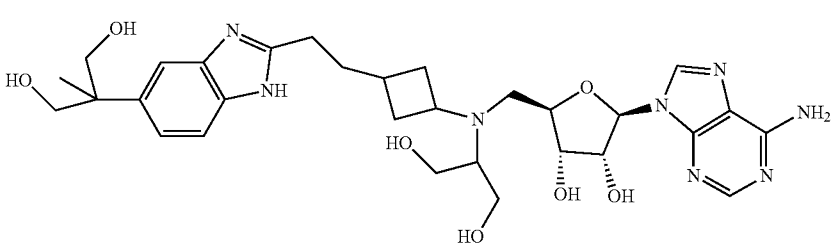 [SMILES: CC(CO)(CO)c1ccc2[nH]c(CCC3CC(N(C[C@H]4O[C@@H](n5cnc6c(N)ncnc65)[C@H](O)[C@@H]4O)C(CO)CO)C3)nc2c1] |

TABLE 1-continued

| Compound no. | Structure |
|---|---|
| 72 | 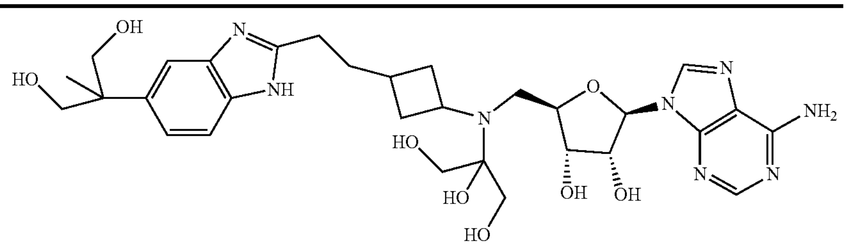 |
| 73 | 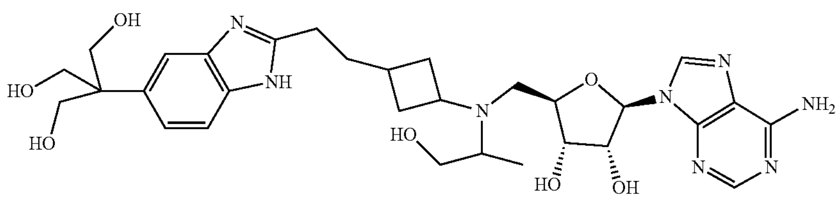 [SMILES: CC(CO)N(C[C@H]1O[C@@H](n2cnc3c(N)ncnc32)[C@H](O)[C@@H]1O)C1CC(CCc2nc3cc(C(CO)(CO)CO)ccc3[nH]2)C1] |
| 74 | 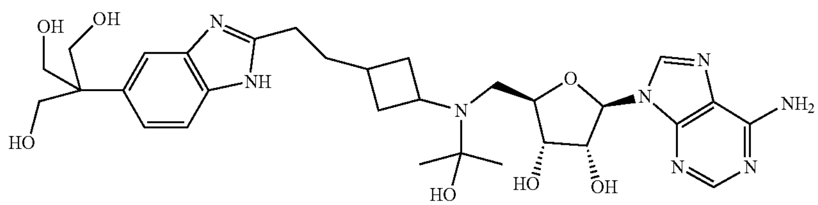 [SMILES: CC(C)(O)N(C[C@H]1O[C@@H](n2cnc3c(N)ncnc32)[C@H](O)[C@@H]1O)C1CC(CCc2nc3cc(C(CO)(CO)CO)ccc3[nH]2)C1] |
| 75 | 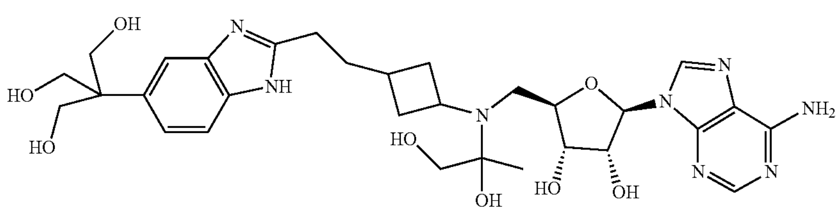 [SMILES: CC(O)(CO)N(C[C@H]1O[C@@H](n2cnc3c(N)ncnc32)[C@H](O)[C@@H]1O)C1CC(CCc2nc3cc(C(CO)(CO)CO)ccc3[nH]2)C1] |
| 76 | 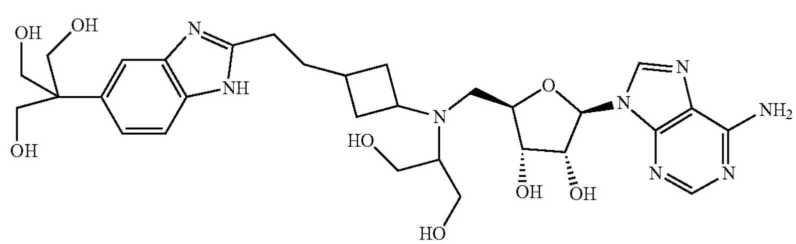 [SMILES: Nc1ncnc2c1ncn2[C@@H]1O[C@H](CN(C(CO)CO)C2CC(CCc3nc4cc(C(CO)(CO)CO)ccc4[nH]3)C2)[C@@H](O)[C@H]1O] |
| 77 | 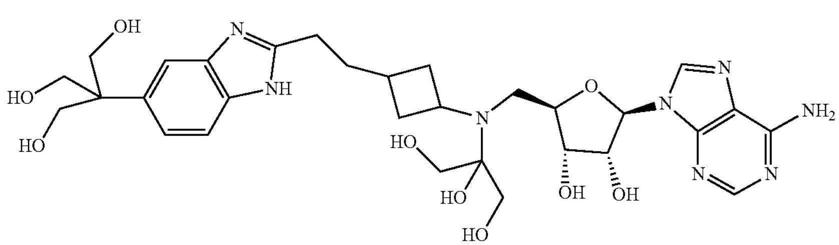 [SMILES: Nc1ncnc2c1ncn2[C@@H]1O[C@H](CN(C2CC(CCc3nc4cc(C(CO)(CO)CO)ccc4[nH]3)C2)C(O)(CO)CO)[C@@H](O)[C@H]1O] |
| 78 | 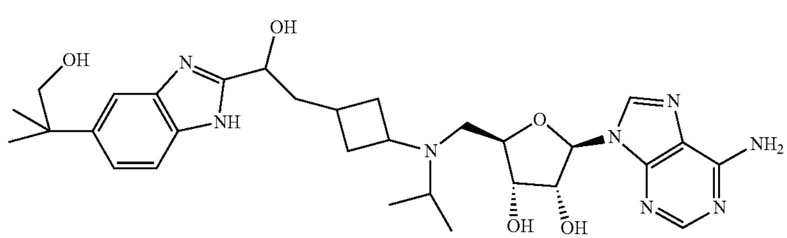 [SMILES: CC(C)N(C[C@H]1O[C@@H](n2cnc3c(N)ncnc32)[C@H](O)[C@@H]1O)C1CC(CC(O)c2nc3cc(C(C)(C)CO)ccc3[nH]2)C1] |

TABLE 1-continued
| Compound no. | Structure |
|---|---|
| 79 | 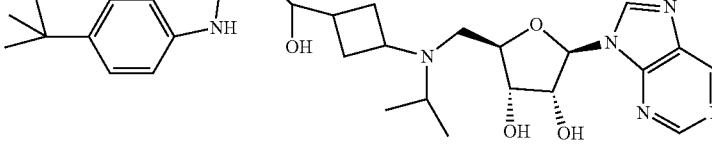 |
| 80 | 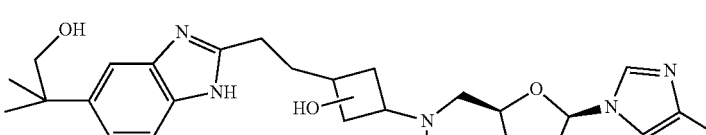 |
| 81 | 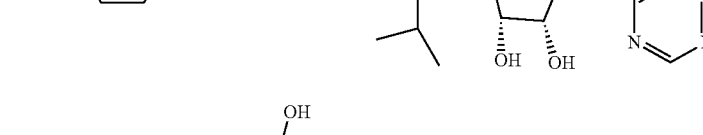 |
| 82 | 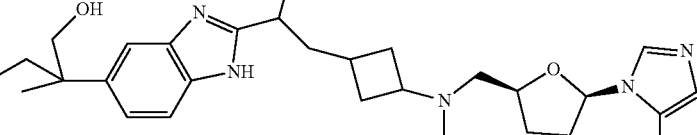 |
| 83 | 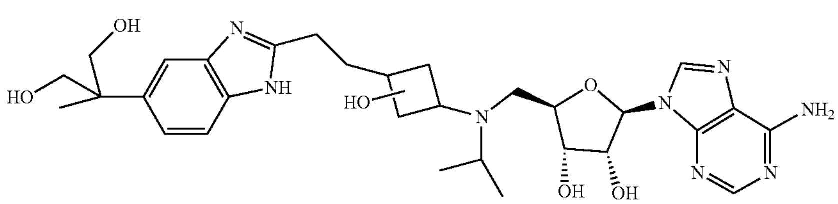 |
| 84 | 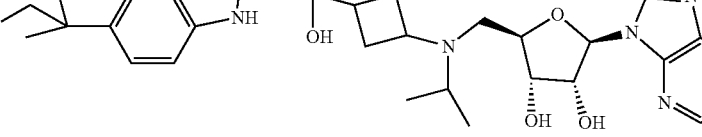 |
| 85 | 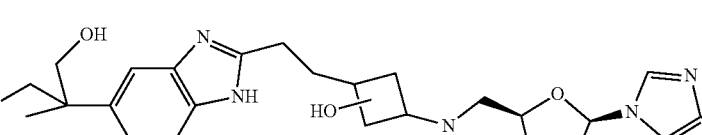 |

TABLE 1-continued

| Compound no. | Structure |
|---|---|
| 86 | *(structure)* |
| 87 | *(structure)* |
| 88 | *(structure)* |
| 89 | *(structure)* |

TABLE 2

| Compound No. | Structure | Nominal mass (Da) | Approx. Retention Time (min) |
|---|---|---|---|
| 101 | *(structure)* | 320 | 10.4 |
| 102 | *(structure)* | 304 | 13.7 |

TABLE 2-continued

| Compound No. | Structure | Nominal mass (Da) | Approx. Retention Time (min) |
|---|---|---|---|
| 103 | 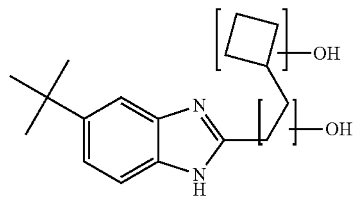 | 288 | 18.5 |
| 104 | 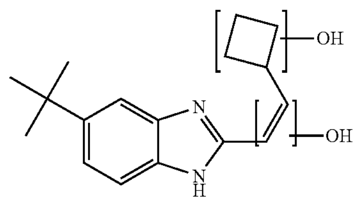 | 286 | 19.6 |
| 105 | 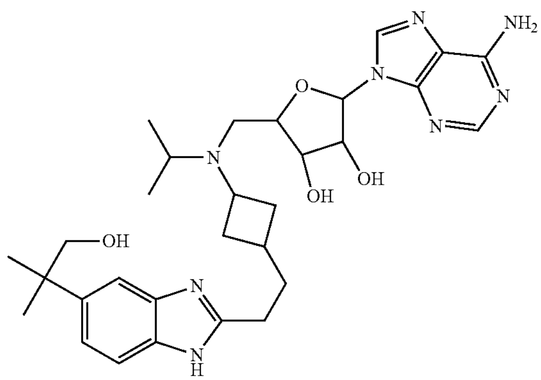 [SMILES: CC(C)N(CC1OC(n2cnc3c(N)ncnc32)C(O)C1O)C1CC(CCc2nc3cc(C(C)(C)CO)ccc3[nH]2)C1] | 578 | 20 |
| 106 | 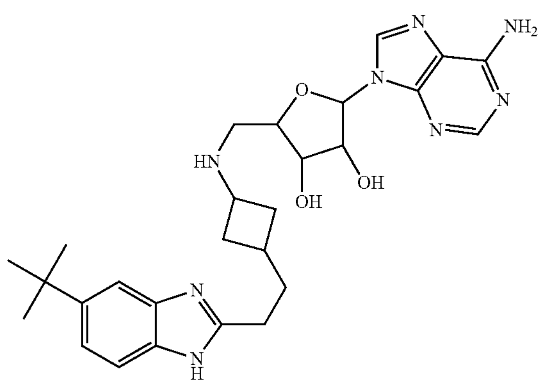 [SMILES: CC(C)(C)c1ccc2[nH]c(CCC3CC(NCC4OC(n5cnc6c(N)ncnc65)C(O)C4O)C3)nc2c1] | 520 | 22.5 |
| 107 | 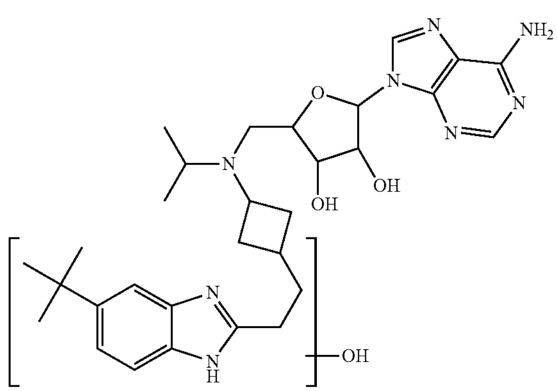 | 578 | 24.5 |

TABLE 2-continued

| Compound No. | Structure | Nominal mass (Da) | Approx. Retention Time (min) |
|---|---|---|---|
| 108 | 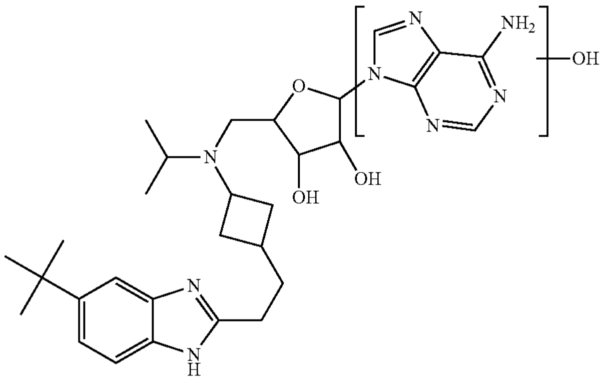 | 578 | 25 |
| A | 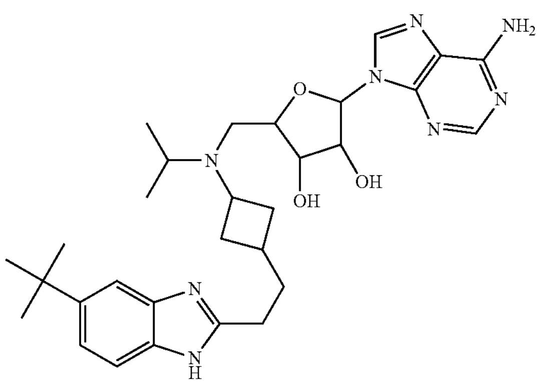 [SMILES: CC(C)N(CC1OC(n2cnc3c(N)ncnc32)C(O)C1O)C1CC(CCc2nc3cc(C(C)(C)C)ccc3[nH]2)C1] | 562 | 26 |
| 109 | 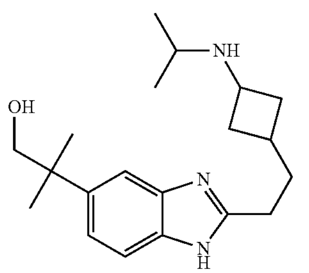 [SMILES: CC(C)NC1CC(CCc2nc3cc(C(C)(C)CO)ccc3[nH]2)C1] | 329 | 28.5 |
| 110 | 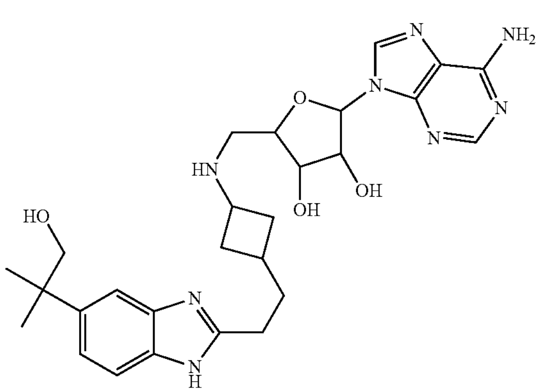 [SMILES: CC(C)(CO)c1ccc2[nH]c(CCC3CC(NCC4OC(n5cnc6c(N)ncnc65)C(O)C4O)C3)nc2c1] | 536 | 18.3 |

TABLE 2-continued

| Compound No. | Structure | Nominal mass (Da) | Approx. Retention Time (min) |
|---|---|---|---|
| 111 | 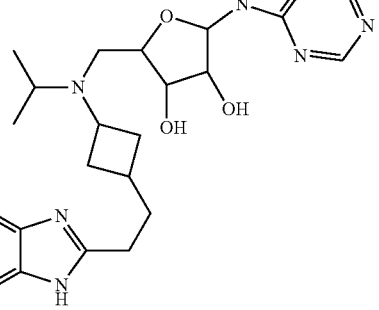 | 592 | 12.8<br>13.2<br>(split peak) |
| 112 | 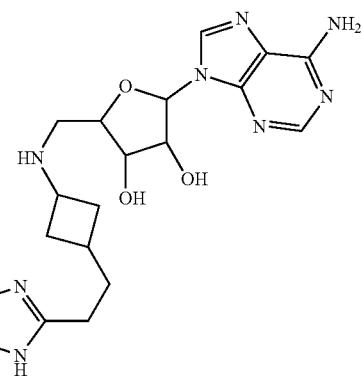 | 550 | 11.3 |
| 113 | 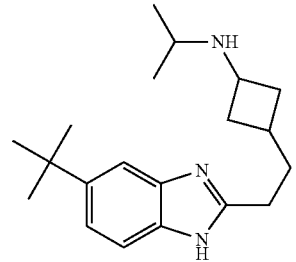 [SMILES: CC(C)NC1CC(CCc2nc3cc(C(C)(C)C)ccc3[nH]2)C1] | 313 | 34.3 |
| 114 | 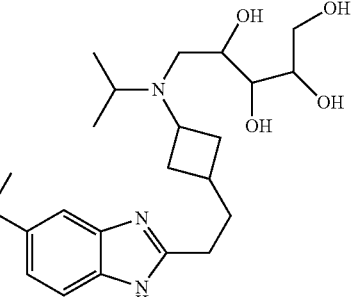 | 447 | 28.7 |

As used herein, the term "isolated" or the expression "in an isolated form" means substantially separated from other components with which the compound may be found as it occurs in nature. A compound can be isolated without necessarily being purified. In one embodiment, the isolated compound of Formula (I) or (II) is a synthesized compound. In another embodiment, the compound of Formula (I) or (II) is a metabolite and is isolated from other components with which the compound may be found as it occurs in a natural environment, e.g., cells of a mammal, e.g., a human or appropriate non-human mammal, such as primate, mouse, rat, dog, cat, cow, horse, goat, and camel. In embodiments, the compound or salt of the present invention has a purity of not less than 40%, not less than 50%, not less than 55%, not less than 60%, not less than 65%, not less than 70%, not less than 75%, not less than 80%, not less than 85%, not less than 90%, not less than 92%, not less than 95%, not less than 97%, or not less than 99%.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. For example, in Formula (I), each hydroxyl of the moiety —(OH)$_1$ can be bonded to any ring atom of the benzimidazole ring (such as a carbon in the benzene ring or a nitrogen atom in the imidazole ring), as long as valence permits and/or the compound thus formed is stable. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

Compounds of the present invention that contain nitrogens include N-oxides (which can be designated as N→O or N$^+$—O$^-$). The N-oxides of the present invention can be generated by, e.g., treating compounds containg nitrogens, e.g., Compound A, with an oxidizing agent (e.g., 3-chloroperoxybenzoic acid (mCPBA) and/or hydrogen peroxides). Furthermore, in other instances, the compounds of the present invention can be N-hydroxy (i.e., N—OH) compounds. For example, N-hydroxy compounds can be prepared by oxidation of the parent amine, e.g., Compound A, by an oxidizing agent such as mCPBA.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. Benzimidazoles also exhibit tautomerism, when the benzimidazole contains one or more substituents in the 4, 5, 6 or 7 positions, the possibility of different isomers arises. For example, 2,5-dimethyl-1H-benzo[d]imidazole can exist in equilibrium with its isomer 2,6-dimethyl-1H-benzo[d]imidazole via tautomerization.

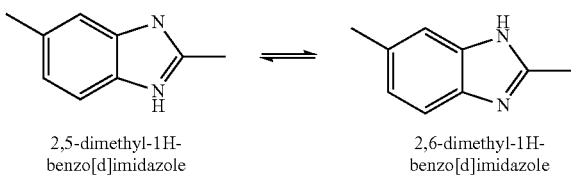

2,5-dimethyl-1H-benzo[d]imidazole      2,6-dimethyl-1H-benzo[d]imidazole

Another example of tautomerism is shown below.

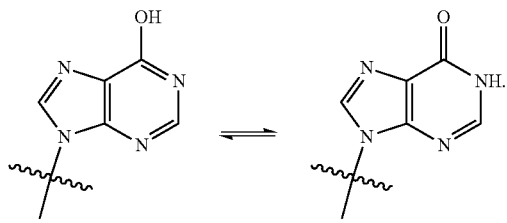 [SMILES: *n1cnc2c(O)ncnc21 ; *n1cnc2c(=O)[nH]cnc21]

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compounds of the invention may be crystalline, semi-crystalline, non-crystalline, amorphous, mesomorphous, etc.

The compounds of any of the Formulae disclosed herein include the compounds themselves, as well as their salts, their solvates, and their prodrugs, if applicable. A salt, for example, can be formed between an anion and a positively charged group (e.g., amino) on the compound or inhibitor (e.g., a substituted nucleoside compound such as a substituted purine compound). Suitable Inions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on the compound or inhibitor (e.g., a substituted nucleoside compound such as a substituted purine compound). Suitable cations include sodium ion, potassium ion, magnesium ion, calcium ion, and an ammonium cation such as tetramethylammonium ion. The compound or inhibitor (e.g., a substituted nucleoside compound such as a substituted purine compound) also include those salts containing quaternary nitrogen atoms. Examples of prodrugs include esters and other pharmaceutically acceptable derivatives, which, upon administration to a subject, are capable of providing active substituted nucleoside compound such as a substituted purine compounds of the invention.

Additionally, the compounds of the present invention, for example, the salts of the compounds, can exist in either hydrated or unhydrated (the anhydrous) form or as solvates with other solvent molecules. Nonlimiting examples of hydrates include hemihydrates, monohydrates, dihydrates, trihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hemihydrate is formed by the combination of one molecule of water with more than one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) or (II) are substituted purine compounds, and have Formula (I) or (II) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The present invention also provides methods for the synthesis of the compounds of any of the Formulae disclosed herein. The present invention also provides detailed methods for the synthesis of various disclosed compounds of the present invention according to the schemes and the Examples described in WO2012/075381, WO2012/075492, WO2012/082436, and WO2012/75500, the contents of which are hereby incorporated by reference in their entireties.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; Greene, T. W., Wuts, P. G. M., *Protective Groups in Organic Synthesis*, 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 3$^{rd}$ edition, John Wiley & Sons: New York, 1999.

Preferred protecting groups include, but are not limited to:
For the hydroxyl moiety: TBS, benzyl, THP, Ac
For carboxylic acids: benzyl ester, methyl ester, ethyl ester, allyl ester
For amines: Cbz, BOC, DMB
For diols: Ac (×2) TBS (×2), or when taken together acetonides
For thiols: Ac
For benzimidazoles: SEM, benzyl, PMB, DMB
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:
AA ammonium acetate
Ac acetyl
ACN acetonitrile
AcOH acetic acid
atm atmosphere
Bn benzyl
BOC tert-butoxy carbonyl
BOP (benzotriazol-1-yloxy)tris(dimethylamino)phosphonium hexafluorophosphate
Cbz benzyloxycarbonyl
COMU (1-cyano-2-ethoxy-2-oxoethylidenaminooxy)dimethylamino-morpholino-carbenium hexafluorophosphate
d days
DBU 1,8-diazabicyclo[5.4.0]undec-7-ene
DCE 1,2 dichloroethane
DCM dichloromethane
DEA diethylamine
DEAD diethyl azodicarboxylate
DIAD diisopropyl azodicarboxylate
DiBAL-H diisobutylalumininium hydride
DIPEA N,N-diisopropylethylamine (Hunig's base)
DMAP N,N-dimethyl-4-aminopyridine
DMB 2,4 dimethoxybenzyl
DMF dimethylformamide
DMSO dimethylsulfoxide
DPPA diphenylphosphoryl azide
EA or EtOAc ethylacetate
EDC or EDCI N-(3-dimethylaminopropyl)-N'-ethylcarbodiimide
ELS Evaporative Light Scattering
ESI– Electrospray negative mode
ESI+ Electrospray positive mode
Et$_2$O diethyl ether Et₃N or TEA triethylamine
EtOH ethanol
FA formic acid
FC flash chromatography
h hours
H₂O water
HATU O-(7-azabenzotriazol-1-yl)-N,N,N',N'-tetramethyluronium hexafluorophosphate
HCl hydrochloric acid
HOAT 1-hydroxy-7-azabenzotriazole
HOBt 1-hydroxybenzotriazole
HOSu N-hydroxysuccinimide
HPLC high performance liquid chromatography
Inj. Vol. injection volume
I.V. or IV intravenous
KHMDs potassium hexamethyldisilazide
LC/MS or LC-MS liquid chromatography mass spectrum
LDA lithium diisopropylamide
LG leaving group
LiHMs lithium hexamethyldisilazide
M Molar
m/z mass/charge ratio
m-CPBA meta-chloroperbenzoic acid
MeCN acetonitrile
MeOD d₄-methanol
MeOH methanol
MgSO₄ magnesium sulfate
min minutes
MS mass spectrometry or mass spectrum
Ms mesyl
MsCl methanesulfonyl chloride
MsO mesylate
MWI microwave irradiation
Na₂CO₃ sodium carbonate
NaHCO₃ sodium bicarbonate
NaHMDs sodium hexamethyldisilazide
NaOH sodium hydroxide
NIS N-iodosuccinimide
NBS N-bromosuccinimide
NCS N-chlorosuccinimide
NMR Nuclear Magnetic Resonance
o/n or O/N overnight
PE petroleum ether
PG protecting group
PKMT protein lysine methyltransferase
PMB para-methoxybenzyl
PMT protein methyltransferase
PPAA 1-propanephosphonic acid cyclic anhydride
ppm parts per million
prep HPLC preparative high performance liquid chromatography
prep TLC preparative thin layer chromatography
p-TsOH para-toluenesulfonic acid
rt or RT room temperature
SAH S-adenosylhomocysteine
SAM S-adenosylmethionine
SAR structure activity relationship
Selectfluor® 1-Chloromethyl-4-fluoro-1,4-diazoniabicyclo[2.2.2]octane bis(tetrafluoroborate), N-Chloromethyl-N'-fluorotriethylenediammonium bis(tetrafluoroborate)
SEM 2-(trimethylsilyl)ethoxymethyl
SEMCl (trimethylsilyl)ethoxymethyl chloride
SFC supercritical chromatography
SGC silica gel chromatography
SPR surface plasmon resonance
STAB sodium triacetoxyborohydride
TBAF tetra-n-butylammonium fluoride
TFA trifluoroacetic acid
TfO triflate
THF tetrahydrofuran
THP tetrahydropyran
TLC thin layer chromatography
Ts tosyl
TsOH tosic acid
UV ultraviolet The invention provides methods for making the compounds of the invention. The following schemes depict exemplary chemistries available for synthesizing the compounds of the invention.

Scheme 1: 5'-Amino Purine Ribose (A-V) Synthesis

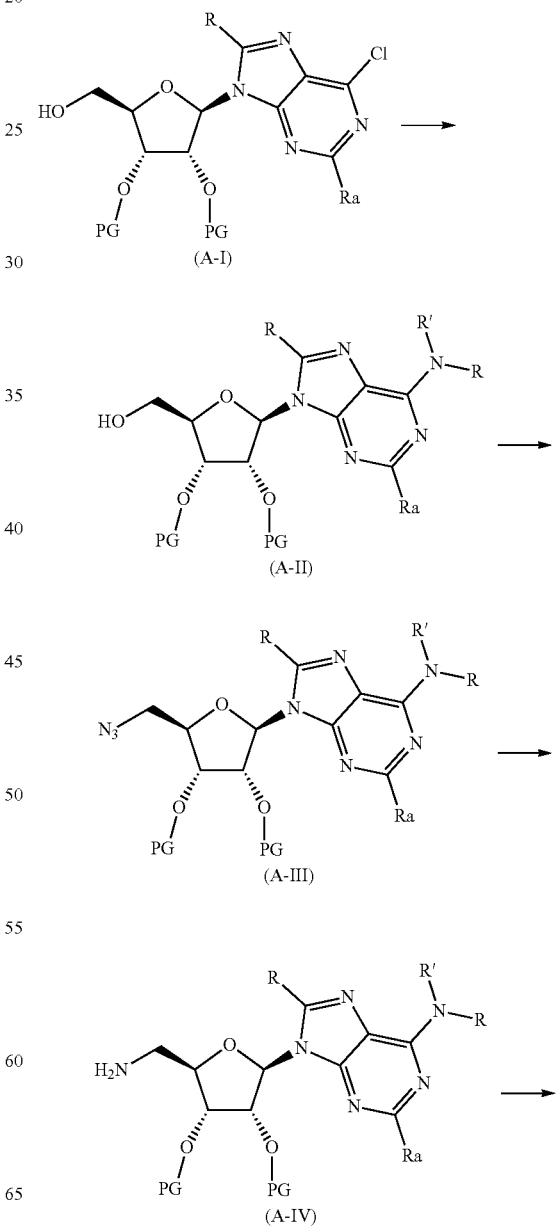

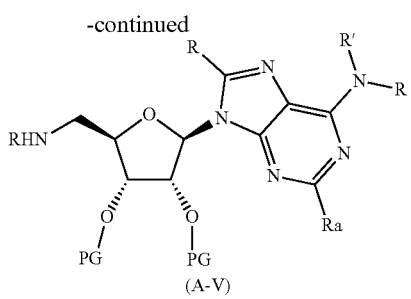

(A-V)

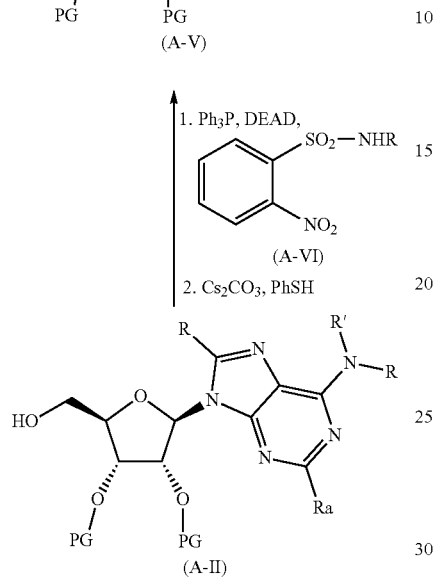

1. Ph₃P, DEAD, (A-VI)

2. Cs₂CO₃, PhSH (A-II)

5'-Amino purine-ribose intermediates (A-V) can be synthesized as depicted in Scheme 1 above. A suitable protected 6-Cl adenosine derivative (A-I) is converted into a 6-amino derivative (A-II) by treatment with the appropriate amine (including ammonia) in the presence of a base such as Et₃N, K₂CO₃ or Hunig's base in solvent such as MeCN or DMF, THF, iPrOH or a mixture thereof. If required, the reaction may be heated to 100° C. (if the temperature required is greater than the boiling point of one or more of the components in the mixture, the reaction may be performed in a sealed tube). The R groups in the scheme may represent alkyl protecting groups (e.g., 2, 4 dimethoxybenzyl). The 6-amino product (A-II) may be transformed into the 5'-azido intermediate (A-III) by converting the 5'-hydroxyl group into a leaving group such as MsO (i.e., CH₃S(O)₂O) by treatment with methanesulfonyl chloride (MsCl) in the presence of a base such as Et₃N, pyridine or K₂CO₃ in an inert solvent such as CH₂Cl₂, THF, MeCN, DMF or a mixture thereof. The 5'-leaving group is then displaced with azide anion from NaN₃ in an inert solvent such as DMF. Alternatively (A-II) may be directly transformed into (A-III) by treatment with DPPA, Ph₃P, and DIAD in a solvent such as THF. The azido group of (A-III) may be reduced to the primary amine (A-IV) by reduction with H₂ in the presence of a metal catalyst (e.g. Pd/C, PtO₂) or by a Staudinger reaction with a phosphine such as Ph₃P or PMe₃. The primary amine (A-IV) may be converted into the secondary amine (A-V) by treatment with the appropriate ketone or aldehyde in the presence of a suitable reducing agent such as NaBH(OAc)₃ or NaCNBH₃. Additional reagents such as Ti(OiPr)4 may be added.

Alternatively the 5'-hydroxy intermediate (A-II) may be treated with the sulfonamide (A-VI), DEAD and Ph₃P in an inert solvent such as THF. The resultant sulfonamide product may then be treated with benzenethiol in the presence of a base such as K₂CO₃, Cs₂CO₃ to give the secondary amine (A-V).

These reaction sequences above may also be applied to lyxose derivatives starting from (A-VII) to give the diastereomer with opposite configuration at the 5' position.

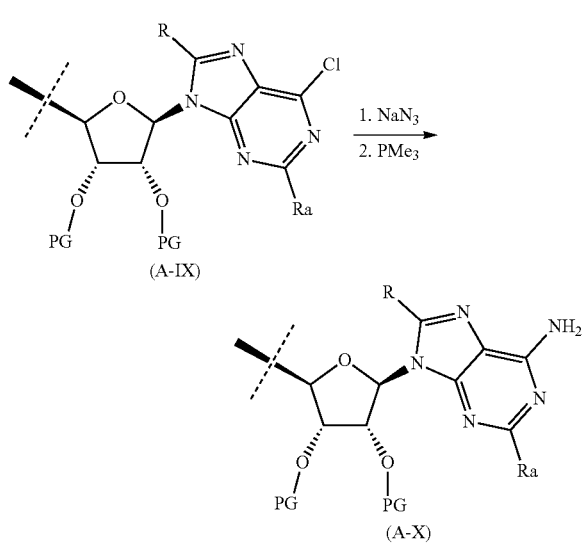

A similar set of reaction sequences may be employed for 2'-deoxy, or 3'-deoxy, or substituted ribose or lyxose (A-VIII) above to obtain 5'-amino purine-ribose/lyxose intermediates.

An alternative method for introduction of a 6-NH₂ group, as shown below, is via treating (A-IX) derivatives with NaN₃ to produce a 6-azido intermediate followed by reduction to the NH₂ moiety (A-X) with a trialkyl phosphine such as PMe₃ or PPh₃.

Scheme 2: Cyclobutane Synthesis
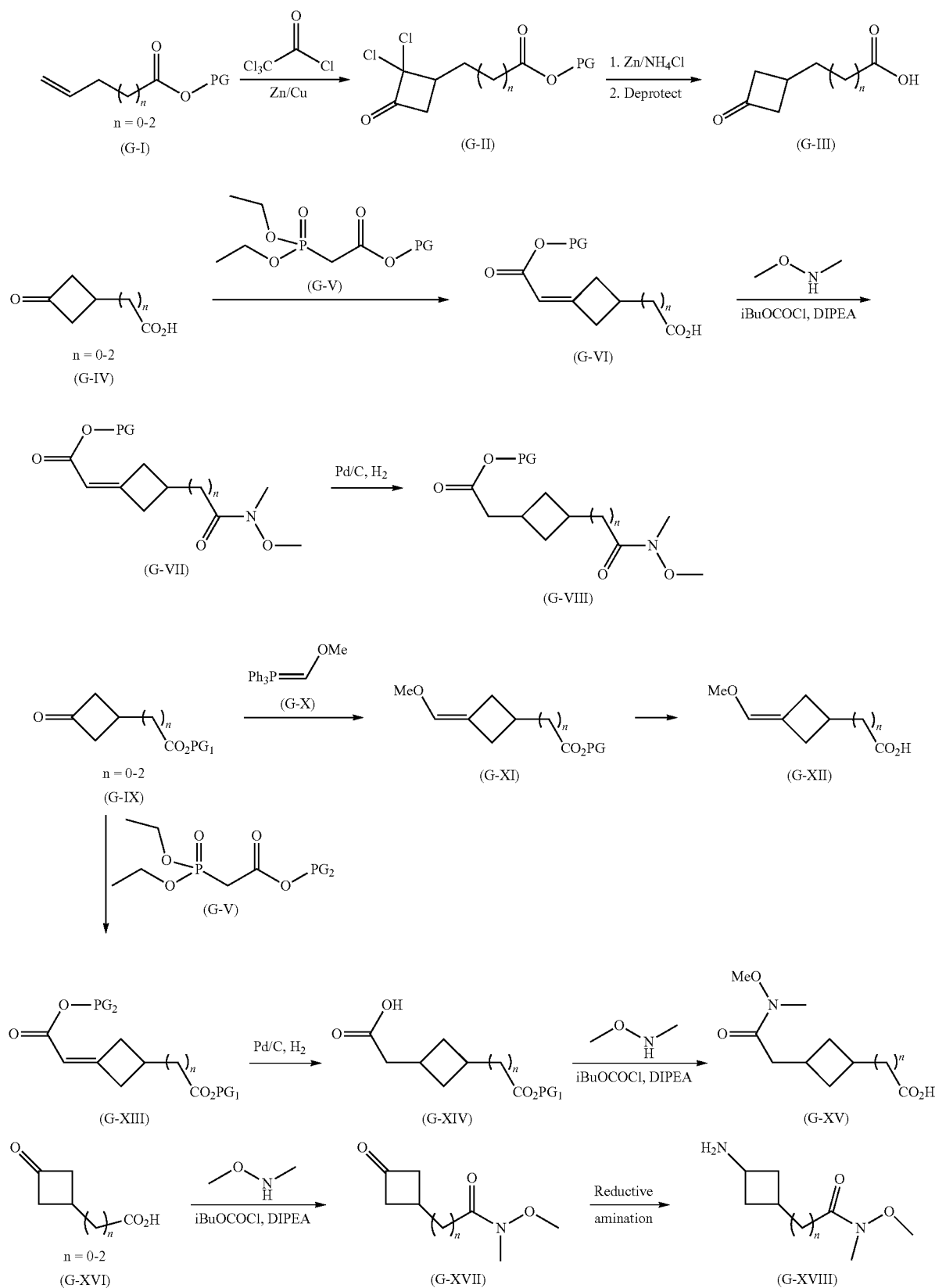

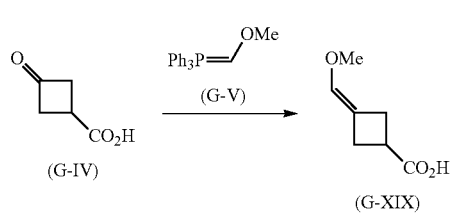
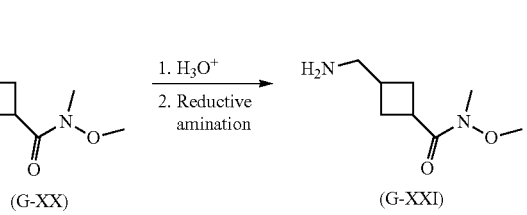

Cyclobutanes of formulae (G-VIII), (G-XV) and (G-XXI) may be synthesized as depicted in Scheme 2. The alkenyl esters (G-I) may be subjected to a [2+2] cycloaddition with trichloroacetyl chloride in the presence of Zn/Cu couple in an inert solvent such as $Et_2O$, DME, THF or a mixture thereof. Alternatively the [2+2] cycloaddition reaction may be performed using Zn dust under sonication conditions. The dichlorides (G-II) are reduced via treatment with Zn powder in the presence of a proton donor such as $NH_4Cl$ in a solvent such as MeOH. The cyclobutanones (G-IV) (which include (G-III)) may be further elaborated by treatment with a phosphonate (G-V) to give the α, β unsaturated esters (G-VI). The acid (VI) is converted to the Weinreb amide (G-VII) under standard conditions (e.g. iso-butyl chloroformate, Hunig's base, N,O-dimethyl hydroxylamine). The double bond may then be reduced via hydrogenation using $H_2$ in the presence of a metal catalyst such as Pd/C, $PtO_2$ or $Pd(OH)_2$ to give the cyclobutane intermediates (G-VIII).

The cyclobutanones (G-IX) may be treated with the Wittig reagent (G-X) to give the cyclobutane enol ether (G-XI) which upon deprotection gives the corresponding acid (G-XII).

The cyclobutanones (G-IX) may also be treated with the stabilized phosphonate (G-V) in the presence of a base such as KOtBu, LDA, NaHMDS, KHMDS or LiHMDS or with $Et_3N$ in the presence of LiCl in an inert solvent to give the α, β unsaturated ester (G-XIII) which can be reduced to the (G-XIV) by treatment with $H_2$ in the presence of a metal catalyst such as Pd/C, $Pd(OH)_2$ or $PtO_2$ in an inert solvent. The acid functionality of (G-XIV) may be converted into the corresponding Weinreb amide by treatment with N,O-dimethylhydroxylamine in presence of a suitable coupling agent such as iso-butylchloroformate and a base such as Hunig's base to give (G-XV).

The cyclobutanones (G-XVI) may also be treated with N,O-dimethylhydroxylamine in presence of a suitable coupling agent such as iso-butylchloroformate and a base such as Hunig's base to give the corresponding Weinreb amide (G-XVII) which upon reductive amination with an ammonia equivalent followed by deprotection as needed gives the amine (G-XVIII). Suitable Immonia equivalents include benzhydryl amine, $NH_3$, $NH_4Cl$, $BnNH_2$, $PMB-NH_2$, 2,4 $DMB-NH_2$ which may be treated with the ketone (G-XVII) and a suitable reducing agent such as $NaCN(BH_3)$ or $Na(OAc)_3BH$ in the presence of an acid if required such as HCl or AcOH. Protecting groups on the reductive amination products may be removed by methods known to those of ordinary skill in the art. Alternatively the ketone (G-XVII) can be treated with hydroxyl amine to form the corresponding oxime which then can be reduced with $H_2$ in the presence of a metal catalyst such as Pd/C, $PtO_2$ or $Pd(OH)_2$ to give the intermediate (G-XVIII).

The cyclobutane (G-IV) may converted into the amine (G-XXI) via a multi-step sequence involving treating (G-IV) with the phosphorane (G-V) to produce the enol ether (G-XIX). Treatment of (G-XIX) with which is then N,O-dimethylhydroxylamine in presence of a suitable coupling agent such as iso-butyl chloroformate and a base such as Hunig's base to give the corresponding Weinreb amide (G-XX) which after aqueous hydrolysis of the enol ether (e.g. $TsOH/H_2O$, $HCl/H_2O$) and reductive amination with an ammonia equivalent followed by deprotection as needed gives the amine (G-XXI). Suitable Immonia equivalents include benzhydryl amine, $NH_3$, $NH_4Cl$, $BnNH_2$, $PMB-NH_2$, 2,4 $DMB-NH_2$. Suitable reducing agents for the reductive amination include $NaCN(BH_3)$ or $Na(OAc)_3BH$ used in the presence of an acid if required such as HCl or AcOH. Protecting groups on the reductive amination products may be removed by methods known to those of ordinary skill in the art.

Scheme 3: Coupling of Cyclobutanes to Amines

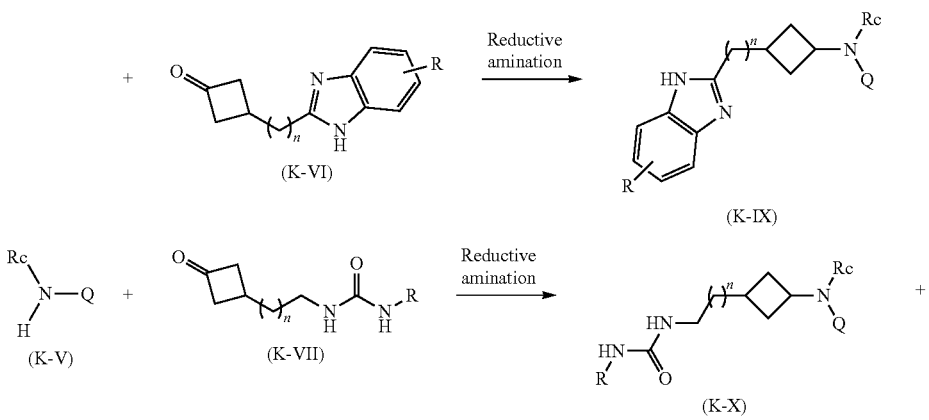

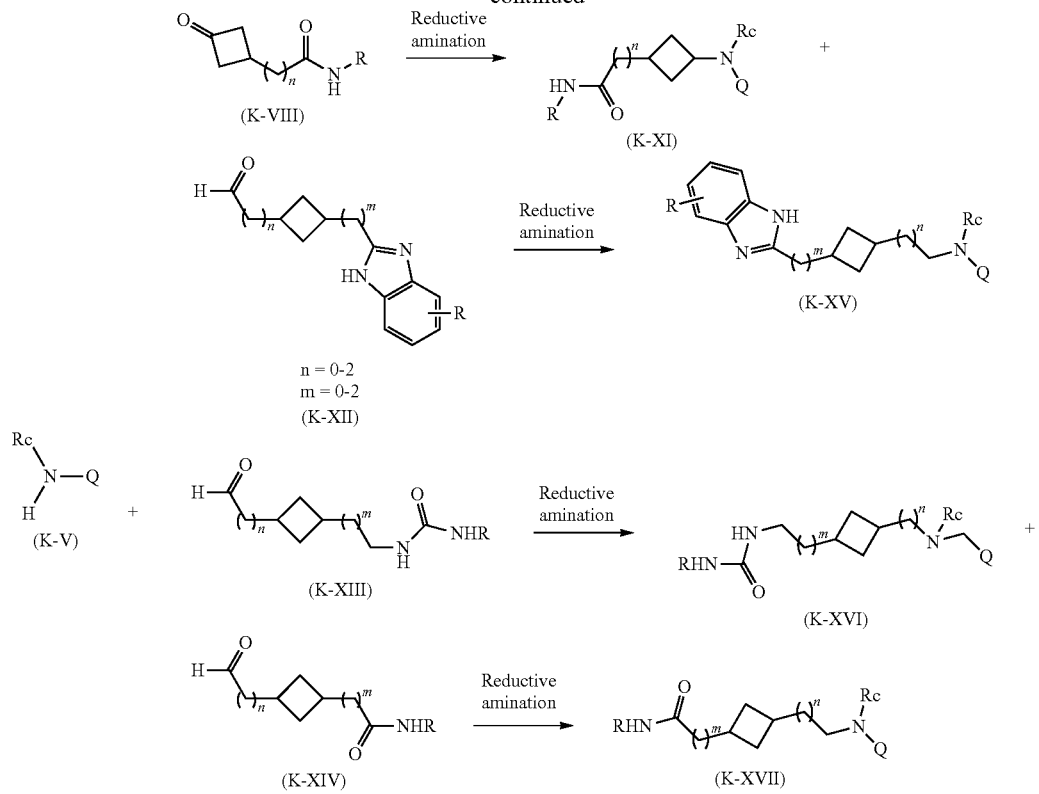

n = 0-2
m = 0-2

The formula (K-V)

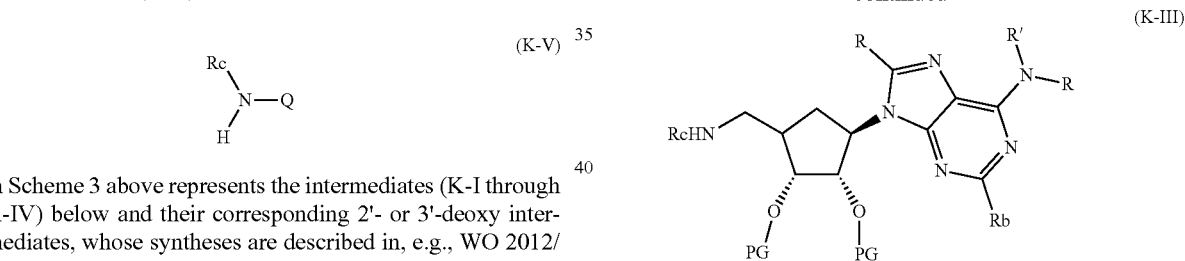

in Scheme 3 above represents the intermediates (K-I through K-IV) below and their corresponding 2'- or 3'-deoxy intermediates, whose syntheses are described in, e.g., WO 2012/075381.

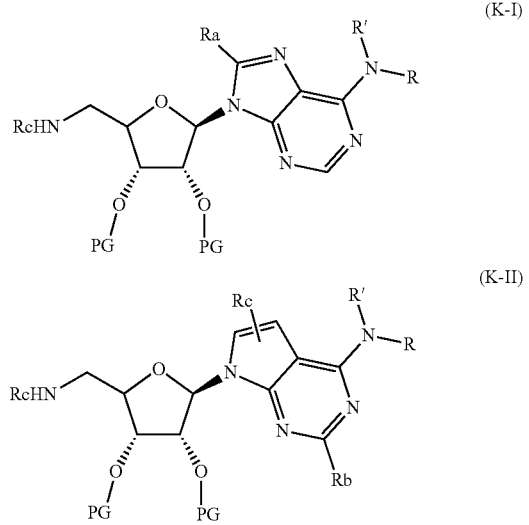

As shown in Scheme 3, the ketones (K-VI), (K-VII) and (K-VIII) and the aldehydes (K-XII), (K-XIII) and (K-XIV) are converted into the corresponding benzimidazoles (K-IX) and (K-XV), ureas (K-X) and (K-XVI) and amides (K-XI) and (K-XVII) via reductive amination with (K-V). The reductive amination can be performed with a suitable reducing agent such as $NaCN(BH_3)$ or $Na(OAc)_3BH$ in the presence of an acid if required such as HCl or AcOH or a Lewis acid/dehydrating agent such as $Ti(OiPr)_4$ or $MgSO_4$.

In one embodiment, Compound A may be synthesized by routes depicted in scheme 1A below. The process is a 4-step synthesis including a purification step to produce pure Compound A: (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof. More detailed synthetic disclosure can be found in, e.g., co-owned U.S. application Ser. No. 14/210,888, filed Mar. 14, 2014, the content of which is hereby incorporated by reference in its entirety. The variables in the chemical formula included in Scheme 1A (e.g., $R_1$, $R_2$, l', m', n', p', q', r', t', u', v', and w' are as defined herein for Formula II).

Scheme 1A

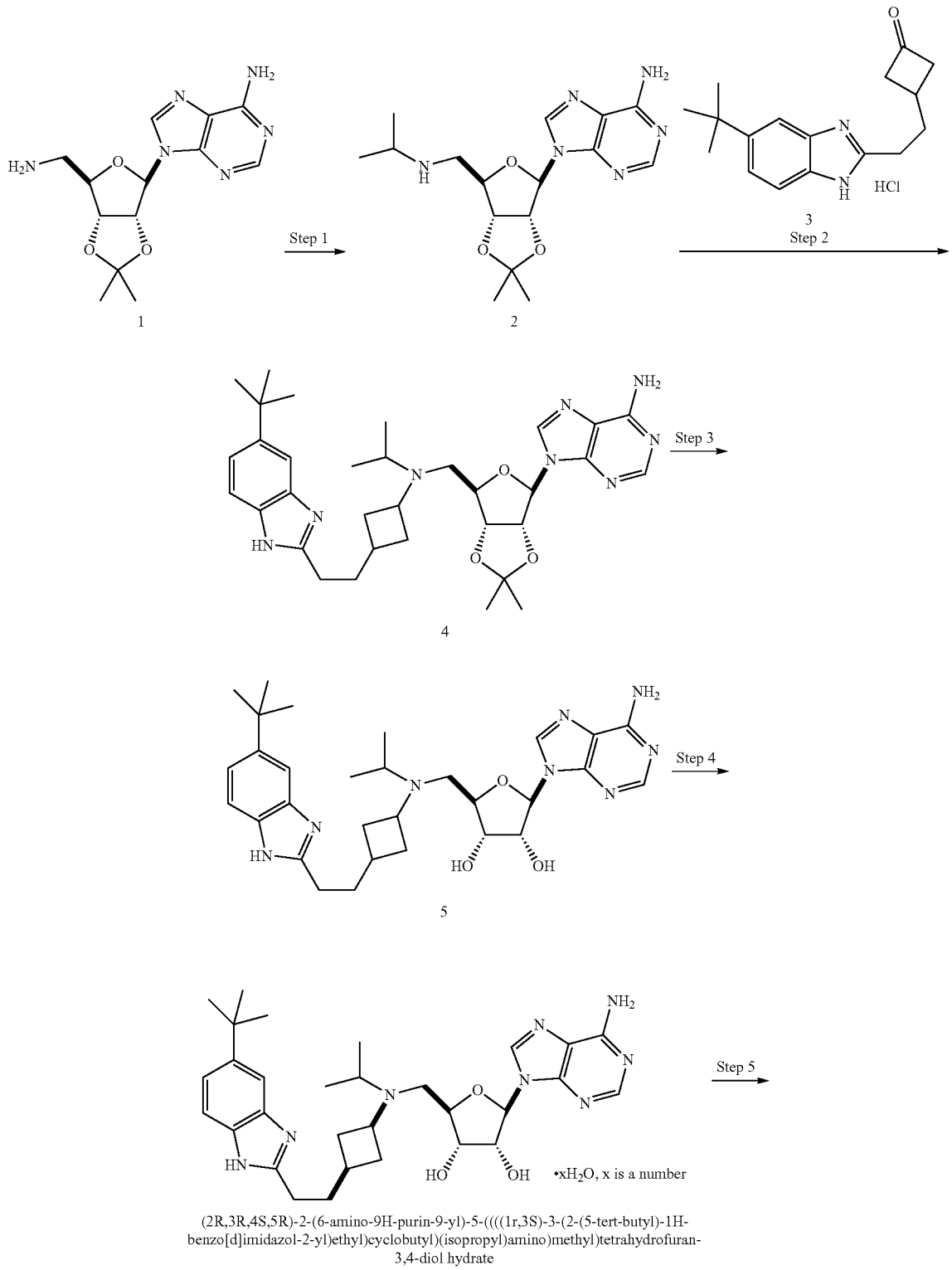

(2R,3R,4S,5R)-2-(6-amino-9H-purin-9-yl)-5-((((1r,3S)-3-(2-(5-tert-butyl)-1H-benzo[d]imidazol-2-yl)ethyl)cyclobutyl)(isopropyl)amino)methyl)tetrahydrofuran-3,4-diol hydrate -continued

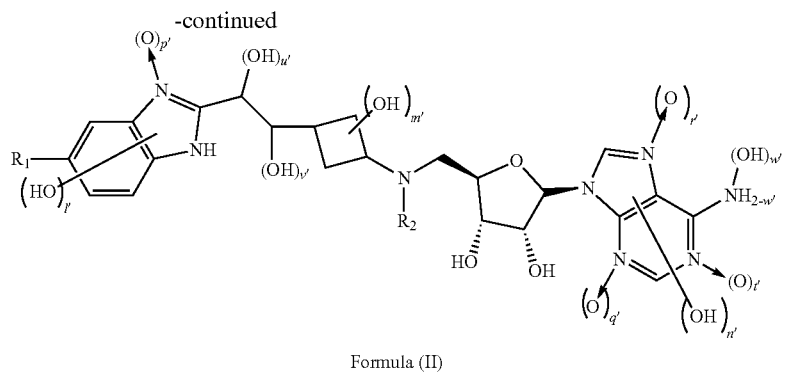

Formula (II)

Compounds of the invention, such as those selected from compounds 1-89, 101-104, and 107-114 and pharmaceutically acceptable salts thereof, can be synthesized via methods similar to those for Compound A. In some embodiments, compounds of the invention, such as N-oxides or N-hydroxy compounds of Compound A can be synthesized by oxidizing Compound A with an oxidizing agent such as mCPBA, for example, step 5 of Scheme 1A above is an oxidization step. In some embodiments, a compound of the invention, such as a monohydroxylated-Compound A, is produced via enzymatic reactions either in vivo or in vitro, for example, step 5 of Scheme 1A above is an in vivo or in vitro metabolization step. In other embodiments, a hydroxylated-Compound A, is synthesized via a multi-step reaction, e.g., step 5 of Scheme 1A above includes multiple steps with suitable reaction conditions to afford the hydroxylated compound of interest. In some embodiments, a compound of the invention, such as Compound No. 111, is produced via oxidation, for example, step 5 of Scheme 1A above includes either chemical or enzymatic reactions or combination thereof to oxidize Compound A to a corresponding carboxylic acid. In some embodiments, a compound of the invention, such as Compound No. 110 or 112, is produced via dealkylation and hydroxylation or oxidation, for example, step 5 of Scheme 1A above includes either chemical or enzymatic reactions or combination thereof to (i) afford the corresponding dealkylated Compound A and then the corresponding hydroxylated compound or carboxylic acid, or (ii) to afford the corresponding hydroxylated compound or carboxylic acid and then the corresponding dealkylated compound.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions can be conducted simultaneously.

Compounds suitable for the methods of the invention, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described herein.

To further assess a compound's drug-like properties, measurements of inhibition of cytochrome P450 enzymes and phase II metabolizing enzyme activity can also be measured either using recombinant human enzyme systems or more complex systems like human liver microsomes. Further, compounds can be assessed as substrates of these metabolic enzyme activities as well. These activities are useful in determining the potential of a compound to cause drug-drug interactions or generate metabolites that retain or have no useful antimicrobial activity.

To get an estimate of the potential of the compound to be orally bioavailable, one can also perform solubility and Caco-2 assays. The latter is a cell line from human epithelium that allows measurement of drug uptake and passage through a Caco-2 cell monolayer often growing within wells of a 24-well microtiter plate equipped with a 1 micron membrane. Free drug concentrations can be measured on the basolateral side of the monolayer, assessing the amount of drug that can pass through the intestinal monolayer. Appropriate controls to ensure monolayer integrity and tightness of gap junctions are needed. Using this same system one can get an estimate of P-glycoprotein mediated efflux. P-glycoprotein is a pump that localizes to the apical membrane of cells, forming polarized monolayers. This pump can abrogate the active or passive uptake across the Caco-2 cell membrane, resulting in less drug passing through the intestinal epithelial layer. These results are often done in conjunction with solubility measurements and both of these factors are known to contribute to oral bioavailability in mammals. Measurements of oral bioavailability in animals and ultimately in man using traditional pharmacokinetic experiments will determine the absolute oral bioavailability.

Experimental results can also be used to build models that help predict physical-chemical parameters that contribute to drug-like properties. When such a model is verified, experimental methodology can be reduced, with increased reliance on the model predictability.

The present invention also provides pharmaceutical compositions comprising a compound of any of the Formulae disclosed herein in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug interaction(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g, a methyl, ethyl or other ester. Also, an alcohol group in a compound can be converted to its corresponding ester, e.g., acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, N.Y.-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers.

Compounds described herein are assayed for modulation of activity, for example, histone methylation, modulation of cell growth and/or $IC_{50}$, described in the examples below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLE 1

Synthesis and/or Isolation of Compounds

Compound A was synthesized by the methods described in WO 2012/075381 or co-owned U.S. Provisional Application Ser. No. 61/799,147, filed Mar. 15, 2013, the contents of which are hereby incorporated by reference in their entireties.

Compounds of the invention, such as those selected from compounds 1-89, 101-104, and 107-114 and pharmaceutically acceptable salts thereof, can be synthesized via methods similar to those for Compound A. Certain compounds in Table 1 or 2, such as N-oxides of Compound A can be synthesized by oxidizing Compound A with an oxidizing agent such as mCPBA.

Compounds of the invention, such as metabolites of Compound A, can also be generated by separating these compounds from their naturally occurring environment, by e.g., chromatography, methods described herein, or other known purification methods.

EXAMPLE 2

Preclinical Pharmacokinetic Evaluation of Compound A

Compound A: ((2R,3R,4S,5R)-2-(6-(amino-9H-purin-9-yl)-5-((((1r,3S)-3-(2(5-(tert-butyl)-1H-benzo[d]imidazol-2-yl)ethyl)cyclobutyl)(isopropyl)amino)methyl)tetrahydrofuran-3,4-diol) is a DOT1L histone methyltransferase inhibitor currently in development for the treatment of MLL-rearranged leukemias. Described below are the preclinical pharmacokinetics and metabolism studies conducted for Compound A, an aminonucleoside analog with exquisite target potency and selectivity that has shown robust and durable tumor growth inhibition in preclinical models. The in vivo pharmacokinetics in mouse, rat and dog were characterized and applied to the prediction of human PK parameters and exposure, using various interspecies scaling approaches. Preclinical pharmacokinetics indicates Compound A has moderate CL with a steady-state volume of distribution 2-3 fold higher than total body water. Corresponding in vitro ADME parameters were also studied and utilized for in vitro-in vivo extrapolation purposes. There was reasonable congruence between microsomal CL and in vivo CL implicating hepatic oxidative metabolism as the predominant elimination route in preclinical species. The metabolic pathways across species were studied in liver microsomes in which Compound A was metabolized to three monohydroxylated metabolites (Compounds M1, M3 and M5), one N-dealkylated product (Compound M4) as well as an N-oxide (Compound M6). None of the metabolites detected in this milieu were unique to human. This first-in-class DOT1L inhibitor with promising therapeutic potential in MLL-rearranged leukemias is currently in Phase 1 clinical trials.

Compound A inhibits DOT1L with a Ki of 80 pM and displays 37,000-fold selectivity over a panel of other HMTs. Potency was further exemplified by treatment in a rat xenograft model of MLL-rearranged leukemia with Compound A, in which continuous intravenous (IV) infusion of Compound A caused complete tumor regressions that were sustained beyond the compound infusion period with no significant weight loss or signs of toxicity (Daigle et al., Potent Inhibition of DOT1L as Treatment for MLL-Fusion Leukemia. *Blood* 2013; 122(6): 1017-1025).

Understanding of the pharmacokinetic properties along with the remarkable potency of Compound A both in vitro and in vivo promoted the development of this molecule for acute leukemias bearing MLL-rearrangements. Compound A is currently in Phase I evaluation and represents not only the first reported histone methyltransferase inhibitor to enter human clinical trials, but a further step in understanding the link between epigenetic processes and the pathophysiology of cancer.

Methods

Chemicals and Reagents

Compound A was synthesized by Epizyme (Daigle et al., *Blood* 2013; 122(6): 1017-1025). All other reagents were purchased from sources as described below.

In Vivo Pharmacokinetics

All animal studies were conducted in accordance with local IACUC standards.

Pharmacokinetic study in mouse. Pharmacokinetics of Compound A was evaluated in male CD1-mice (28-29 grams, male, n=21, purchased from BK Laboratory Animal Co. LTD) following IV bolus administration of doses of 5 mg/kg and oral administration at doses of 20 mg/kg. Oral and IV doses were administered by oral gavage, or by tail vein injection in a 10% ethanol and 90% saline vehicle, respectively. For PO dosing, samples were taken at 0.167, 0.5, 1, 2, 4, 6 and 24 h p.d. For IV administration, samples were taken at 0.05, 0.167, 0.5, 1, 2, 4, 6 and 24 h p.d. Blood samples were centrifuged at 4° C. (2000 g, 5 minutes) to obtain plasma within 15 minutes after sample collection. The levels of Compound A were quantitated in mouse plasma by LC-MS/MS analysis.

Pharmacokinetic study in rat. Pharmacokinetics of Compound A was evaluated in Sprague-Dawley rats (male, n=3 for IV bolus and PO studies and n=6 for IV infusion study), purchased from either SLAC Laboratory Animal Co. LTD (IV bolus), Vital River Laboratory Animal Co. LTD (PO study), or Charles River Canada Inc., St. Constant, QC, Canada (IV infusion). In the IV bolus study, 1 mg/kg doses prepared in 0.4% HPBCD in saline were administered via foot dorsal vein injection. At each timepoint, 150 µL of blood was collected via tail vein into EDTA-$K_2$ tubes. The blood samples were maintained in wet ice initially and centrifuged to obtain plasma (2000 g, 4° C., 5 minutes) within 15 minutes post sampling. In the PO study, doses prepared in 10% Ethanol:5% Solutol HS15:85% (5% of dextrose in water) were administered by oral gavage. Samples were collected as described above. In the IV infusion study, doses were prepared in 10% PEG400 in 0.9% saline and administered into the femoral vein, at a dose of 4.7 mg/kg/day for 7 days. 500 µL of blood was collected by jugular venipuncture at timepoints over 7 days and placed on crushed wet ice until centrifugation, which was carried out as soon as practical. The samples were centrifuged for 10 minutes at 4° C. at 2700 rpm. The resultant plasma was separated and frozen immediately over dry ice for LC-MS/MS analysis.

Pharmacokinetic study in dog. Intravenous (IV) pharmacokinetics of Compound A was evaluated in beagle dogs (male, n=3, purchased from Beijing Marshall Biotechnology Co. Ltd.) following a single IV administration at a dose of 1 mg/kg. IV doses were administered by a single intravenous infusion over 1 minute into the cephalic vein in a 10% ethanol and 90% saline vehicle. At designated time points (predose, 0.083, 0.25, 0.5, 1, 2, 4, 8 and 24 h p.d.), the animals were restrained manually, and approximately 0.5 mL blood per time point was collected from non-injected cephalic vein into pre-cold EDTA-$K_2$ tubes. Blood samples were put on wet ice and centrifuged at 4° C. to obtain plasma within 15 minutes of sample collection. The levels of Compound A were quantitated in dog plasma by LC-MS/MS analysis.

LC-MS/MS Bioanalysis & Pharmacokinetic Data Analysis

Compound A was extracted from $K_2$EDTA plasma by protein precipitation using an acetonitrile-containing internal standard (a structural analog of Compound A at a concentration of 5 ng/mL). Typically, samples were injected onto an LC-MS/MS system using a Waters BEH Phenyl column. The aqueous mobile phase was water with 0.1% $NH_4OH$ (A), and the organic mobile phase was acetonitrile with 0.1% $NH_4OH$ (B). The gradient was as follows: 37% B for the first 0.2 min, increased to 44% B from 0.2 to 0.6 min, maintained at 44% B for 0.5 min, and decreased to 37% B within 0.05 min. The injection volume was 2 µL, and the total run time was 1.5 min with a flow rate of 0.6 mL/min. The retention time of Compound A was 0.85 min. The ionization was conducted in the positive ion mode using the MRM transition [M+H]+m/z 563.5 parent ion to m/z 326.3 daughter ion, incorporating a turbo-ionspray interface. Eight to ten calibration standards were prepared in blank plasma of the relevant species providing a typical standard curve concentration range of 5-500 ng/mL.

Pharmacokinetic parameters were calculated by noncompartmental methods using WinNonlin (version 5.3; Pharsight, St. Louis, Mo.). Parameters are presented as mean±S.D.

In Vitro Stability Assays in Liver Microsomes and Hepatocytes

Liver microsomes (final protein concentration 0.5 mg/mL), 0.1 M phosphate buffer at pH 7.4 and Compound A (final concentration of 3 µM; final DMSO concentration of 0.25%) were pre-incubated at 37° C. prior to the addition of NADPH (final concentration of 1 mM) to initiate the reaction. The final incubation volume was 50 µL. Control incubations were included for each species where 0.1 M phosphate buffer pH 7.4 was added instead of NADPH (minus NADPH). Two control compounds were included for each species. Compound A and controls were incubated for 0, 5, 15, 30 and 45 minutes. The control (minus NADPH) was incubated for 45 minutes only. The reactions were stopped by transferring 25 µL of incubate to 50 µL methanol at the appropriate time points. The incubation plates were centrifuged at 2,500 rpm for 20 minutes at 4° C. to aid protein precipitation.

Human, Beagle dog, Sprague-Dawley rat, and CD-1 mouse cryopreserved hepatocytes were obtained from XenoTech and stored at −150° C. until use. The hepatocytes were thawed and prepared according to the vendor's instructions, pooled into Krebs Henseleit buffer (KHB, pH 7.4), and kept on ice prior to initiating an experiment. The hepatocyte suspensions were pre-incubated in a shaking water bath at 37° C. for 3 minutes, and then the reaction was initiated by addition of Compound A into the hepatocyte suspensions (1.5×106 cells/mL) at a final concentration of 3 µM, and a DMSO content of 0.1%. The reaction mixture was incubated in a shaking water bath at 37° C. Aliquots of the incubation solutions were sampled at 0, 15, 30, 60, and 120 minutes. The reaction was immediately terminated by the addition of three volumes of ice-cold acetonitrile containing 0.1% formic acid and internal standards. After centrifugation at 1640×g for 10 minutes, the supernatants were transferred into HPLC vials, and the test compound was analyzed by LC-MS/MS. Positive controls, testosterone (20 µM) and 7-hydroxycoumarin (100 µM), were performed in parallel to confirm the enzyme activities of the hepatocytes used.

Experimental half-lives were transformed to the corresponding intrinsic clearance values and subsequently scaled to predicted in vivo clearance values, using the well-stirred model as previously described (Houston, *Biochemical Pharmacology* 47(9): 1469-1479, 1994; Obach, *Drug Metabolism and Disposition* 27(11): 1350-1359, 1999), with appropriate species-specific scaling factors (Barter et al., *Current Drug Metabolism* 8(1): 33-45, 2007).

Plasma Protein Binding, Blood Partitioning and Plasma Stability Assays

Plasma protein binding was assessed by equilibrium dialysis, utilizing the HT-dialysis cell format with a cellulose semi permeable membrane (molecular weight cut off of 5000 Da). Plasma was warmed to 37° C. and adjusted to pH 7.4 before use. Male Sprague-Dawley rat, male Beagle dog, male CD-1 mouse and mixed sex human plasma was used for the studies. A 5 µM test compound solution was prepared in isotonic phosphate buffer and rat, dog, mouse and human plasma (final DMSO concentration of 0.5%). The plasma-containing solution was introduced to one side of the membrane, and the plasma-free on the other. Incubations were performed for 2-16 hours in duplicate in order to allow the compound to reach equilibrium. Haloperidol was included as the control compound for each species. At the end of the equilibration time the cells were emptied. Following protein precipitation, the samples were centrifuged and analyzed by LC-MS/MS. The samples from the protein containing compartment were quantified using calibration standards prepared in plasma and the protein free compartments were quantified using calibration standards prepared in dialysis buffer.

For blood partitioning, Male Sprague Dawley rat blood was sourced from Harlan Sera-Lab Limited, Loughborough, UK. The haematocrit was measured using a Hettich Haematokrit 210 and calculated as the percentage of packed cell volume compared to total volume of whole blood. Compound A (final test compound concentration 0.5 µM, final DMSO concentration 0.05%) was incubated separately with fresh heparinized whole blood, reference red blood cells and reference plasma for 60 min at 37° C. Following incubation, the whole blood cell samples were centrifuged for 5 min at 5,000 g at 4° C. The spiked reference plasma was stored on ice during this period. The spiked reference red blood cells were freeze thawed quickly three times to assist in lysing the red blood cells. Following centrifugation of the whole blood experimental sample, an aliquot was sampled from the plasma and red blood cell layers for analysis. As before, the red blood cell layer was freeze thawed quickly three times to lyse the red blood cells. After protein precipitation and centrifugation, the supernatants for the experimental samples and reference samples were analyzed by LC-MS/MS. Blood-to-plasma ratios were calculated as previously described (Hinderling, *Pharmacological Reviews* 49(3): 279-295, 1997).

For plasma stability, Compound A (1 µM) was incubated with pooled lots of human, Beagle dog Sprague Dawley rat and CD-1 mouse plasma for 0, 15, 30, 60 and 120 min at 37° C. Samples were quenched in methanol and analyzed by LC-MS/MS analysis.

MDCK Cell Permeability Assays

Confluent monolayers of MDCK or MDR1-MDCK (P-glycoprotein) cells, 7-14 days old, in Transwell® dual-chamber plates, with apical and basolateral pH 7.4 were dosed on the apical side (A-to-B) or basolateral side (B-to-A) with Compound A (10 uM) and incubated at 37° C. with 5% $CO_2$ in a humidified incubator. Samples were taken from the donor and receiver chambers at 120 minutes. Each determination was performed in duplicate. Co-dosed lucifer yellow flux was also measured for each monolayer to ensure cell monolayers remained intact during the incubation. All samples were assayed by LC-MS/MS.

Compound Identification

Compound A was incubated with liver microsomes of various species (mouse, rat, dog or human). In vitro metabolite profiling and identification were conducted after incubating Compound A (final concentration of 10 µM) with mouse, rat, dog or human liver microsomes (final protein concentration of 0.5 mg/mL) at 37° C. in 100 mM potassium phosphate buffer containing 2 mM $Mg^{2+}$ in the presence of NADPH and UDPGA (with addition of 0.1 mg/mL alamethacin to human and rat microsomes). For all liver microsomal incubations, samples were taken at 0 and 20 minutes. All samples were quenched by using acetonitrile/methanol solution and analyzed using an LC-MS/MS Q-Trap system (AB Sciex, Framingham, Mass.).

The major metabolites of Compound A in terms of the mass spectrometry response were identified by comparison of the LC-MS total ion chromatograms (TIC) of 0 minute and 20 minute samples in full scan mode using LightSight™ 2.0 software. The corresponding product ion tandem mass spectra of Compound A and its metabolites were obtained by using enhanced product ion (EPI) scans during positive ion electrospray. The possible chemical structures of the metabolites were deduced based on their MS1 and MS2 spectra.

Prediction of Human Pharmacokinetics Using Preclinical Species

PK endpoints of CL and VDss in mouse, rat and dog were used to scale to the corresponding parameters in human using a variety of allometric and interspecies scaling approaches as previously reported (Boxenbaum, *Journal of Pharmacokinetics and Biopharmaceutics* 10(2): 201-227, 1982; Jones et al., *Journal of Pharmaceutical Sciences* 100(10): 4074-4089, 2011; Lombardo et al., *J Clin Pharmacol* 53(2): 178-191, 2013a; Lombardo et al., *J Clin Pharmacol* 53(2): 167-177, 2013b; Mahmood & Balian, *Xenobiotica* 26(9): 887-895, 1996; Ring et al., *Journal of Pharmaceutical Sciences* 100(10): 4090-4110, 2011; Tang & Mayersohn, *Journal of Pharmaceutical Sciences* 95(8): 1783-1799, 2006; Tang & Mayersohn, *Drug Metabolism and Disposition* 33(9): 1297-1303, 2005; Vuppugalla et al., *Journal of Pharmaceutical Sciences* 100(10): 4111-4126, 2011). The likely predictive accuracy of each method was assessed based on visual inspection of the data fit, as well as values such as the $R^2$ and the allometric exponent, where appropriate.

In Vivo Pharmacokinetics

Figure 1B:
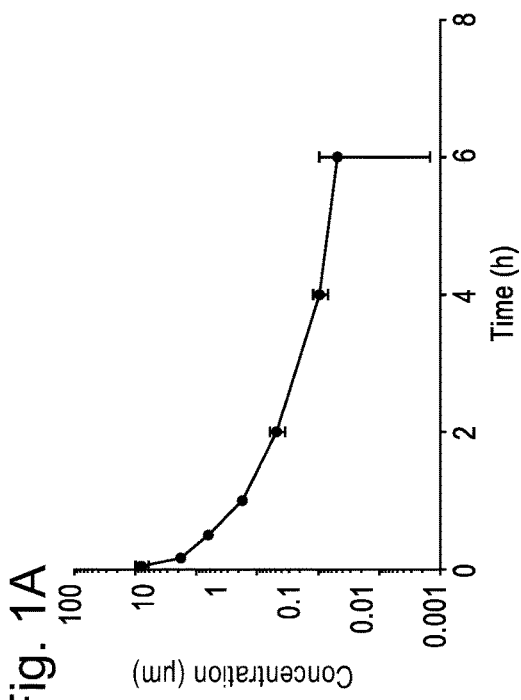
Figure 1C:
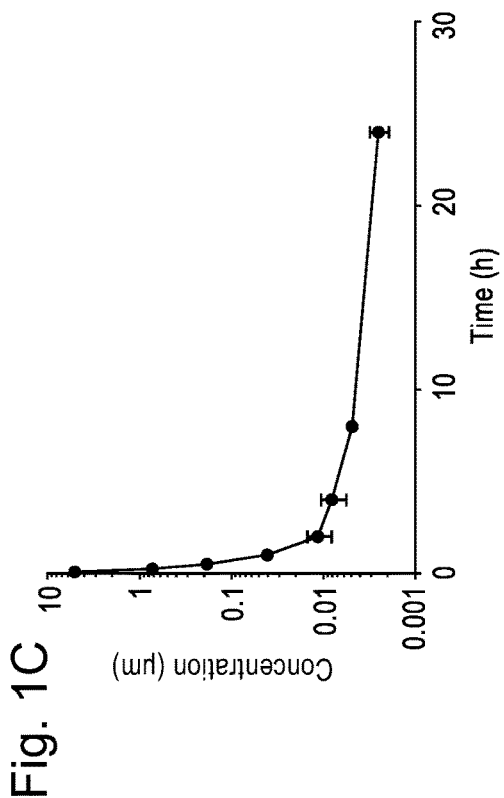

The pharmacokinetics of Compound A was studied following IV bolus administration to mouse, rat and dog as well as following PO administration to mouse and rat. The time-concentration data is shown in FIG. 1 and the parameters derived from non-compartmental analysis are displayed in Table I below.

TABLE I

Pharmacokinetic parameters in preclinical species after IV and PO administration of Compound A

| Parameter | CD-1 Mouse | | SD Rat | | | Beagle Dog |
|---|---|---|---|---|---|---|
| | IV bolus | PO | IV bolus | IV infusion | PO | IV bolus |
| n | 3 | 3 | 3 | 6 | 3 | 3 |
| Dose (mg/kg) | 5 | 20 | 1 | 4.7 (/day) | 10 | 1 |
| Cmax (uM) | 7.99 ± 1.90 | 0.0019 | 2.04 ± 0.23 | 0.13 | 0.0007 | 5.06 ± 0.60 |
| t max (h) | 0.05 | 0.5 | 0.05 | 4 | 0.25 | 0.083 |
| $AUC_{0-t}$ (uM · h) | 1.95 ± 0.28 | 0.0014 | 0.43 ± 0.03 | 12.5 | n.d. | 1.55 ± 0.16 |
| $AUC_{0-inf}$ (uM · h) | 1.96 ± 0.30 | n.d. | 0.44 ± 0.03 | 12.5 | n.d. | 1.60 ± 0.15 |
| t½ (h) | 1.14 ± 0.35 | n.d. | 3.73 ± 1.03 | n.d. | n.d. | 13.6 ± 2.8 |
| MRT (h) | 0.35 ± 0.06 | n.d. | 0.41 ± 0.10 | n.d. | n.d. | 2.17 ± 0.89 |
| CL (mL/min/kg) | 76.7 ± 11.5 | | 67.8 ± 5.3 | | | 18.7 ± 1.7 |
| VDss (L/kg) | 1.58 ± 0.23 | | 1.66 ± 0.42 | | | 2.44 ± 1.11 |
| F(%) | | <1 | | | <1 | |

In mouse, rat and dog the plasma clearance was 77, 68 and 19 mL/min/kg respectively, which equates to an extraction ratio of 86, 97 and 61% respectively (based on total CL being entirely hepatic and using species-specific liver blood flows of 90, 70 and 31 mL/min/kg respectively). Volume of distribution at steady state was measured at 1.58, 1.66 and 2.44 L/kg in mouse, rat and dog respectively. In physiological terms, this corresponds to about 2.2-, 2.4- and 3.5-fold greater than total body water (0.7 L/kg) respectively indicating partitioning into peripheral tissue compartments. The kinetics following IV bolus administration in all three species showed bi-exponential decline, as evidenced by a mean residence time that was shorter than the terminal elimination half-life (Table I). Following PO administration the exposure in terms of Cmax, AUC and oral bioavailability was low. In mouse and rat, following PO administration the exposure in terms of Cmax, AUC and oral bioavailability was low.

Figure 2:
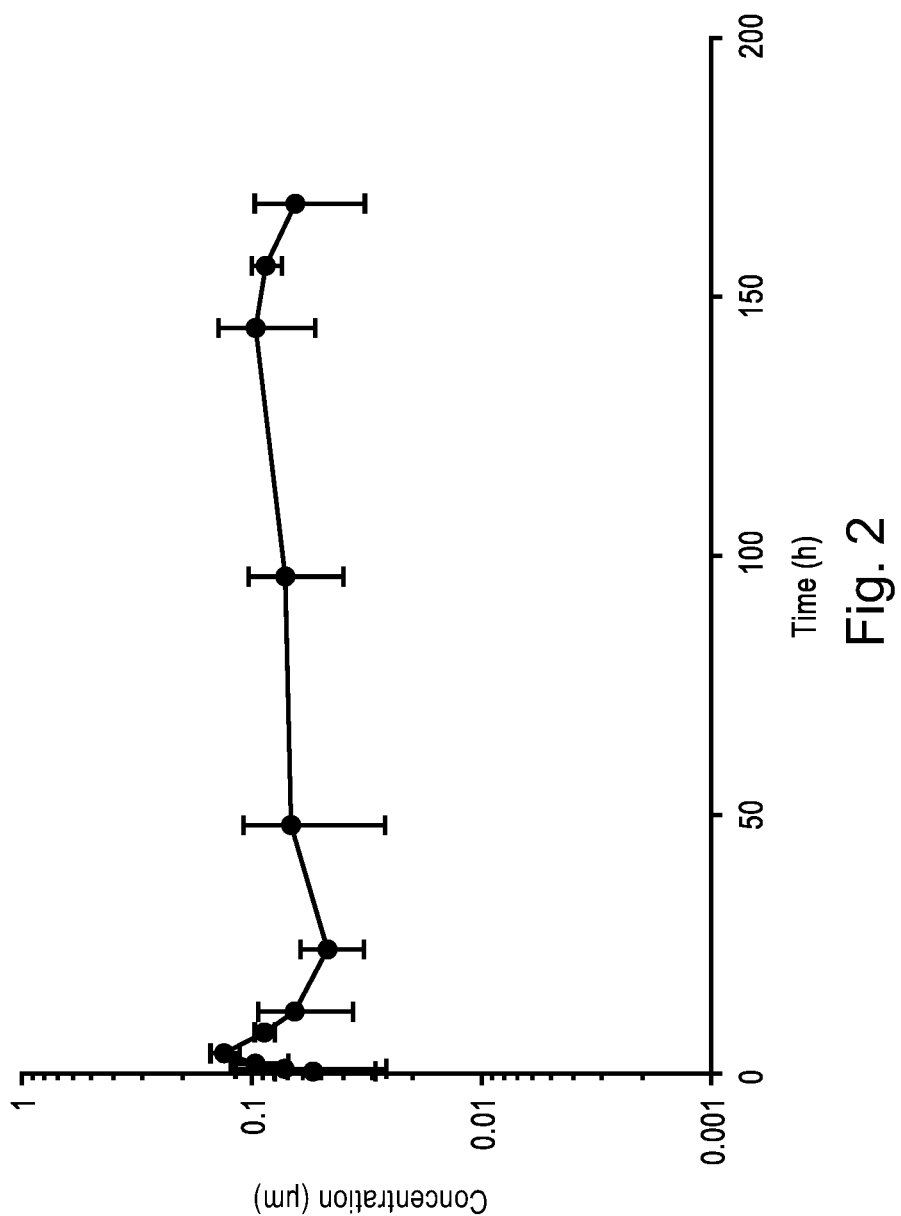
FIG. 2 is a plot of a concentration vs. time profile of plasma concentrations (mean±SD (n=3)) following IV infusion (4.7 mg/kg/day for 7 days formulated in 10% PEG400: 90% saline) administration to SD rats.

Based on the PK/PD relationship, the disease indication and as a consequence of the low oral exposure of Compound A, the compound was explored for the potential delivery by IV infusion. The time-concentration profile following a 7 day IV infusion of Compound A in SD rat is shown in FIG. 2 and the derived parameters are presented in Table I. A dose rate of 4.7 mg/kg/day was able to maintain an average steady state concentration of 78 nM. The time to steady state was achieved within 1 h, in line with the generally accepted 3-5 effective half-lives (Boxenbaum & Battle, Journal of Clinical Pharmacology 35(8): 763-766, 1995). Utilizing the dose rate of 4.7 mg/kg/day and the steady state concentration of 78 nM gives rise to a CL estimate of 74 mL/min/kg, which compares favorably with the CL of 68 mL/min/kg derived from intravenous bolus administration.

In Vitro Metabolic Stability

A summary of the metabolic stability data across species is shown in Table II below.

TABLE II

Liver microsome stability, hepatocyte stability, scaled hepatic CL and blood and plasma binding across species for Compound A

| Species | Mouse | Rat | Dog | Human |
|---|---|---|---|---|
| Liver Microsomal CLint (uL/min/mg) | 150 | 72 | 39 | 88 |
| Scaled Hepatic CL from liver microsomes (mL/min/kg) | 78 | 45 | 20 | 17 |
| Scaled Hepatic CL from liver microsomes w/ fu correction (mL/min/kg) | 43 | 23 | 9 | 8 |
| Hepatocyte CLint (uL/min/million cells) | 3.5 | 1.5 | 14.9 | <1 |
| Scaled Hepatic CL from hepatocytes (mL/min/kg) | 26 | 7 | 21 | <3 |
| Plasma free fraction | 0.138 | 0.272 | 0.234 | 0.125 |
| Blood:plasma ratio | 2.15 | 0.77 | 1.16 | 0.65 |
| Half-life in ex vivo blood plasma (min) | >120 | >120 | >120 | >120 |

Liver microsomal incubations supplemented with NADPH showed moderate turnover in mouse, rat, dog and human which when scaled by the well-stirred liver model gave hepatic CL values of 78, 45, 20 and 17 mL/min/kg indicating moderate to high hepatic extraction in mouse, rat, dog and human respectively. Incorporating plasma protein binding into the microsomal scaling gave hepatic CL values of 43, 23, 9 and 8 mL/min/kg in mouse, rat, dog and human respectively. In liver microsomal preparations supplemented with UDPGA and alamethacin, no turnover was observed indicating glucuronidation is not a primary metabolic pathway for Compound A. In hepatocyte suspensions, turnover of Compound A was very low giving rise to low CL estimates in all species tested, with the exception of dog where an hepatic CL value of 21 mL/min/kg was observed.

Plasma Protein Binding and Blood:Plasma Partitioning

The in vitro binding and partitioning data is shown in Table II. The free fraction in plasma for Compound A did not show any marked species differences with values of 0.138, 0.272, 0.234, and 0.125 in mouse, rat, dog and human respectively. The blood-to-plasma partitioning data across species did not suggest any significant binding of Compound A to erythrocytes with values suggesting a fairly equal distribution between plasma and blood components. Based on this data, plasma clearance, rather than blood clearance, was used in all further data analysis.

Permeability in MDCK Cell Monolayers

The permeability of Compound A in native and MDR1-transfected MDCK cell monolayers is shown in Table III below.

TABLE III

Permeability of Compound A across MDCK cell monolayers

| Cell line | Direction | Mean Papp ($\times 10^{-6}$ cm/s) | Efflux ratio | Relative Efflux ratio |
|---|---|---|---|---|
| MDCK - native | Apical-to-basolateral | 0.09 | 3.3 | <2 |
| | Basolateral-to-apical | 0.30 | | |
| MDCK - MDR1 transfected | Apical-to-basolateral | <0.06 | >3.8 | |
| | Basolateral-to-apical | 0.22 | | |

Compound A shows low apical-to-basolateral permeability in both cell lines with mean Papp values of less than 0.1×10-6 cm/s. The relative efflux ratio between the transfected and native cell lines suggests Compound A is not a substrate for P-gp. However, both cell lines indicate an efflux ratio of approximately 3, suggesting the action of a native transporter protein in the basolateral-to-apical efflux of Compound A.

Interspecies PK Scaling

A summary of interspecies PK predictions for human CL and VDss are shown in Table IV below.

TABLE IV

Predicted Human PK parameters using various interspecies scaling approaches

| Method | Predicted human CL (mL/min/kg) | Predicted human $VD_{SS}$ (L/kg) |
|---|---|---|
| Simple allometry | 13.3 (exponent 0.76) | 2.71 |
| Simple allometry - unbound | 5.7 | 1.16 |
| RoE - MLP | 5.2 | |
| FCIM allometry | 4.3 | |
| MLR rat-dog | 10.7 | |
| Oie-Tozer equation | | 0.97 |
| Wajima equation | | 6.20 |
| Consensus prediction[1] | 6.5 | 2.76 |

[1] consensus prediction excludes simple allometry prediction for CL given the exponent falls outside considered acceptable limits of 0.55 < b < 0.7.

Exemplar allometric plots are illustrated in FIG. 3. Mouse, rat and dog data were utilized unless otherwise stated. Using simple allometry for CL gave rise to an exponent outside the generally accepted criterion of 0.55<b<0.7, and in this case invokes the use of the maximum life potential (MLP)×CL product term, as part of the Rule of Exponents approach (Mahmood & Balian, 1996). Consistent predictions for human CL were obtained with simple allometry of unbound CL, MLP.CL and the fu corrected intercept method, all approximately 5 mL/min/kg. The previously reported multiple linear regression approach using rat and dog data gave a human CL prediction of 11 mL/min/kg. The consensus prediction of all 4 interspecies CL scaling approaches was 6.5 mL/min/kg.

For VDss, simple allometry using total and unbound terms gave rise to similar estimates of 1.2-2.7 L/kg. Using rat and dog data and the Oie-Tozer equation (Oie & Tozer, J Pharm Sci 68(9): 1203-1205, 1979) gave a predicted human VDss of 0.97 L/kg whilst the Wajima MLR approach (Wajima et al., *Journal of Pharmacy and Pharmacology* 55(7): 939-949, 2003) using the same preclinical data gave a predicted human VDss much higher than both allometry and the Oie-Tozer equation, at 6.2 L/kg. The consensus prediction of all 4 interspecies VDss scaling approaches was 2.8 L/kg.

Time-invariant PK scaling

Figure 4:
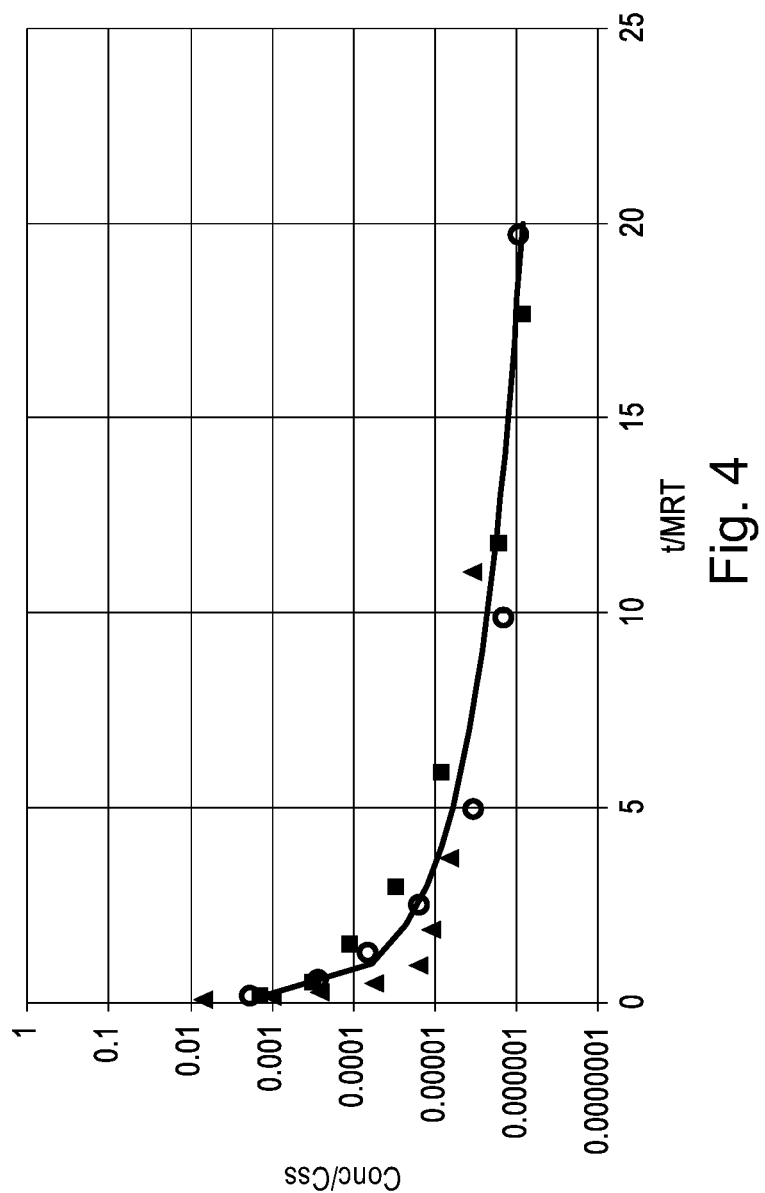
FIG. 4 is a time-invariant PK profile using the Wajima approach of plasma concentration normalized for steady state concentration ("Css") vs. time normalized for mean residence time ("MRT") for each of the preclinical species, mouse (solid squares), rat (open circles) and dog (solid triangles). Solid line is line of best fit of the aggregate data.

The time-concentration profiles from IV bolus administration to mouse, rat and dog were scaled using time-invariant PK scaling approaches; the Dedrick method which normalizes the time-concentration scales by BW^0.25 and dose/BW respectively, and the Wajima method which normalizes the time-concentration scale by MRT and Css respectively. The normalization for physiological time across species has shown utility in predicting the PK profile in human (Dedrick et al., *Cancer Chemotherapy Reports, Part 1* 54(2): 95-101, 1970; Wajima et al., *Journal of Pharmaceutical Sciences* 93(7): 1890-1900, 2004). Using the Wajima approach, the preclinical time-conc profiles overlaid and showed reasonable congruence (FIG. 4) whilst the Dedrick approach did not show alignment across species. Back-calculation of the Wajima normalized time-course with the human predicted MRT and Css provided a time-concentration PK profile for intravenous dosing in man.

Figure 9A:
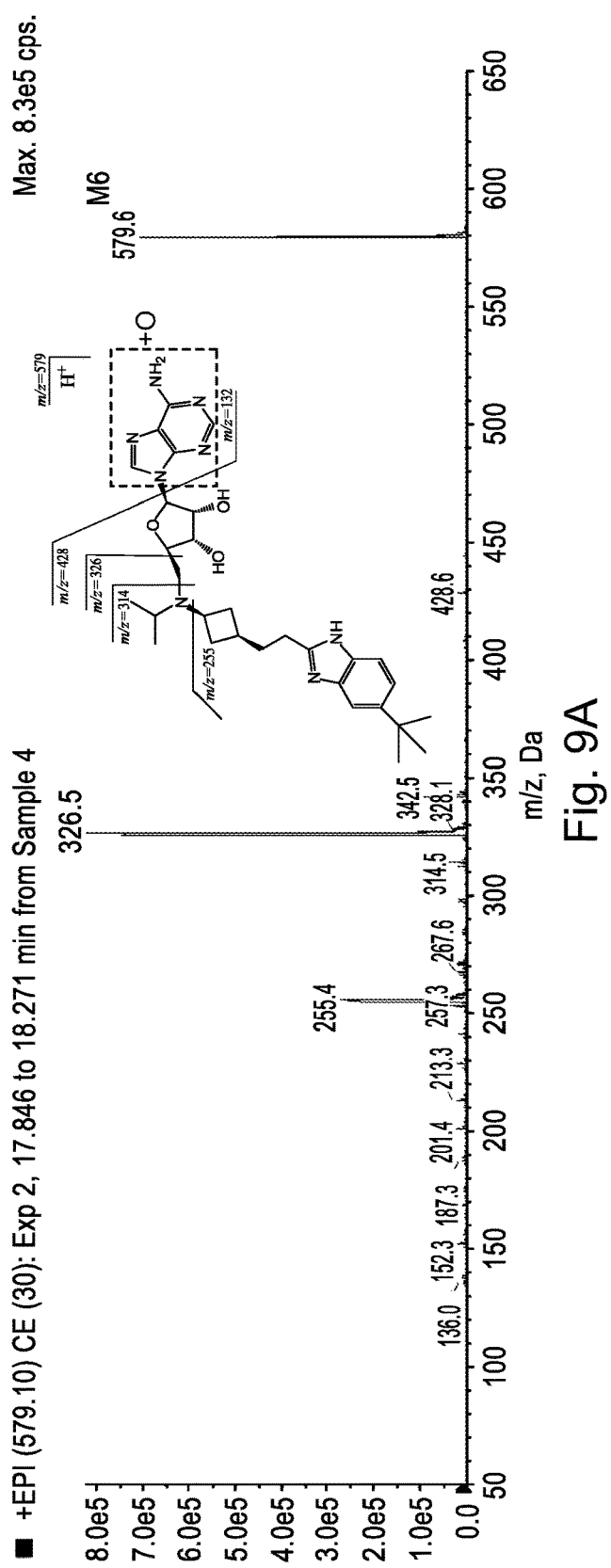
FIGS. 9A and 9B are respectively MS2 spectra of Compound M6 (m/z 579) and Compound A (m/z 563) with proposed fragmentation pathways.
Figure 9B:
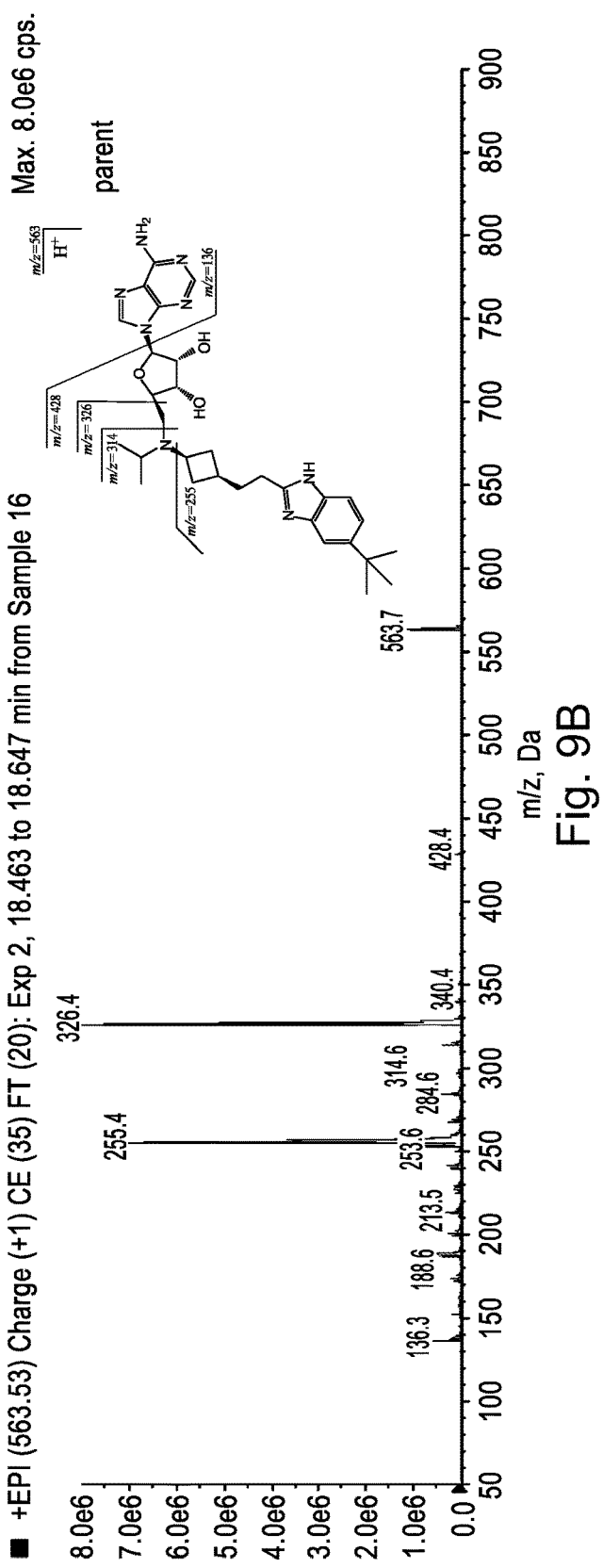
Figure 10:
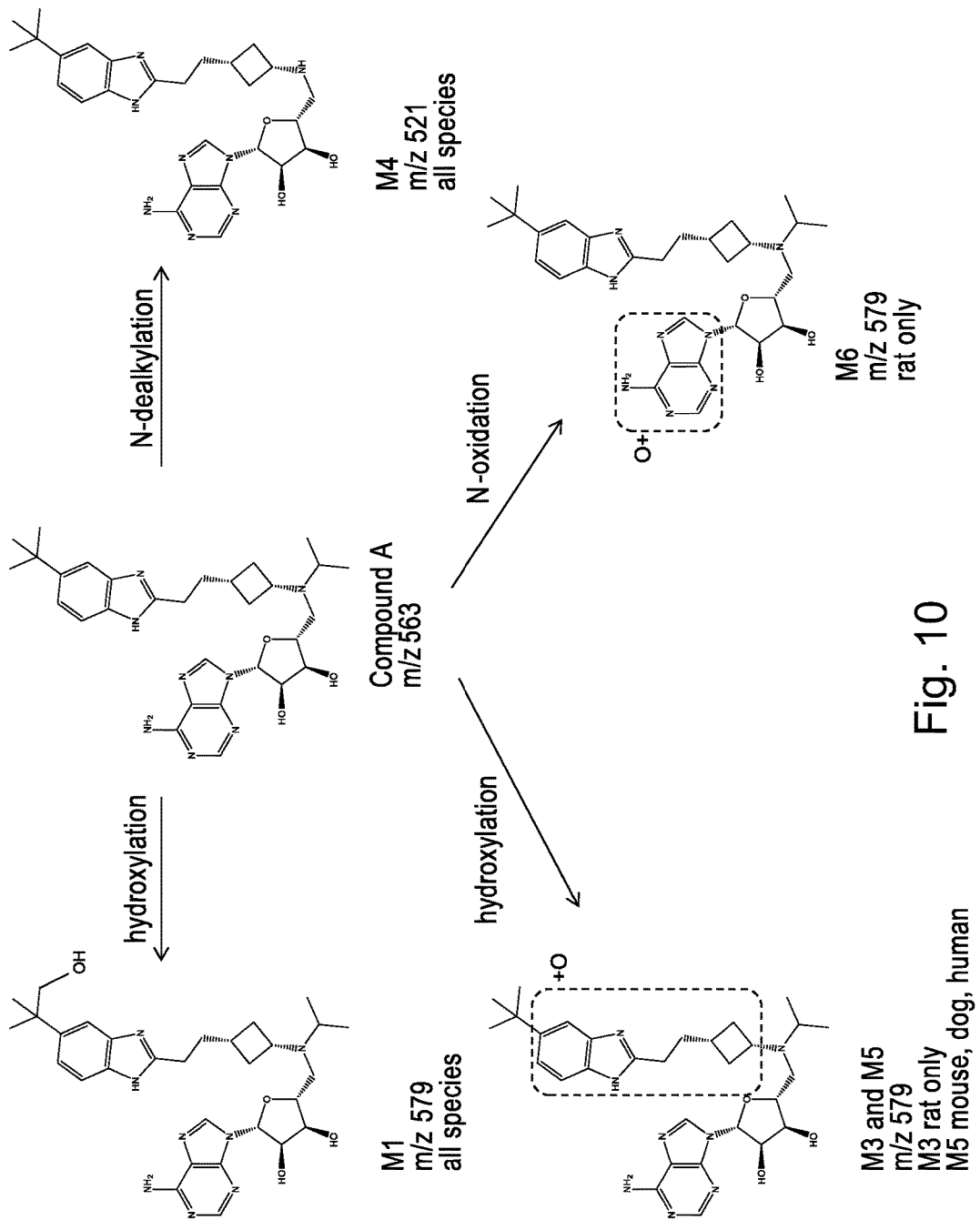
FIG. 10 is a scheme depicting the proposed major metabolic pathways of Compound A in mouse, rat, dog and human liver microsomes supplemented with NADPH and UDPGA.

Structural Elucidation of the Major Metabolites of Compound a by LC-MS and LC-MS/MS The metabolism of Compound A was studied in vitro in liver microsomes supplemented with NADPH and UDPGA, with several metabolites detected in mouse, rat, dog and human. LC-MS and LC-MS/MS were used for identification of Compound A and its metabolites. The molecular ions and characteristic fragment ions are exemplified in FIGS. 6-9. A summary of the metabolites identified is presented in Table V below and the proposed metabolic pathway is shown in FIG. 10. See, also, Basavapathruni et al., *Biopharmaceutics & Drug Disposition*, 35: 237-252 (2014), the content of which is hereby incorporated by reference in its entirety.

TABLE V

Summary of metabolites of Compound A generated in liver microsomes supplemented with NADPH and UDPGA in various species.

| Metabolite | Mass shift (Da) | m/z | Retention time (min) | Abundance based on UV spectra (%)* | | |
|---|---|---|---|---|---|---|
| | | | | Mouse | Rat | Human |
| Parent | 0 | 563.2 | 18.5 | 25.4 | 59.4 | 59 |
| M1 | +16 | 579.3 | 16.3 | 4.5 | 11.3 | 2.6 |
| M3 | +16 | 579.3 | 17.2 | 6.7 | | 3.5 |
| M4 | −42 | 521.3 | 17.4 | | | |
| M5 | +16 | 579.3 | 17.8 | 3.8 | | 10.3 |
| M6 | +16 | 579.3 | 18.0 | | 9.3 | |

*It is not possible to accurately quantify metabolites in dog by UV due to low signal.

Figure 6C:
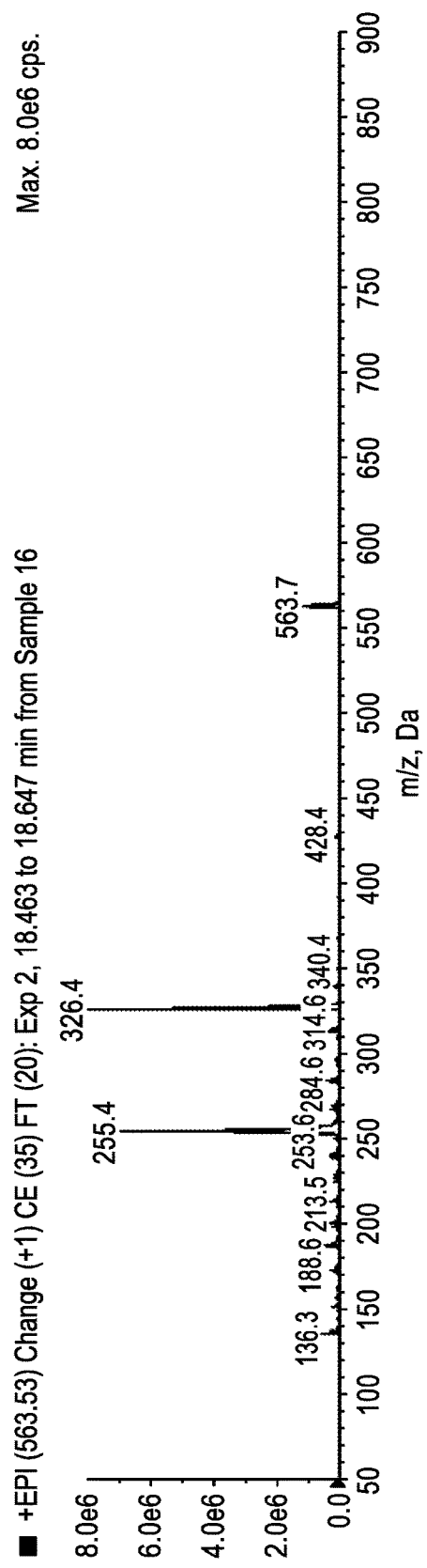
Figure 6D:
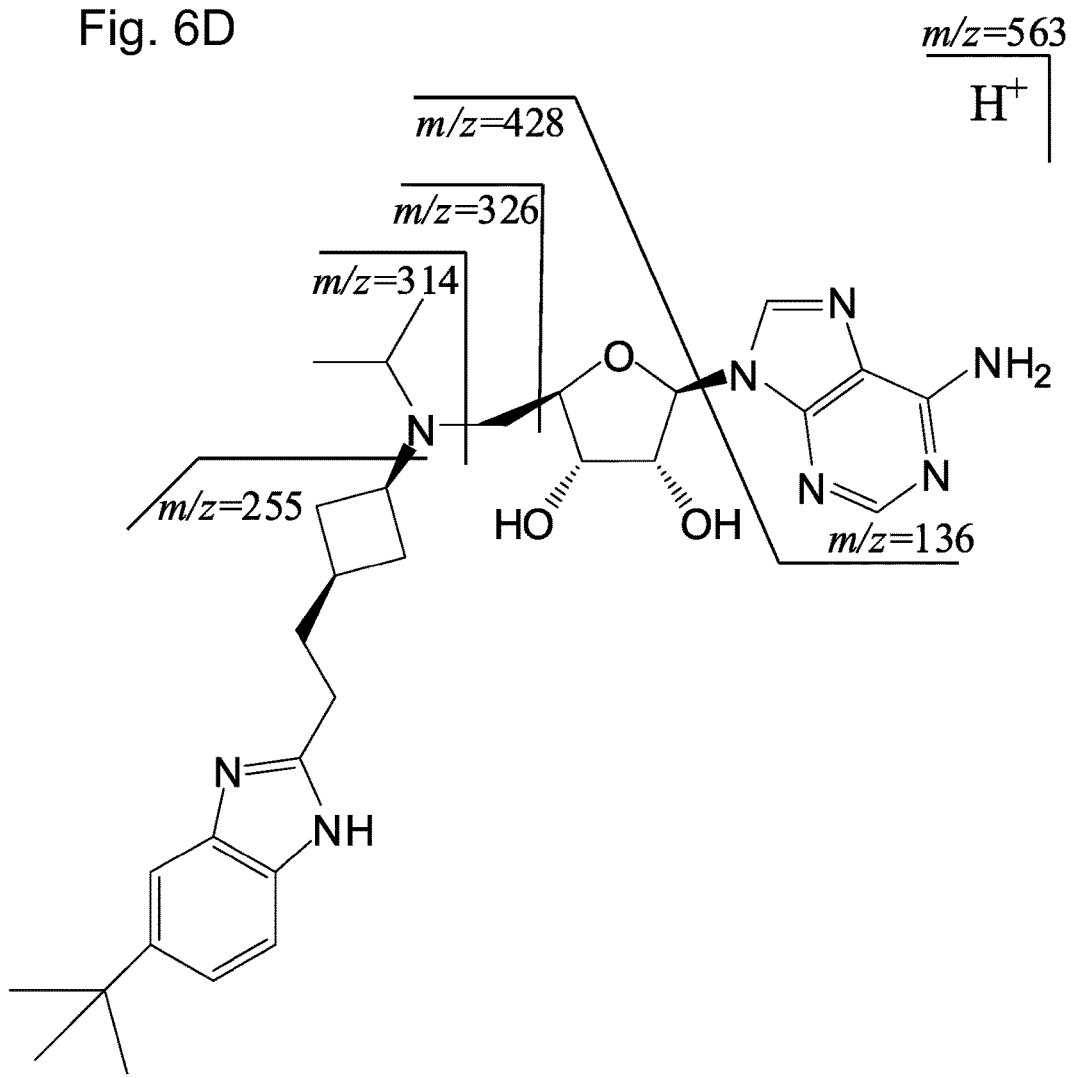

Compound A The protonated molecular ion of Compound A was m/z 563. The proposed fragmentation pathway is shown in FIG. 6D. Loss of the adenine ring gave m/z 428, with m/z 136 corresponding to the protonated adenine ring itself. Loss of the adenosine moiety gave m/z 326, due to the neutral loss of both the tetrahydrofuran and adenine ring systems. Cleavage at the N-cyclobutyl bond gave rise to m/z 255 corresponding to the protonated t-butyl-benzimidazole-cyclobutyl portion of Compound A. Metabolites showed similar fragmentation pathways, which allowed the elucidation and assignment of metabolite structures.

Figure 7A:
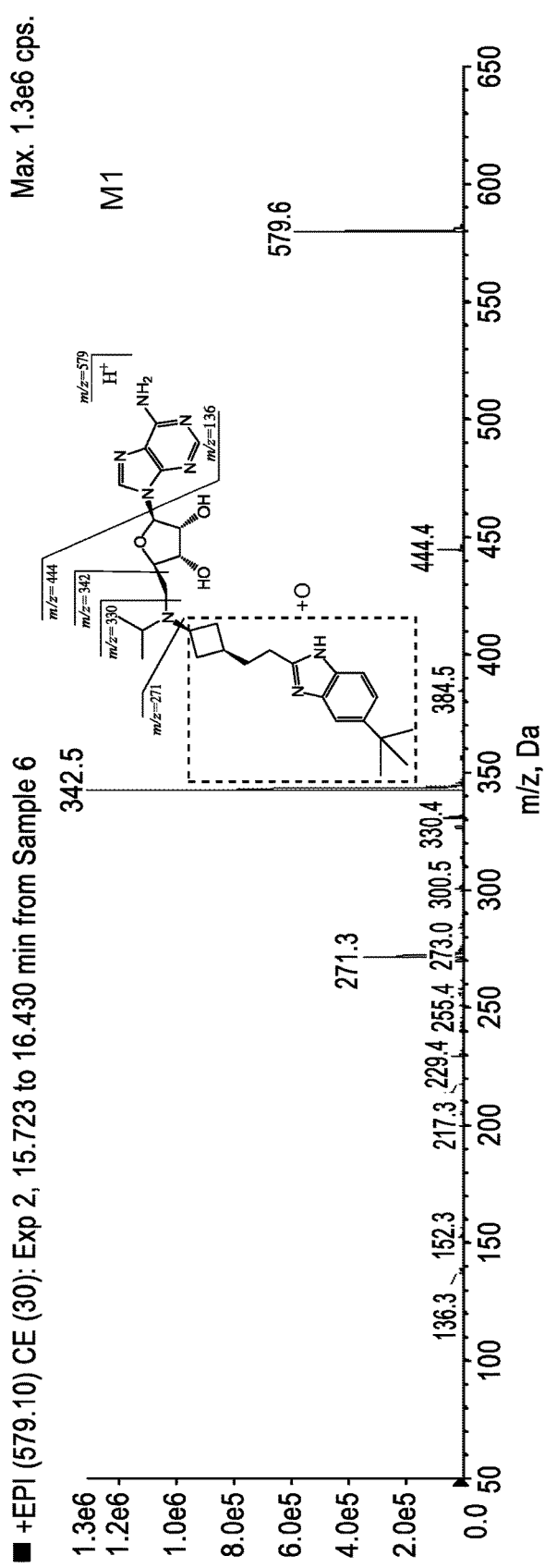
FIGS. 7A and 7B are respectively MS2 spectra of Compound M1, M3, or M5 (m/z 579) and Compound A (m/z 563) with proposed fragmentation pathways.
Figure 7B:
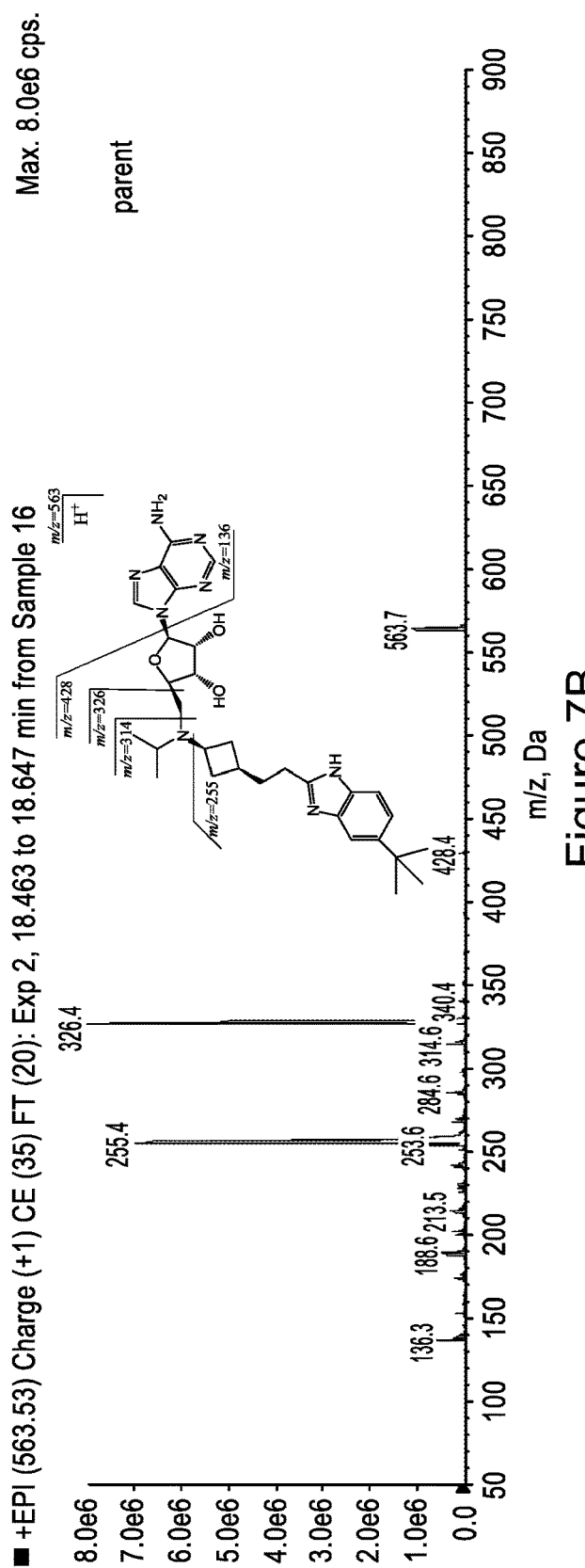

Compound M1 The protonated molecular ion of M1 was m/z 579 indicating a mass shift of +16 Da and a mono-hydroxylation of Compound A. The proposed fragmentation pathway is shown in FIG. 7A. Comparison of the MS2 data of M1 with that from the parent compound suggested the mono-hydroxylation occurred on the t-butyl-benzimidazole-cyclobutyl portion of the molecule, which was further verified by NMR data. This was supported by the fragment ions from M1 with m/z 444, 342, 330 and 271 all retaining a +16 Da mass shift with corresponding ions from Compound A (m/z 428, 326, 314 and 255). The fragment ion m/z 136, corresponding to the adenine ring, was present in MS2 spectra for both parent and M1.

Compound M3 The protonated molecular ion of M3 was m/z 579 indicating a mass shift of +16 Da and a mono-hydroxylation of Compound A. The proposed fragmentation pathway is shown in FIG. 7A. The MS2 data for M3 gave fragment ions of m/z 444, 342 and 271, and as such could not be differentiated structurally from M5.

Figure 8A:
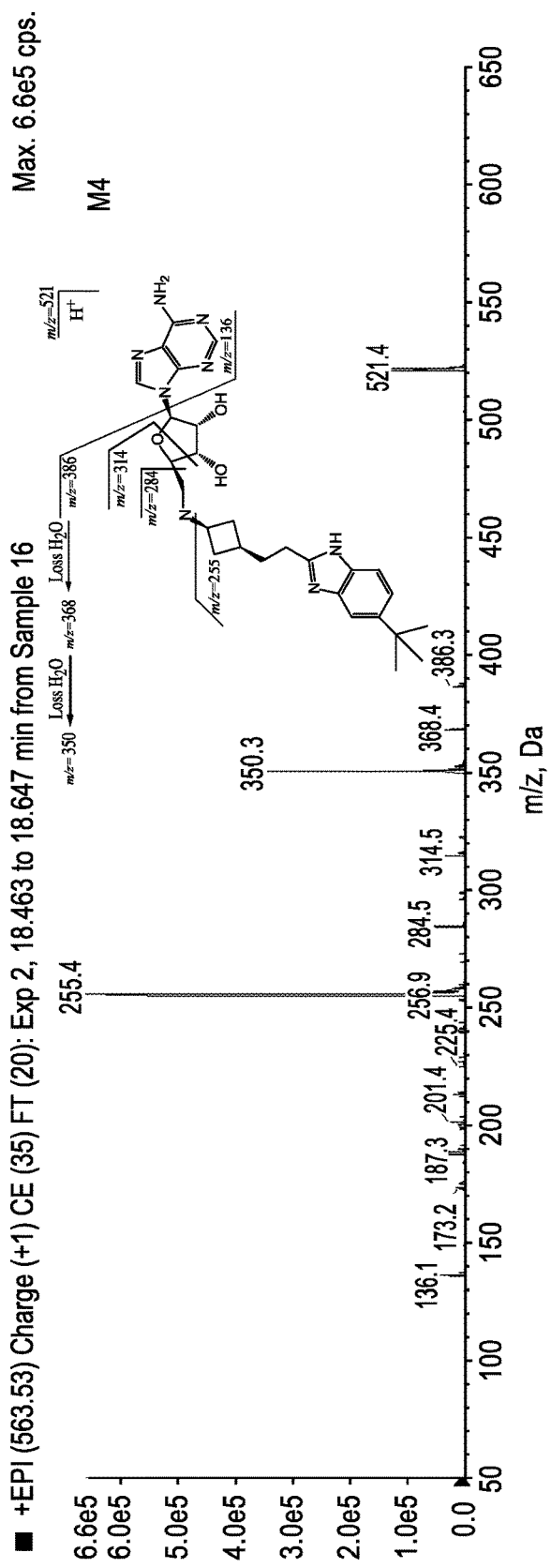
FIGS. 8A and 8B are respectively MS2 spectra of Compound M4 (m/z 521) and Compound A (m/z 563) with proposed fragmentation pathways.
Figure 8B:
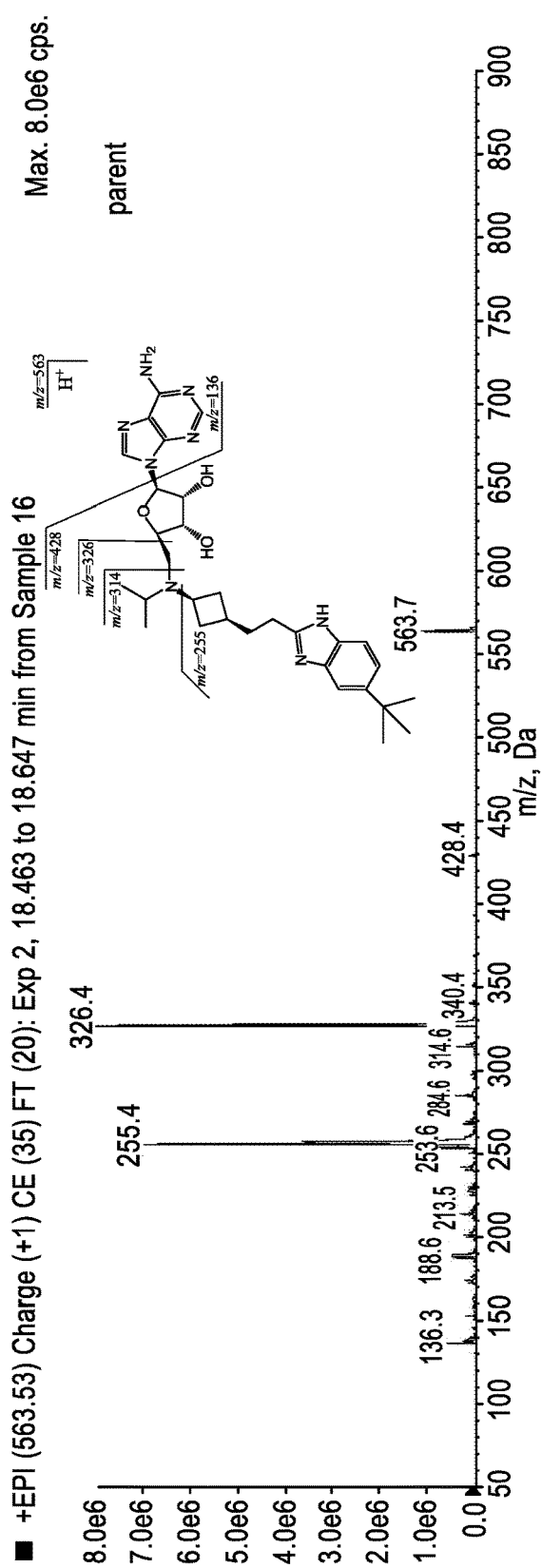

Compound M4 The protonated molecular ion of M4 was m/z 521 indicating a mass shift of −42 Da and dealkylation of the N-isopropyl group of Compound A. The proposed fragmentation pathway is shown in FIG. 8A. Comparing the MS2 data with that of parent revealed fragment ions m/z 255 and 136 were identical in both species, while product ions m/z 386, 368, 350 and 284 supported N-dealkylation of the isopropyl group.

Compound M5 The protonated molecular ion of M5 was m/z 579 indicating a mass shift of +16 Da and a mono-hydroxylation of Compound A. The proposed fragmentation pathway is shown in FIG. 7A. The MS2 data for M5 gave fragment ions of m/z 444, 342 and 271, and as such could not be differentiated structurally from M3.

Compound M6 The protonated molecular ion of M6 was m/z 579 indicating a mass shift of +16 Da and tentatively assigned as an N-oxidation product of Compound A. The proposed fragmentation pathway is shown in FIG. 9A. The MS2 product ions of m/z 428, 326 and 255 were characteristic of the benzimidazole, cyclobutyl and ribose moieties of the parent molecule suggesting oxidation of the adenine ring, most likely the N-oxide.

The in vivo PK profiles in mouse, rat and dog following IV bolus administration showed biexponential kinetics that was more apparent as the order of the species increased. This resulted in elimination half-lives increasing from 1.1 h in mouse, 3.7 h in rat and 13.6 h in dog. In addition, MRT was shorter than the elimination t1/2 further supporting multi-exponential kinetics in the preclinical species. The CL in all species was moderate to high with estimated hepatic extraction ratios of 86, 97 and 61% in mouse, rat and dog respectively. Expressing CL in its unbound or blood form did not contribute to any appreciable species differences since there was reasonable agreement across species in plasma free fraction and with blood partitioning values around unity. Volume of distribution at steady state (VDss) was consistent across species with values 2-3 fold greater than total body water indicating partitioning into peripheral tissues. Unbound VDss was also fairly consistent across species at 11.4, 6.1 and 10.4 L/kg in mouse, rat and dog respectively. The intrinsic clearance data in liver microsomes and hepatocytes indicated oxidative metabolism was an important metabolic pathway. The scaled clearance from liver microsomes showed excellent agreement with in vivo clearances in the preclinical species, further supporting perfusion-limited CL and oxidative metabolism as the primary elimination pathway. Interestingly, with the exception of dog, the scaled hepatocyte data gave rise to much lower values between 3- and 10-fold lower than observed CL, suggesting permeation or hepatocyte uptake was rate limiting. This has been demonstrated for other compounds showing a similar disparity between liver microsome and hepatocyte clearance (Di et al., *European Journal of Medicinal Chemistry* 57: 441-448, 2012). Dog is an apparent outlier in this cross species comparison, showing good concordance in clearance prediction by both liver microsomes and hepatocytes. This may be indicative of an hepatic uptake process specific to the dog, not present in other species where low passive permeation limited the turnover in hepatocyte incubations. This is supported by the slightly higher VDss observed in dog which would correspond to greater tissue permeation and uptake. Overall, these observations are in line with physicochemical properties such as PSA (144 $Å^2$) and the MDCK permeability which was less than $1×10^{-6}$ cm/s. Further in vitro metabolism studies confirmed no evidence of glucuronidation in all species tested and no instability in blood plasma. Although there was no indication of Compound A acting as a P-gp substrate, there was evidence of a transporter native to the MDCK cell line involved in a basolateral-to-apical efflux process. This is an as yet unidentified transporter and it is noteworthy that it is native to this cell line of dog kidney origin.

Compound A showed negligible oral bioavailability in mouse and rat, which is in line with the physicochemical properties, in terms of parameters generally regarded as necessary for favorable gastrointestinal absorption (van de Waterbeemd, *Methods and Principles in Medicinal Chemistry* 40 (Drug Bioavailability): 71-99, 2009). Compound A has a calculated log P of 3.26, a PSA of 144 $Å^2$ and a molecular weight of 563. The oral absorption is permeability-limited based on poor passive permeation observed in MDCK cell monolayers. The oral exposure may also be perturbed by moderate-to-high first pass extraction in rodents. An IV infusion dosing paradigm was pursued. Pharmacokinetic data in rat demonstrated that steady-state concentrations (Css) could be achieved rapidly, and sufficiently maintained over the dosing interval. Clearance estimates based on the IV infusion data (using dose rate divided by Css) were in excellent agreement with those from IV bolus administration; 74 and 68 mL/min/kg respectively.

The predictive accuracy of interspecies PK scaling has received much attention recently with several large initiatives to identify the most predictive methods in estimating human PK endpoints from preclinical species (Jones et al., 2011; Lombardo et al., 2013a; Lombardo et al., 2013b; Poulin et al., *Journal of Pharmaceutical Sciences* 100(10): 4050-4073, 2011a; Poulin et al., *Journal of Pharmaceutical Sciences* 100(10): 4127-4157, 2011b; Ring et al., 2011; Vuppugalla et al., 2011). As shown in Table IV, the data were analyzed in several ways using a multitude of approaches recommended in these recent analyses, giving careful consideration to cases of congruence or disparity in prediction. Three orthogonal methods were utilized including IVIVE, interspecies scaling and time-invariant scaling. Simple allometry utilizing total and unbound VDss gave rise to similar predictions as did the use of the Oie-Tozer equation, all indicating a human VDss in the 1-3 L/kg range. The recent PhRMA analysis and others have shown the superior predictive accuracy afforded by the Oie-Tozer approach (Oie & Tozer, 1979). For Compound A, allometric and physiologically-based methods gave similar predictions for VDss. The Wajima equation which utilizes a multiple linear regression of rat and dog VDss gave a much higher estimate of human VDss (Wajima et al., 2003). This may be a result of the MLR equation being weighted towards dog VDss, which for Compound A was the highest VDss observed in preclinical species. Simple allometry of CL gave rise to an exponent outside the acceptable range of 0.55<b<0.7, and as a result the rule of exponents was adopted and the product term of CL and maximum life potential was utilized (Mahmood & Balian, 1996). The interspecies scaling of CL was attained by the approaches of simple allometry using unbound CL, Rule of Exponents using MLP, fu-corrected intercept method allometry and a multiple linear regression method using rat and dog CL, all giving rise to a consensus prediction of 6.5 mL/min/kg for human CL and with a reasonably low CV (44%) across the different methods. Recent global analyses of human CL prediction by different groups have highlighted the predictive accuracy of the fu-corrected intercept method (Lombardo et al., 2013a; Ring et al., 2011). The allometric methods show very good agreement and are expected to perform well in cases such as this, where compounds exhibit moderate CL across species.

Liver microsomes supplemented with NADPH provided good agreement with in vivo CL across all three preclinical species. Even in the case of incorporating plasma protein binding into the well stirred model, the CL estimates remained within 2-3 fold of the measured CL. Challenges and limitations in IVIVE include whether to incorporate plasma free fraction when the level of protein binding is low to moderate and may introduce a fold change in CL coincident with the current practical limit in predictive accuracy for IVIVE of 2-3 fold. That said, liver microsomal CL with fu correction does provide a human CL estimate in good agreement with the interspecies scaling methods. In addition, an observation made by the recent PhRMA initiative eluded to the greater predictive accuracy of in vivo scaling methods compared to current IVIVE approaches. This may relate to specific dynamic and complex equilibria present in vivo that are not captured in the simplified in vitro setting. In addition, it is a common observation that liver microsomes have a tendency to overpredict CL especially for compounds with low passive membrane permeability. This was largely exemplified with the scaled hepatocyte CL values for Compound A in which low turnover was observed for mouse, rat and human (CLint<4 uL/min/million cells). Dog was a clear outlier in terms of scaled hepatocyte clearance and this may relate to a hepatic uptake process well represented in dog. Overall, across multiple, diverse scaling approaches Compound A human CL estimates are in the range of 6-8 mL/min/kg. The time-invariant PK methodology originally reported by Wajima showed a compelling overlay of the preclinical data when normalized for time (t/MRT) and concentration (C/Css) and provided a useful transformation of the primary human PK parameters into a time-concentration plot with which to model various clinical dosing paradigms.

Due to the much lower turnover observed in hepatocytes, liver microsomes were selected for metabolite identification and profiling. As noted earlier, no turnover was observed in blood plasma or liver microsomes supplemented with alamethacin and UDPGA, indicating that hydrolysis or glucuronidation were not primarily involved in the metabolism of Compound A. In liver microsomes supplemented with NADPH and UDPGA, several oxidative metabolites were observed. Metabolites M1, M3 and M5 were all distinct mono-hydroxylations on the benzimidazoles-ethylene-cyclobutyl portion of the molecule. The hydroxylation position of M1 (as shown in FIG. 10) was verified by NMR experiment. The exact positions of hydroxylations in M3 and M5 are yet to be determined. M3 was only observed in rat whilst M1 and M5 were present in all preclinical species as well as human. Metabolite M4, N-dealkylation and loss of the isopropyl group, was observed in all species tested whilst M6, the N-oxidation of the adenine ring, was only observed in rat. No glucuronides of Compound A or its hydroxylated metabolites were detected and no metabolites unique to human were present in this in vitro metabolism study.

The biological activities of the compounds of the invention can be evaluated using the methods described in Examples 3-8 below.

EXAMPLE 3

General Methods

Cell Culture:

Human leukemia cell line EOL-1 (Catalog # ACC-386) is purchased from DSMZ and are grown in Roswell Park Memorial Institute medium (RPMI) with 10% Fetal Bovine Serum (FBS). Cells are kept in log growth as outlined in the technical data sheet provided by the vendor.

Human hematological tumor cell lines THP-1, RS4; 11, and MV4-11 are obtained from ATCC, MOLM-13 cells are obtained from DSMZ. All lines are grown in RPMI 1640 containing 10% FBS and maintained using the vendors recommended cell densities and environmental conditions. Media is supplemented with non-essential amino acids and L-Glutamine. THP-1 cells are also supplemented with 0.05 mM 13-Mercaptoethanol.

Methylation Analysis. Cells are seeded at $5\times10^5$ cells/mL in a 12 well plate at a final volume of 2 mLs. Cells are dosed with compounds to the appropriate concentration from a 50 mM DMSO stock solution. Compound and media are refreshed every two days over the course of seven day incubation by counting cells using trypan blue exclusion (Vicell), pelleting at 200 g for 5 minutes and resuspending in fresh media containing compound at a final cell concentration of $5\times10^5$ cells/mL. Following compound incubation, histones are extracted from $1\times10^6$ cells using a commercial histone extraction kit (Active Motif). Purified histones are quantitated using the BCA protein assay (Pierce) with a BSA standard curve. 400 ng of isolated histones are fractionated by SDS-PAGE on a 4-20% gel and transferred to nitrocellulose membranes. Membranes are incubated with various primary and secondary antibodies and imaged on the Licor imaging system (Odyssey). The H3K79-Me2 rabbit polyclonal is purchased from Abcam. Other rabbit polyclonal antibodies including H3K4-Me3, H3K9-Me3, H3K27-Me2, and H3K27-Me3 are purchased from Cell Signaling Technologies (CST). A mouse monoclonal total H3 antibody is used as a loading control (CST). Fluorescently labeled secondary antibodies are purchased from Odyssey.

Cell Growth and Viability Assay

Exponentially growing cells (e.g., EOL-1, THP-1, MV4-11 and MOLM-13 cells) are plated in 96-well plates at a density of $3\times10^4$ viable cells/well. Each treatment is seeded in triplicate with a final well volume of 150 µLs. Cells are incubated with increasing concentrations of DOT1L inhibitor up to 50 µM. Viable cell number is determined every 3-4 days for 11 days using the Guava Viacount assay (Millipore #4000-0040) and analyzed on a Guava EasyCyte Plus instrument according to the manufacturer's protocol. On the days of cell counts, growth media and inhibitor are replenished and cells maintained in log phase culture by reseeding at a density of $5\times10^4$ viable cells/well. Total cell number is expressed as split-adjusted viable cells per well. For each cell inhibitor $IC_{50}$ values are determined from concentration-dependence curves at day 11. All calculations are done using GraphPad Prism, version 5.00 for Windows, GraphPad Software, San Diego Calif. USA (www.graphpad.com).

Histone Extraction of Cell Pellets:

Frozen pellets are allowed to thaw briefly on ice and then lysed by a 5 minute incubation on ice with 250 µl nuclear extraction buffer (10 mM Tris-HCl, pH 7.6, 10 mM $MgCl_2$, 25 mM KCl, 1% Triton X-100, 8.6% Sucrose, plus a Roche protease inhibitor tablet 1836153001). Nuclei are collected by centrifugation at 600 g for 5 minutes at 4° C. and washed once in Tris/EDTA buffer (pH 7.4). Supernatant is removed and histones extracted for one hour with 60 µl 0.4 N cold sulfuric acid. Extracts are clarified by centrifugation at 10,000 g for 10 minutes at 4° C. and transferred to a fresh microcentrifuge tube containing 600 µl ice cold acetone. Histones are precipitated at −20° C. for 2 hours, pelleted by centrifugation at 10,000 g for 10 minutes and resuspended in 60 µl distilled water (DI water). Total protein of the acid extracts is assessed using a bicinchoninic acid (BCA) protein quantification assay with a bovine serum albumin (BSA) standard (Pierce Biotechnology).

H3K79me2 Immunoblot:

For immunoblot analysis of the H3K79me2 inhibition by DOT1L inhibitor, exponentially growing cells (e.g., EOL-1 cells) are seeded at $2\times10^5$ cells/mL and incubated in the presence of increasing concentrations of DOT1L inhibitor for 4 days. Following incubation, cells ($2-3\times10^6$) are harvested and histones extracted as described. Histones (400 ng) are fractionated on a 10-20% Tris HCl gels (Bio-Rad) with Tris-Glycine SDS running buffer (Invitrogen) under denaturing conditions and transferred to a nitrocellulose filter. The filter is incubated for 1 hour in blocking buffer (Odyssey blocking buffer, Li-cor, 927-40000) at RT and then incubated overnight at 4° C. in blocking buffer containing an antibody specific for H3K79me2 (1:5000 dilution, abcam ab3594). Filters are washed 3 times for 5 minutes with wash buffer (PBST) and incubated with infrared tagged secondary antibody (Alexa Flour 680 goat anti-rabbit IgG (1:20,000), Invitrogen A-21076) at RT for 1 hour. Filters are washed in PBST and reprobed for 1 hour at RT with the appropriate total histone antibody control (mouse anti-histone H3 (1:20,000), CST 3638, or mouse anti-histone H4 (1:10,000), CST 2935). Filters are washed again in PBST and incubated with infrared tagged secondary antibody (IRDye 800Cw donkey-anti-mouse IgG (1:20,000), Li-Cor 926-32212) at RT for 1 hour. After a final wash in PBST, filters are scanned using the Odyssey infrared imager (Li-cor). Signal intensities specific for each methyl-specific antibody is quantified using Odyssey software and normalized to that of the appropriate total histone control signal on the same filter by dividing the methyl-specific antibody signal intensity by the total histone control signal intensity.

Quantitative Real-Time PCR:

Exponentially growing cells (e.g., EOL-1 cells) are plated in a 12 well plate at $2\times10^5$ cells/mL. Cells are incubated in the presence of increasing concentrations of a test compound up to 10 µM. On day 4, cells are maintained in log phase culture by reseeding at $5\times10^5$ cells/mL and compound is replenished. At day 6 cells are washed twice with PBS and pelleted by centrifugation at 200×g. Cell pellets are lysed in 300 µL RLT buffer (Qiagen) and total RNA is isolated using the RNeasy total RNA isolation kit (Qiagen 74106). Total RNA (1 µg) was reverse transcribed using a high capacity cDNA reverse transcription kit (Applied Biosystems 4368813). RNA isolation and cDNA synthesis are carried out according to the manufacturer's protocol. Predesigned labeled primer and probe sets for HOXA9 (Hs00365956), MEIS1 (Hs00180020) and FLT3 (Hs00975659) are purchased from Applied Biosystems. Quantitative real-time PCR (qPCR) reactions contained 50 ng cDNA, 1× labeled primer and probe set, and 1× Taqman universal PCR master mix (Applied Biosystems 4304437). Samples are run on a 7900 HT Fast Real Time PCR machine (Applied Biosystems 4351405) with cycling conditions of 2 min 50° C., 10 min 95° C., 40 cycles at 15 sec 95° C. and 1 min 60° C. Target gene cycle numbers are normalized to the house keeping gene β2-microglobulin (Applied Biosystems 4333766) to get a ΔCT value. Percent of DMSO control is calculated with the equation $(2^{-\Delta\Delta CT})*100$ where the ΔΔCT is the difference between normalized target gene and DMSO control (ΔCT sample−ΔCT control=ΔΔCT).

Determination of $IC_{50}$ Test compounds are serially diluted 3 fold in DMSO for 10 points and 1 μl is plated in a 384 well microtiter plate. Positive control (100% inhibition standard) is 2.5 uM final concentration of S-adenosyl-L-homocysteine and negative control (0% inhibition standard) contained 1 μl of DMSO. Compound is then incubated for 30 minutes with 40 μl per well of DOT1L(1-416) (0.25 nM final concentration in assay buffer: 20 mM TRIS, pH 8.0, 10 mM NaCl, 0.002% Tween20, 0.005% Bovine Skin Gelatin, 100 mM KCl, and 0.5 mM DTT). 10 μl per well of substrate mix (same assay buffer with 200 nM S-[methyl-$^3$H]-adenosyl-L methionine, 600 nM of unlabeled S-[methyl-$^3$H]-adenosyl-L methionine, and 20 nM oligonucleosome) is added to initiate the reaction. Reaction is incubated for 120 minutes at room temperature and quenched with 10 μl per well of 100 μM S-methyl-adenosyl-L methionine. For detection, substrate from 50 μl of reaction is immobilized on a 384 well Streptavidin coated Flashplate (Perkin Elmer) (also coated with 0.2% polyethyleneimine) and read on a Top Count scintillation counter (Perkin Elmer).

Other related general procedures and specific preparation procedures can also be found in the PCT publication Nos. WO2012/075381 and WO 2014/026198, the contents of each are incorporated herein by reference in their entireties.

EXAMPLE 4

Effect of DOT1L Inhibition on Cell Growth and Viability

The effect of DOT1L inhibitors on leukemia cell growth and viability is investigated. EOL-1 cells, a leukemia cell line characterized by MLL PTD, are plated in 96-well plates at a density of 3×10$^4$ viable cells/well. Cells are incubated with increasing concentrations of DOT1L inhibitor between the 0.003 μM-50 μM. The number of viable cells is determined every 3-4 days for 11 days. Cells are maintained in log phase by reseeding and replenishing growth media and the indicated concentration of DOT1L inhibitor on each day of cell counts (Day 0, Day 4, Day 7, and Day 11). Total cell number is expressed as split-adjusted viable cells per well. DMSO-treated cells are used as a control.

Cell proliferation is inhibited in a dosage-dependent manner, with the highest concentration (50 μM) having the most pronounced inhibitory effect on cell proliferation and viability.

EXAMPLE 5

Inhibition of DOT1L Methyltransferase Activity

Inhibition of methylation of H3K79 is assessed after 4 days of treatment of DOT1L compounds in exponentially growing cells (e.g., EOL-1 cells).

H3K79 methylation status after treatment with a test compound is first examined by immunoblot. Following treatment, cells are harvested and histones are extracted. Western blot analysis is performed using antibodies specific for H3K79me2 and total histone 3 (as a control). Signal intensities specific to H3K79me2 is quantified and normalized to that of the total histone 3 signal.

EXAMPLE 6

Potency of DOT1Inhibition

The IC50 and inhibition constants of the DOT1L inhibitors described herein can be determined from concentration-dependence growth curves, as described in Example 2. The concentration-dependence curves at day 11 for a test compound and a control compound are plotted on a single log graph and compared. IC50 values, or maximal inhibitory concentration, for each DOT1L inhibitor can be determined from the curves.

The inhibition constant (Ki) can also be determined for the DOT1L inhibitors described herein. For example, Ki values for a test compound and a control compound can be compared. The test compound having the lowest Ki, which indicates that a very low concentration (e.g., 0.08 nM) of the test compound is required to decrease the maximal rate of the reaction to half of the uninhibited value, in the presence of a low substrate concentration. As expected, the control compound has a very high Ki (e.g., more than 50,000 nM), showing that the control compound requires a very little inhibitory activity.

EXAMPLE 7

Gene Overexpression in Leukemias

HOXA9 expression levels are assessed in a panel of leukemia cells lines, demonstrating that HOXA9 is often overexpressed in various hematologic cancers. The leukemia cells assessed include MolM13 (acute monocytic leukemia cell line), MV411 (acute myelocytic leukemia), LOUCY (T-cell acute lymphoblastic leukemia), EOL-1 (eosinophilic leukemia) SemK2 (B-cell acute lymphoblastic leukemia), Reh (acute lymphoblastic leukemia), HL60 (promyelocytic leukemia) and BV173 (pre-B-cell leukemia). Molm13, MV411, and SemK2 cell lines are characterized as having MLL fusions. LOUCY and Reh cell lines are characterized as having non-MLL chromosomal rearrangements. EOL-1 cells are characterized as having MLL-PTD.

Cells are harvested, RNA is extracted, and cDNA is prepared as described in Example 1. The expression level of HOXA9 is determined by quantitative real-time PCR. HOXA9 expression level is normalized to the lowest HOXA9 expresser. Jurkat cells, an immortalized T-lymphocyte cell line, are used as control. HL60, BV173, and Reh cell lines had very low overexpression of HOXA9. SemK2, EOL-1, LOUCY, MV411, and Molm13 had extremely high overexpression of HOXA9, with at least a 2000-fold increase over the lowest expresser. Overexpression of other cancer-associated genes, such as FLT3, MEIS1, or DOT1L can be determined using similar methods as those described herein.

EXAMPLE 8

Gene Expression after DOT1L Inhibition

Leukemia cell lines can be treated with DOT1L inhibitors and the expression of select genes can be examined to assess the effects of DOT1L inhibition on cancer-associated gene overexpression. Leukemia cell lines are treated with increasing concentrations of candidate DOT1L inhibitors up to 10 μM for 6 days. For the vehicle control, cells are treated with DMSO. Cells are then harvested, RNA is extracted, and cDNA is prepared as described in Example 1.

Expression levels of select genes, including HOXA9, FLT3, MEIS1, and DOT1L, are determined by quantitative real-time PCR. Expression of HOXA9, FLT3 and/or MEIS1 can be reduced in a dose-dependent manner after treatment with a test compound. DOT1L gene expression is not reduced after treatment with DOT1L inhibitor and can be considered useful for control purposes.

The entire disclosure of each of the patent documents and scientific articles referred to herein is incorporated by reference for all purposes.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound of Formula (II):

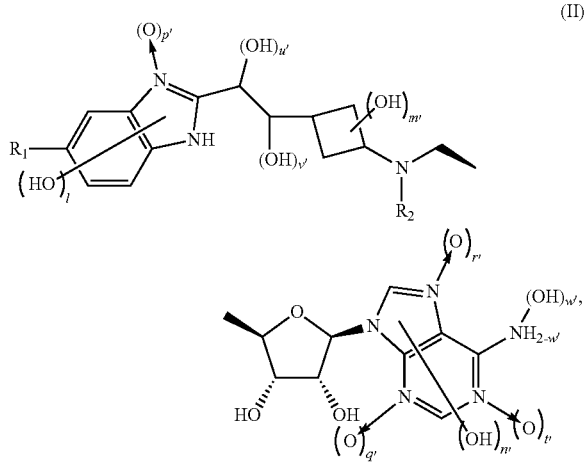

(II)

or a pharmaceutically acceptable salt or ester thereof, wherein $R_1$ is t-butyl substituted with one or more substituents selected from hydroxyl and oxo;

$R_2$ is H, hydroxyl, unsubstituted i-propyl, or i-propyl substituted with one or more hydroxyl;

l' is 0, 1, 2, or 3;

each of m' and n', independently, is 0, 1, or 2;

each of p', q', r', t', u', v', and w', independently, is 0 or 1; and when $R_1$ is t-butyl substituted with only one hydroxyl, $R_2$ is H, hydroxyl, or i-propyl substituted with one or more hydroxyl; and wherein (1) the compound of Formula (II) is a carboxylic acid;

(2) $R_1$ is t-butyl substituted with one hydroxyl, and (i) $R_2$ is H, and each of l', m', n', u', v', and w' is 0, (ii) $R_2$ is hydroxyl or i-propyl substituted with one or two hydroxyl, and each of l', m', n', u', v', and w' is 0, or (iii) $R_2$ is H, hydroxyl or i-propyl optionally substituted with one hydroxyl, and the sum of l', m', n', u', v', and w' is 1;

(3) $R_1$ is t-butyl substituted with two hydroxyl, and (i) $R_2$ is H, hydroxyl or i-propyl optionally substituted with one hydroxyl, and each of l', m', n', u', v', and w' is 0, or (ii) $R_2$ is H, hydroxyl or i-propyl optionally substituted with one hydroxyl, and the sum of l', m', n', u', v', and w' is 1, or (4) $R_1$ is t-butyl substituted with three hydroxyl, $R_2$ is H or unsubstituted i-propyl, and each of l', m', n', u', v', and w' is 0.

2. The compound of claim 1 or the pharmaceutically acceptable salt or ester thereof, being in an isolated form.

3. The compound of claim 1, being of Formula (IIA):

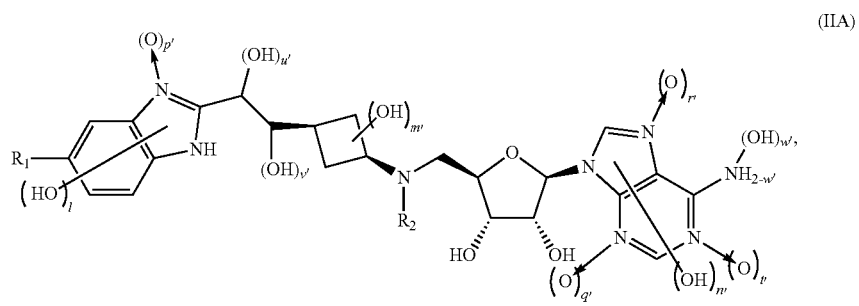

(IIA)

or Formula (IIB):

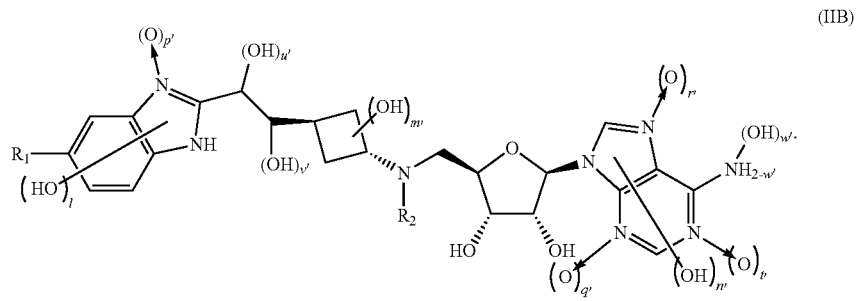

(IIB)

4. The compound of claim 1, comprising one hydroxyl in addition to the two hydroxyls on the tetrahydrofuran ring.

5. The compound of claim 1, wherein $R_1$ is t-butyl substituted with one hydroxyl, $R_2$ is H, and each of l', m', n', u', v', and w' is 0.

6. The compound of claim 1, being of a carboxylic acid.

7. The compound of claim 1, wherein $R_1$ is t-butyl substituted with one hydroxyl and one oxo, and wherein the hydroxyl and oxo together with the carbon to which they are attached form —COOH.

8. The compound of claim 1, wherein $R_1$ is —C(CH$_3$)$_2$COOH), $R_2$ is H or unsubstituted i-propyl, and each of l', m', n', u', v', and w' is 0.

9. The compound of claim 1, comprising two or three hydroxyls in addition to the two hydroxyls on the tetrahydrofuran ring.

10. The compound of claim 1, wherein $R_1$ is t-butyl substituted with one hydroxyl, and (i) $R_2$ is hydroxyl or i-propyl substituted with one or two hydroxyl, and each of l', m', n', u', v', and w' is 0, or (ii) $R_2$ is H, hydroxyl, or i-propyl optionally substituted with one hydroxyl, and the sum of l', m', n', u', v', and w' is 1.

11. The compound of claim 1, wherein $R_1$ is t-butyl substituted with two hydroxyl, and (i) $R_2$ is H, hydroxyl or i-propyl optionally substituted with one hydroxyl, and each of l', m', n', u', v', and w' is 0, or (ii) $R_2$ is H, hydroxyl or i-propyl optionally substituted with one hydroxyl, and the sum of l', m', n', u', v', and w' is 1.

12. The compound of claim 1, wherein $R_1$ is t-butyl substituted with three hydroxyl, $R_2$ is H or unsubstituted i-propyl, and each of l', m', n', u', v', and w' is 0.

13. The compound of claim 1, comprising four hydroxyls in addition to the two hydroxyls on the tetrahydrofuran ring.

14. The compound of claim 1, comprising five or more hydroxyls in addition to the two hydroxyls on the tetrahydrofuran ring.

15. The compound of claim 1, wherein the compound is selected from the group consisting of Compounds 49-54, 56, 57, 63-89, 107, and 110-112.

16. A pharmaceutical composition comprising a compound of Formula (II):

when $R_1$ is t-butyl substituted with only one hydroxyl, $R_2$ is H, hydroxyl, or i-propyl substituted with one or more hydroxyl; and wherein
(1) the compound of Formula (II) is a carboxylic acid;
(2) $R_1$ is t-butyl substituted with one hydroxyl, and (i) $R_2$ is H, and each of l', m', n', u', v', and w' is 0, (ii) $R_2$ is hydroxyl or i-propyl substituted with one or two hydroxyl, and each of l', m', n', u', v', and w' is 0, or (iii) $R_2$ is H, hydroxyl or i-propyl optionally substituted with one hydroxyl, and the sum of l', m', n', u', v', and w' is 1;
(3) $R_1$ is t-butyl substituted with two hydroxyl, and (i) $R_2$ is H, hydroxyl or i-propyl optionally substituted with one hydroxyl, and each of l', m', n', u', v', and w' is 0, or (ii) $R_2$ is H, hydroxyl or i-propyl optionally substituted with one hydroxyl, and the sum of l', m', n', u', v', and w' is 1; or
(4) $R_1$ is t-butyl substituted with three hydroxyl, $R_2$ is H or unsubstituted i-propyl, and each of l', m', n', u', v', and w' is 0.

17. The pharmaceutical composition of claim 16, wherein the compound of Formula (II) or the pharmaceutically acceptable salt or ester thereof is in an isolated form.

18. A method of treating cancer comprising administering to a subject in need thereof a therapeutically effective amount of the pharmaceutical composition of claim 16.

19. A method of treating hematological cancer comprising administering to a subject in need thereof a therapeutically effective amount of the pharmaceutical composition of claim 16.

20. A method of treating a disorder mediated by a translocation of a gene on chromosome 11q23, comprising administering to a subject in need thereof a therapeutically effective amount of the pharmaceutical composition of claim 16.

21. A method of treating a disorder mediated by DOT1L-mediated protein methylation, comprising administering to a subject in need thereof a therapeutically effective amount of the pharmaceutical composition of claim 16.

22. A method of treating leukemia comprising administering to a subject in need thereof a therapeutically effective amount of the pharmaceutical composition of claim 16.

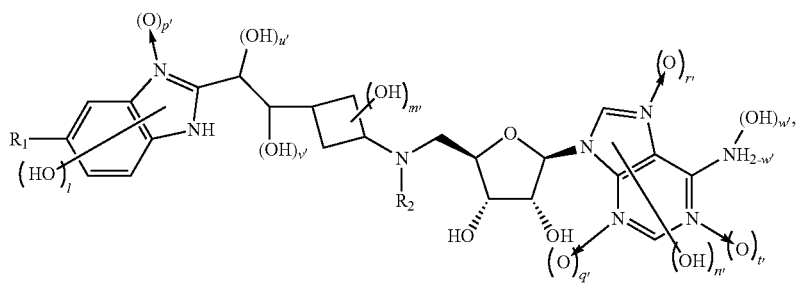

(II)

or a pharmaceutically acceptable salt or ester thereof, and a pharmaceutically acceptable carrier, wherein
$R_1$ is t-butyl substituted with one or more substituents selected from hydroxyl and oxo;
$R_2$ is H, hydroxyl, unsubstituted i-propyl, or i-propyl substituted with one or more hydroxyl;
l' is 0, 1, 2, or 3;
each of m' and n', independently, is 0, 1, or 2;
each of p', q', r', t', u', v', and w', independently, is 0 or 1; and 23. The method of claim 22, wherein the leukemia is acute myeloid leukemia, acute lymphocytic leukemia or mixed lineage leukemia.

24. The method of claim 22, wherein the leukemia is characterized by a chromosomal rearrangement.

25. The method of claim 24, wherein said chromosomal rearrangement is chimeric fusion of mixed lineage leukemia gene (MLL) or partial tandem duplication of MLL (MLL-PTD).

26. The method of claim 25, wherein the subject has an increased level of HOXA9, Fms-like tyrosine kinase 3 (FLT3), MEIS1, and/or DOT1L.

27. A method for treating leukemia in a subject comprising:
1) (a) detecting the level of HOXA9, FLT3, MEIS1, and/or DOT1L in a biological sample obtained from the subject, wherein an increased level of HOXA9, FLT3, MEIS1, and/or DOT1L indicates the subject is responsive to the compound of claim 1, or (b) detecting the presence of a genetic lesion of MLL in the sample; and
2) administering to the subject a therapeutically effective amount of the compound of claim 1 when the subject is responsive to the compound or when the genetic lesion is present in the sample.

28. The method of claim 27, wherein the sample is selected from bone marrow, peripheral blood cells, blood, plasma, serum, urine, saliva, a cell, or a tumor tissue.

29. The method of claim 28, wherein the genetic lesion is chimeric fusion of MLL or MLL-PTD.

* * * * *

UNITED STATES PATENT AND TRADEMARK OFFICE
CERTIFICATE OF CORRECTION

PATENT NO. : 10,400,005 B2
APPLICATION NO. : 15/632173
DATED : September 3, 2019
INVENTOR(S) : Nigel J. Waters Page 1 of 1

It is certified that error appears in the above-identified patent and that said Letters Patent is hereby corrected as shown below:

In the Claims

At Column 123, Lines 16-34, in Claim 1:

"
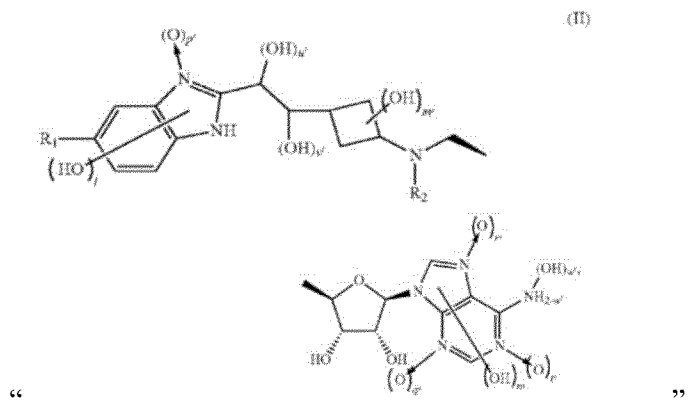
"

Should read:

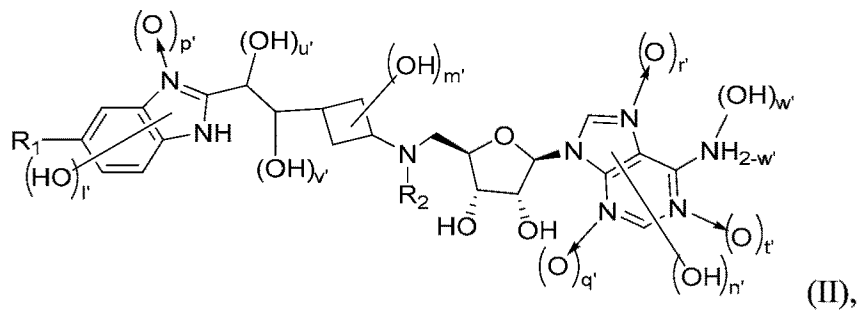

--                                                                 --

Signed and Sealed this
Twelfth Day of November, 2019

Andrei Iancu
*Director of the United States Patent and Trademark Office*